US009217749B2

(12) United States Patent
Sabbadini et al.

(10) Patent No.: US 9,217,749 B2
(45) Date of Patent: *Dec. 22, 2015

(54) IMMUNE-DERIVED MOIETIES REACTIVE AGAINST LYSOPHOSPHATIDIC ACID

(75) Inventors: Roger A. Sabbadini, Lakeside, CA (US); William A. Garland, San Clemente, CA (US); Genevieve Hansen, San Diego, CA (US)

(73) Assignee: Lpath, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/755,721

(22) Filed: May 30, 2007

(65) Prior Publication Data
US 2008/0145360 A1   Jun. 19, 2008

Related U.S. Application Data

(60) Provisional application No. 60/810,185, filed on May 31, 2006, provisional application No. 60/835,569, filed on Aug. 4, 2006, provisional application No. 60/923,644, filed on Apr. 16, 2007.

(51) Int. Cl.
| | |
|---|---|
| *G01N 33/92* | (2006.01) |
| *C07K 16/18* | (2006.01) |
| *C07K 16/30* | (2006.01) |
| *C12P 21/08* | (2006.01) |
| *A61K 47/48* | (2006.01) |
| *A61K 39/00* | (2006.01) |

(52) U.S. Cl.
CPC .......... *G01N 33/92* (2013.01); *A61K 47/4833* (2013.01); *A61K 47/48053* (2013.01); *A61K 47/48215* (2013.01); *A61K 47/48284* (2013.01); *C07K 16/18* (2013.01); *C07K 16/30* (2013.01); *A61K 2039/505* (2013.01); *C07K 2317/24* (2013.01); *C07K 2317/56* (2013.01); *C07K 2317/73* (2013.01); *C07K 2317/74* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,150,949 A | 4/1979 | Smith |
| 4,275,149 A | 6/1981 | Litman et al. |
| 4,816,397 A | 3/1989 | Boss et al. |
| 4,816,450 A | 3/1989 | Bell et al. |
| 4,816,567 A | 3/1989 | Cabilly et al. |
| 4,937,232 A | 6/1990 | Bell et al. |
| 5,061,626 A | 10/1991 | Baldo et al. |
| 5,079,263 A | 1/1992 | Zeeck et al. |
| 5,110,987 A | 5/1992 | Liotta et al. |
| 5,137,919 A | 8/1992 | Igarashi et al. |
| 5,151,360 A | 9/1992 | Handa et al. |
| 5,225,539 A | 7/1993 | Winter |
| 5,248,824 A | 9/1993 | Igarashi et al. |
| 5,260,288 A | 11/1993 | Igarashi et al. |
| 5,331,014 A | 7/1994 | Kimura et al. |
| 5,369,030 A | 11/1994 | Hannun et al. |
| 5,391,800 A | 2/1995 | Igarashi et al. |
| 5,430,160 A | 7/1995 | Holton |
| 5,444,087 A | 8/1995 | Patel et al. |
| 5,585,476 A | 12/1996 | MacLennan et al. |
| 5,620,689 A | 4/1997 | Allen |
| 5,627,171 A | 5/1997 | Park et al. |
| 5,663,404 A | 9/1997 | Igarashi et al. |
| 5,677,288 A | 10/1997 | Marangos |
| 5,677,337 A | 10/1997 | Wei et al. |
| 5,851,782 A | 12/1998 | Hannun et al. |
| 5,877,167 A | 3/1999 | Igarashi et al. |
| 5,888,793 A | 3/1999 | Hillman |
| 5,919,687 A | 7/1999 | Chatterjee |
| 5,929,039 A | 7/1999 | Woodcock et al. |
| 5,989,803 A | 11/1999 | Tabas et al. |
| 6,051,598 A | 4/2000 | Shayman et al. |

(Continued)

FOREIGN PATENT DOCUMENTS

| | | |
|---|---|---|
| EP | 0173648 A2 | 3/1986 |
| EP | 0404097 A2 | 12/1990 |

(Continued)

OTHER PUBLICATIONS

Chen et al. (Bioorganic & Medicinal Chemistry Letters 2000; 10: 1691-1693).*
Horgan et al. (Biochemical and Biophysical Research Communications 2004; 319: 83-94).*
Campbell, A. (Laboratory Techniques in Biochemistry and Molecular Biology, vol. 13, Chapter 1, pp. 1-33, 1984).*
Qian, L. (Molecular Design and Chemical Synthesis of Affinity Probes for Lysophosphatidic Acid Receptors, Dissertation, U. of Utah, May 2004).*
Xu et al. (Clin. Cancer Res. Oct. 1995 1: 1223-1232).*

(Continued)

*Primary Examiner* — Peter J Reddig
(74) *Attorney, Agent, or Firm* — Acuity Law Group, P.C.; Daniel M. Chambers

(57) ABSTRACT

Compositions and methods for producing monoclonal antibodies and their derivatives reactive against bioactive lipid targets are described. These compositions include derivatized lipids, each of which comprises a bioactive lipid that having a polar head group and at least one hydrocarbon chain (e.g., a lysolipid such as lysophosphatidic acid or sphingosine-1-phosphate) in which a carbon atom has been derivatized with a pendant reactive group; immunogens made by linking a derivatized lipid to a carrier moiety (e.g., a carrier protein, polyethylene glycol, colloidal gold, alginate, or a silicone bead); monoclonal antibodies and derivatives produced by immunizing an animal with such an immunogen; and therapeutic and diagnostic compositions containing such antibodies and antibody derivatives. Methods for making such derivatized lipids, immunogens, and monoclonal antibodies and derivatives, methods for detecting such antibodies once generated, and therapeutic and diagnostic methods for using such antibodies and derivatives, are also described.

5 Claims, 24 Drawing Sheets

(56) References Cited

U.S. PATENT DOCUMENTS

| | | | |
|---|---|---|---|
| 6,057,126 A | 5/2000 | Munroe et al. | |
| 6,130,067 A | 10/2000 | Tsui | |
| 6,140,060 A | 10/2000 | Chun et al. | |
| 6,187,562 B1 | 2/2001 | Duckworth et al. | |
| 6,210,976 B1 | 4/2001 | Sabbadini | |
| 6,248,553 B1 | 6/2001 | Small et al. | |
| 6,255,063 B1 | 7/2001 | Small et al. | |
| 6,284,798 B1 | 9/2001 | Amtmann et al. | |
| 6,300,308 B1 | 10/2001 | Schroit | |
| 6,306,911 B1 | 10/2001 | Wachter et al. | |
| 6,312,294 B1 | 11/2001 | Lai | |
| 6,323,201 B1 | 11/2001 | Carson et al. | |
| 6,352,844 B1 | 3/2002 | Maurer et al. | |
| 6,423,527 B1 | 7/2002 | Saba et al. | |
| 6,500,633 B1 | 12/2002 | Compton et al. | |
| 6,534,322 B1 | 3/2003 | Sabbadini | |
| 6,534,323 B1* | 3/2003 | Sabbadini | 436/518 |
| 6,610,835 B1 | 8/2003 | Liotta et al. | |
| 6,613,322 B2 | 9/2003 | Tabas et al. | |
| 6,649,362 B2 | 11/2003 | Gamble et al. | |
| 6,783,760 B1 | 8/2004 | Thorpe et al. | |
| 6,806,354 B2 | 10/2004 | Schroit | |
| 6,818,213 B1 | 11/2004 | Thorpe et al. | |
| 6,858,383 B2 | 2/2005 | Sabbadini | |
| 6,881,546 B2 | 4/2005 | Sabbadini | |
| 6,967,022 B1 | 11/2005 | Livingston et al. | |
| 7,060,808 B1 | 6/2006 | Goldstein et al. | |
| 7,169,390 B2 | 1/2007 | Sabbadini | |
| 7,700,792 B2 | 4/2010 | Hayashi et al. | |
| 8,158,124 B2* | 4/2012 | Sabbadini et al. | 424/133.1 |
| 2001/0041688 A1 | 11/2001 | Waeber et al. | |
| 2002/0123084 A1* | 9/2002 | Mills et al. | |
| 2002/0150582 A1 | 10/2002 | Friedrichs et al. | |
| 2003/0096022 A1 | 5/2003 | Sabbadini | |
| 2003/0125533 A1 | 7/2003 | Kossida et al. | |
| 2003/0219782 A1 | 11/2003 | Saba et al. | |
| 2005/0226862 A1 | 10/2005 | Sabbadini | |
| 2006/0258616 A1 | 11/2006 | Wolf et al. | |
| 2007/0148168 A1* | 6/2007 | Sabbadini et al. | 424/133.1 |
| 2007/0161604 A1* | 7/2007 | Hayashi et al. | 514/100 |
| 2010/0034814 A1 | 2/2010 | Sabbadini et al. | |
| 2011/0064744 A1 | 3/2011 | Sabbadini et al. | |
| 2014/0199293 A1* | 7/2014 | Sabbadini et al. | 424/133.1 |

FOREIGN PATENT DOCUMENTS

| | | |
|---|---|---|
| EP | 0125023 B1 | 6/1991 |
| EP | 0173663 B1 | 1/1992 |
| EP | 0519596 A1 | 12/1992 |
| EP | 0120694 B1 | 7/1993 |
| EP | 0194276 B1 | 8/1993 |
| EP | 0239400 B1 | 8/1994 |
| EP | 0736770 A2 | 10/1996 |
| JP | 1987 09-110722 A | 4/1987 |
| JP | 2000-293181 A | 10/2000 |
| JP | 2002-243737 A | 8/2002 |
| WO | 86/01533 A1 | 3/1986 |
| WO | 93/11161 A1 | 6/1993 |
| WO | 93/21528 A1 | 10/1993 |
| WO | 94/07593 A1 | 4/1994 |
| WO | 97/44019 A1 | 11/1997 |
| WO | 98/03529 A1 | 1/1998 |
| WO | 98/28445 A1 | 7/1998 |
| WO | 98/40349 A1 | 9/1998 |
| WO | 98/57179 A1 | 12/1998 |
| WO | 99/07855 A1 | 2/1999 |
| WO | 99/12890 A1 | 3/1999 |
| WO | 99/16888 A2 | 4/1999 |
| WO | 99/33522 A2 | 7/1999 |
| WO | 99/33972 A1 | 7/1999 |
| WO | 99/38983 A1 | 8/1999 |
| WO | 99/41265 A1 | 8/1999 |
| WO | 99/41266 A1 | 8/1999 |
| WO | 99/46277 A1 | 9/1999 |
| WO | 99/61581 A2 | 12/1999 |
| WO | 00/00593 A2 | 1/2000 |
| WO | 00/21919 A1 | 4/2000 |
| WO | 00/40262 A1 | 7/2000 |
| WO | 00/52173 A2 | 9/2000 |
| WO | 00/56135 A2 | 9/2000 |
| WO | 00/58448 A1 | 10/2000 |
| WO | 00/58491 A1 | 10/2000 |
| WO | 00/59517 A1 | 10/2000 |
| WO | 00/70028 A1 | 11/2000 |
| WO | 00/72833 A2 | 12/2000 |
| WO | 01/04108 A1 | 1/2001 |
| WO | 01/04139 A2 | 1/2001 |
| WO | 01/07418 A2 | 2/2001 |
| WO | 01/31029 A2 | 5/2001 |
| WO | 01/38295 A1 | 5/2001 |
| WO | 01/55410 A2 | 8/2001 |
| WO | 01/57057 A1 | 8/2001 |
| WO | 01/60990 A2 | 8/2001 |
| WO | 01/71045 A2 | 9/2001 |
| WO | 01/72701 A1 | 10/2001 |
| WO | 01/08593 A1 | 11/2001 |
| WO | 01/80903 A1 | 11/2001 |
| WO | 02/17899 A2 | 3/2002 |
| WO | 02/051439 A2 | 7/2002 |
| WO | 03/000701 A1 | 1/2003 |
| WO | 2004/006847 A2 | 1/2004 |
| WO | WO 2005/064332 A1 * | 7/2005 ............. G01N 33/50 |
| WO | 2006/105062 A2 | 10/2006 |
| WO | 2008/150841 A1 | 12/2008 |

OTHER PUBLICATIONS

Smith et al., Hypoxia, calcium fluxes, and inotropic state: Studies in cultured heart cells, Am. Heart J., 1982, pp. 716-723, vol. 103, Iss. 4, Pt. 2.

Smith et al., Purified Fumonisin B1 Decreases Cardiovascular Function but does not Alter Pulmonary Capillary Permeability in Swine, Toxicol. Sci., 2000, pp. 240-249, vol. 56, Iss. 1.

Spence et al., A new Zn2+-stimulated sphingomyelinase in fetal bovine serum, J. Biol. Chem., 1989, pp. 5358-5363, vol. 264, Iss. 10.

Spence, Sphingomyelinases, Adv. Lipid Res., 1993, pp. 3-23, vol. 26.

Spiegel et al., Sphingolipid metabolism and cell growth regulation, FASEB J., 1996, pp. 1388-1397, vol. 10, Iss. 12.

Spiegel et al., Review: Roles of Sphingosine-1-phosphate in Cell Growth, Differentiation, and Death, Biochemistry (Mosc)., 1998, pp. 69-73, vol. 63, Iss. 1.

Spiegel et al., Functions of a new family of sphingosine-1-phosphate receptors, Biochim. Biophys. Acta, 2000, pp. 107-116, vol. 1484, Iss. 2-3.

Sucheck et al., Combinatorial synthesis of aminoglycoside libraries, Curr. Opin. Drug Disc. Develop., 2001, pp. 462-470, vol. 4, Iss. 4 (Abstract Only).

Sugita at al, Ceramidase and ceramide synthesis in human kidney and cerebellum. Description of a new alkaline ceramidase, Biochim. Biophys. Acta, 1975, pp. 125-131, vol. 398, Iss. 1.

Sugiyama et al., Sphingosine 1-phosphate induces sinus tachycardia and coronary vasoconstriction in the canine heart, Cardiovasc. Res., 2000, pp. 119-125, vol. 46, Iss. 1.

Sumnicht et al., Lipid Composition of Transverse Tubular Membranes from Normal and Dystrophic Skeletal Muscle, Arch. Biochem. Biophys., 1982, pp. 628-637, vol. 215, Iss. 2.

Szulc et al., A facile regioselective synthesis of sphingosine 1-phosphate and ceramide 1-phosphate, Tetrahedron Lett., 2000, pp. 7821-7824, vol. 41, Iss. 41.

Tamura et al., Mass Production of Sphingomyelinase of Bacillus cereus by a Protein-Hyperproducing Strain, Bacillus brevis 47, and Its Purification, J. Biochem. (Tokyo), 1992, pp. 488-491, vol. 112, Iss. 4.

Tanaka et al., Structural Elucidation of Scyphostatin, an Inhibitor of Membrane-Bound Neutral Sphingomyelinase, J. Am. Chem. Soc., 1997, pp. 7871-7872, vol. 199, Iss. 33.

Tani et al., Purification and Characterization of a Neutral Ceramidase from Mouse Liver: A single Protein Catalyzes the Reversible Reaction in Which Ceramide is Both Hydrolyzed and Synthesized, J. Biol. Chem., 2000, pp. 3462-3468, vol. 275, Iss. 5.

(56) References Cited

OTHER PUBLICATIONS

Tazabekova et al., Synthesis of sphingomyelin phosphonate analogues and preparation of an affinity sorbent for the sphingomyelinase purification, Bioorg. Khim., 1987, pp. 648-653, vol. 13, Iss. 5 (English Abstract Only).
Tomita et al.., Secondary structure of sphingomyelinase from Bacillus cereus, J. Biochem. (Tokyo), 1990, pp. 811-815, vol. 108, Iss. 5.
Tomiuk et al., Cloned mammalian neutral sphingomyelinase: Functions in sphingolipid signaling?, Proc. Natl. Acad. Sci. USA, 1998, pp. 3638-3643, vol. 95, Iss. 7.
Torley et al., A turbidometric assay for phospholipase C and sphingomyelinase, Anal. Biochem., 1994, pp. 461-464, vol. 222, Iss. 2.
Tosaka et al., Sphingosine 1-phosphate contracts canine basilar arteries in vitro and in vivo: possible role in pathogenesis of cerebral vasospasm, Stroke, 2001, pp. 2913-2919, vol. 32, Iss. 12.
Triola et al., Synthesis of a Cyclopropene Analogue of Ceramide, a Potent Inhibitor of Dihydroceramide Desaturase, Angew. Chem. Int. Ed., 2001, pp. 1960-1962, vol. 40, Iss. 10.
Tsunoda et al., Early Fumonisin B1 Toxicity in Relation to Disrupted Sphingolipid Metabolism in Male BALB/c Mice, J. Biochem. Mol. Toxicol., 1998, pp. 281-289, vol. 12, Iss. 5.
Uchida et al., Alutenusin, a Specific Neutral Sphingomyelinase Inhibitor, Produced by Penicillium sp. FO-7436, J. Antibiot. (Tokyo), 1999, pp. 572-574, vol. 52, Iss. 6.
Urdal, The Biochemistry of Tumor Associated Gangliotriosylceramide and the Use of This Glycolipid as a Target for Antibody Dependent, Avidin Mediated Drug Killing of Tumor Cells, Dissertation Abstracts Int., 1980, pp. 4062-4063, vol. 41, Iss. 11B (Abstract Only).
Usta et al., Structural Requirements of Ceramide and Sphingosine Based Inhibitors of Mitochondrial Ceramidase, Biochemistry, 2000, pp. 9657-9668, vol. 40, Iss. 32.
Van Brocklyn et al., Sphingosine 1-phosphate-induced cell rounding and neurite retraction are mediated by the G protein-coupled receptor H218, J. Biol. Chem., 1999, pp. 4626-4632, vol. 274, Iss. 8.
Van Veldhoven et al., Human sphingosine-1-phosphate lyase: cDNA cloning, functional expression studies and mapping to chromosome 10q22(1), Biochim. Biophys. Acta, 2000, pp. 128-134, vol. 1487, Iss. 2-3.
Van Veldhoven, Shingosine-1-phosphate Lyase, Methods Enzymol. 1999, pp. 244-254, vol. 311.
Van Veldhoven et al., Sphingosine-Phosphate Lyase, Adv. Lipid Res., 1993, pp. 69-98, vol. 26.
Visentin et al., Validation of an anti-sphingosine-1-phosphate antibody as a potential therapeutic in reducing growth, invasion, and angiogenesis in multiple tumor lineages, Cancer Cell., 2006, pp. 225-238, vol. 9, Iss. 3.
Vivekananda et al., Sphingomyelin metabolites inhibit sphingomyelin synthase and CTP:phosphocholine cytidylyltransferase, Am. J. Physiol. Lung Cell. Mol. Physiol., 2001, pp. L98-L107, vol. 228, Iss. 1.
Walev et al., Selective killing of human monocytes and cytokine release provoked by sphingomyelinase (beta-toxin) of Staphylococcus aureus, Infect. Immun., 1996, pp. 2974-2979, vol. 64, Iss. 8.
Wang et al., A Single Amino Acid Determines Lysophospholipid Specificity of the S1 P1 (EDG1) and LPA1 (EDG2) Phospholipid Growth Factor Receptors, J. Biol. Chem., 2001, pp. 49213-49220, vol. 276, Iss. 52.
Webster's Dictionary, 1990, p. 1135.
Winter et al., Making antibodies by phage display technology, Annu. Rev. Immunol., 1994, pp. 433-455, vol. 12.
Wright et al., Genetically engineered antibodies: progress and prospects, Crit. Rev. Immunol., 1992, pp. 125-168, vol. 12, Iss. 3-4.
Xia et al., Tumor necrosis factor-alpha induces adhesion molecule expression through the sphingosine kinase pathway, Proc. Natl. Acad. Sci. USA, 1988, pp. 14196-14201, vol. 95, No. 24.
Xia et al., High density lipoproteins (HDL) interrupt the sphingosine kinase signaling pathway. A possible mechanism for protection against atherosclerosis by HDL, J. Biol. Chem., 1999, pp. 33143-33147, vol. 274, Iss. 46.
Xu et al., Involvement of de novo ceramide biosynthesis in tumor necrosis factor-alpha/cycloheximide-induced cerebral endothelial cell death, J. Biol. Chem., 1998, pp. 16521-16526, vol. 273, Iss. 26.
Xu et al., Sphingosylphosphorylcholine is a ligand for ovarian cancer G-protein-coupled receptor 1, Nat. Cell Biol., 2000, pp. 261-267, vol. 2, Iss. 5.
Yada et al., Purification and biochemical characterization of membrane-bound epidermal ceramidases from guinea pig skin, J. Biol. Chem., 1995, pp. 12677-12684, vol. 270, Iss. 21.
Yamada et al., Nucleotide sequence and expression in Escherichia coli of the gene coding for sphingomyelinase of Bacillus cereus, Eur. J. Biochem., 1988, pp. 213-220, vol. 175, Iss. 2.
Yamaji et al., Lysenin, a novel sphingomyelin-specific binding protein, J. Biol. Chem., 1998, pp. 5300-5306, vol. 273, Iss. 9.
Yamanaka et al., Acid Sphingomyelinase of Human Brain: Purification to Homogeneity, J. Neurochem., 1982, pp. 1753-1764, vol. 38, Iss. 6.
Yamazaki et al., Edg-6 as a Putative Sphingosine 1-Phosphate Receptor Coupling to Ca2+ Signaling Pathway, Biochem. Biophys. Res. Commun., 2000, pp. 583-589, vol. 268, Iss. 2.
Yatomi et al., Sphiongosine-1-Phosphate: A Platelet-Activating Sphingolipid Released from Agonist Stimulated Human Platelets, Blood, 1995, pp. 193-202, vol. 86, Iss. 1.
Yatomi et al., Sphingosine 1-phosphate induces platelet activation through an extracellular action and shares a platelet surface receptor with lysophosphatidic acid, J. Biol. Chem., 1997, pp. 5291-5297, vol. 272, Iss. 8.
Yatomi et al., Sphingosine 1-phosphate, a bioactive sphingolipid abundantly stored in platelets, is a normal constituent of human plasma and serum, J. Biochem., 1997, pp. 969-973, vol. 121, Iss. 5.
Yellon et al., Ischaemic preconditioning limits infarct size in the rat heart, Cardiovasc. Res., 1992, pp. 983-987, vol. 26, Iss. 10.
Yoshimura et al., Inhibition of Neutral Sphingomyelinase Activation and Ceramide Formation by Glutathione in Hypoxic PC12 Cell Death, J. Neurochem., 1999, pp. 675-683, vol. 73, Iss. 2.
Gatt et al., Niemann Pick disease: presence of the magnesium-dependent sphingomyelinase in brain of the infantile form of the disease, J. Neurochem., 1978, pp. 547-550, vol. 31, Iss. 2.
Gavrilenko et al., Nucleotide sequence of phospholipase C and sphingomyelinase genes from Bacillus cereus BKM-B164, Bioorg. Khim., 1993, pp. 133-138, vol. 19, Iss. 1 (English Abstract Only).
Geeraert et al., Conversion of dihydroceramide into ceramide: involvement of a desaturase, Biochem. J., 1997, pp. 125-132, vol. 327, Pt. 1.
Ghosh et al., Effects of gentamicin on sphingomyelinase activity in cultured human renal proximal tubular cells, J. Biol. Chem., 1987, pp. 12550-12556, vol. 262, Iss. 26.
Ghosh et al., Identification, partial purification, and localization of a neutral sphingomyelinase in rabbit skeletal.
Gilmore et al., A Bacillus cereus cytolytic determinant, cereolysin AB, which comprises the phospholipase C and sphingomyelinase genes: a nucleotide sequence and genetic linkage, J. Bacteriol., 1989, pp. 744-753, vol. 171, Iss. 2.
Glickman et al., Molecular Cloning, Tissue-Specific Expression, and Chromosomal Localization of a Novel Nerve Growth Factor-Regulated G-Protein-Coupled Receptor, nrg-1, Mol. Cel. Neurosci., 1999, pp. 141-152, vol. 14, Iss. 2.
Goetzl et al., Diversity of cellular receptors and functions for the lysophospholipid growth factors lysophosphatidic acid and sphingosine 1-phosphate, Faseb J., 1998, pp. 1589-1598, vol. 12, Iss. 15.
Goetzl et al., Eicosanoids and Other Bioactive Lipids in Cancer, Inflammation, and Radiation Injury, 4. 38: A Subfamily of G Protein-Coupled Cellular Receptors for Lysophospholipids and Lysosphingolipids, Introduction: The Biochemistry and Biology of Lipid Phosphoric Acids, Adv. Exp. Med. Biol., 1999, 259-264, vol. 469.

(56) References Cited

OTHER PUBLICATIONS

Gonda, et al., The novel sphingosine 1-phosphate receptor AGR16 is coupled via pertussis toxin-sensitive and -insensitive G-proteins to multiple signalling pathways, Biochem. J., 1999, pp. 67-75, vol. 337, Pt. 1.

Gonzalez-Zorn et al., The smcL gene of Listeria ivanovii encodes a sphingomyelinase C that mediates bacterial escape from the phagocytic vacuole, Mol. Microbial., 1999, pp. 510-523, vol. 33, Iss. 3.

Graler et al., EDG6, a Novel G-Protein-Coupled Receptor Related to Receptors for Bioactive Lysophospholipids, Is Specifically Expressed in Lymphoid Tissue, Genomics, 1998, pp. 164-169, vol. 53, Iss. 2.

Granziero et al., Adoptive immunotherapy prevents prostate cancer in a transgenic animal model, Eur. J. Immunol., 1999, pp. 1127-1138, vol. 29, Iss. 4.

Gunther, Myocardial contractility after infarction and carnitine palmitoyltransferase I inhibition in rats, Eur. J. Pharma., 2000, pp. 123-126, vol. 406, Iss. 1.

Hakogi et al., Stereocontrolled synthesis of a sphingomyelin methylene analogue as a sphingomyelinase inhibitor, Org. Lett., 2000, pp. 2627-2629, vol. 2, Iss. 17.

Hanada et al., Specificity of Inhibitors of Seine Palmitoyltransferase (SPT), a Key Enzyme in Sphingolipid Biosynthesis in Intact Cells: A novel evaluation system using an SPT-defective mammalian cell mutant, Biochem. Pharmacol., 2000, 1211-1216, vol. 59, Iss. 10.

Hannun et al., Functions of Sphingolipids and Sphingolipid Breakdown Products in Cellular Regulation, Science, 1989, pp. 500-507, vol. 243, No. 4890.

Hannun et al.., The Sphingomyelin Cycle: A Prototypic Sphingolipid Signaling Pathway, Adv. Lipid Res., 1993, pp. 27-41, vol. 25.

Hannun, Functions of Ceramide in Coordinating Cellular Responses to Stress, Science, 1996, pp. 1855-1859, vol. 274, No. 5294.

Hannun at al, Ceramide in the eukaryotic stress response, Trends Cell Biol., 2000, pp. 73-80, vol. 10, Iss. 2.

He et al., A Fluorescence-Based High-Performance Liquid Chromatography Assay to Determine Acid Ceramidase Activity, Anal. Biochem., 1999, pp. 264-269, vol. 274, Iss. 2.

Heringdorf et al., Stimulation of intracellular sphingosine-1—phosphate production by G-protein-coupled sphingosine-1—phosphate receptors, Eur. J. Pharmacol., 2001, pp. 145-154, vol. 414, Iss. 2-3.

Hernandez et al., Rapid Activation of Neutral Sphingomyelinase by Hypoxia-Reoxygenation of Cardiac Myocytes, Circ. Res., 2000, pp. 198-204, vol. 86, Iss. 2.

Hetland et al., Phospholipase C from Bacillus cereus has sphingomyelinase activity, Scand. J. Clin. Lab. Invest., 1982, Iss. 57-61, vol. 42, Iss. 1.

Higuchi et al., Acidic sphingomyelinase-generated ceramide is needed but not sufficient for TNF-induced apoptosis and nuclear factor-kappa B activation, J. Immunol., 1996, pp. 297-304, vol. 157, Iss. 1.

Hinkovska-Glacheva et al., Activation of a Plasma Membrane-Associated Neutral Sphingomyelinase and Concomitant Ceramide Accumulation During IgG-Dependent Phagocytosis in Human Polymorphonuclear Leukocytes, Blood, 1998, pp. 4761-4769, vol. 91, No. 12.

Hise et al., Fatty Acyl Chain Composition in the Determination of Renal Membrane Order, J. Clin. Invest., 1986, pp. 768-773, vol. 77, Iss. 3.

HLA et al., An Abundant Transcript Induced in Differentiating Human Endothelial Cells Encodes a Polypeptide with Structural Similarities to G-protein-coupled Receptors, J. Biol. Chem., 1990, pp. 9308-9313, vol. 265, Iss. 16.

Hofmann et al., Cloning and characterization of the mammalian brain-specific, Mg2+-dependent neutral sphingomyelinase, Proc. Natl. Acad. Sci. USA, 2000, pp. 5895-5900, vol. 97, Iss. 11.

Hofstadler et al., Multiplexed Screening of Neutral Mass-Tagged RNA Targets against Ligand Libraries with Electrospray Ionization FTICR MS: a Paradigm for High-Throughput Affinity Screening, Anal. Chem., 1999, pp. 3436-3440, vol. 71, Iss. 16.

Holopainen et al., Sphingomyelinase Activity. Associated with Human Plasma Low Density Lipoprotein, J Biol. Chem., 2000, pp. 16484-16489, vol. 275, Iss. 22.

Horn et al., Sphingofungins E and F: Novel Serinepalmitoyl Trans-Ferase Inhibitors From Paecilomyces variotii, J. Antibiot. (Tokyo), 1992, pp. 1692-1696, vol. 45, Iss. 10.

Hoye et al., Synthesis (and Alternative Proof of Configuration) of the Scyphostatin C(1')-C(20') Trienoyl Fragment, Organic Letts., 2000, pp. 1481-1483, vol. 2, Iss. 10.

Hudson, Recombinant antibody fragments, Curr. Op. Biotechnol., 1999, pp. 395-402, vol. 9, Iss. 4.

Humpf et al., Acylation of naturally occurring and synthetic 1-deoxysphinganines by ceramide synthase. Formation of N-palmitoyl-aminopentol produces a toxic metabolite of hydrolyzed fumonisin, AP1, and a new category of ceramide synthase inhibitor, J. Biol. Chem., 1998, pp. 19060-19064, vol. 273, Iss. 30.

Huwiler et al., Physiology and pathophysiology of sphingolipid metabolism and signling, Biochim. Biophys. Acta, 2000, pp. 63-99, vol. 1485, Iss.2-3.

Igarashi, Functional Roles of Sphingosine, Sphingosine 1-Phosphate, and Methylsphingosines: In Regard to Membrane Sphingolipid Signaling Pathways, J. Biochem., 1997, pp. 1080-1087, vol. 122, Iss. 6.

Igarashi, Sphinosine-1-Phosphate as an Intercellular Signaling Molecule, Ann. NY Acad. Sci.,1998, pp. 19-31, vol. 845.

Ikezawa et al., Studies on Sphingomyelinase of Bacillus Cereus. 1. Purification and Properties, Biochim. Biophys. Acta, 1978, pp. 247-256, vol. 528, Iss. 2.

Im et al., Characterization of a novel sphingosine 1-phosphate receptor, Edg-8, J. Biol. Chem., 2000, pp. 14281-14286, vol. 275, Iss. 19.

Im et al., Molecular Cloning and Characterization of a Lysophosphatidic Acid Receptor, Edg-7, Expressed in Prostate, Mol. Pharmacol., 2000, pp. 753-759, vol. 57, Iss. 4.

Izuhara et al., Studies toward the Total Synthesis of Scyphostatin: First Entry to the Highly Functionalized Cyclohexenone Segment, Organic Lett., 2001, pp. 1653-1656, vol. 3, Iss. 11.

Jimbo et al., Development of a New Inhibitor of Glucosylceramide Synthase, J. Biochem., 2000, pp. 485-491, vol. 127, Iss. 3.

Johansen et al., Bacillus cereus strain SE-1: nucleotide sequence of the sphingomyelinase C gene, Nucl. Acids Res., 1998, p. 10370, vol. 16, Iss. 21.

Jonghe et al., Structure-Activity Relationship of Short-Chain Sphingoid Bases As Inhibitors of Sphingosine Kinase, Bioorg. Medicinal Chem. Lett., 1999, pp. 3175-3180, vol. 9, Iss. 21.

Kajstura et al., Apoptotic and Necrotic Myocyte Cell Deaths Are Independent Contributing Variables of Infarct Size in Rats, Lab. Invest., 1996, pp. 86-107, vol. 74, Iss. 1.

Kanfer et al., The Metabolism of Sphingomyelin. I. Purification and properties of a sphingomyelin-cleaving enzyme from rat liver tissue, J. Biol. Chem., 1966, pp. 1081-1084, vol. 241, Iss. 5.

Katircioglu et al., Myocardial preservation in acute coronary artery occlusion with coronary sinus retroperfusion and camitine, J. Cardiovasc. Surg. (Torino), 1999, pp. 45-50, vol. 41, Iss. 1.

Kay et al., Identification of enzyme inhibitors from phage-displayed combinatorial peptide libraries, Comb. Chem. High Throughput Screen, 2001, pp. 535-543, vol. 4, Iss. 7 (Abstract Only).

Kester, Sphingolipid Metabolites and the Cellular Phenotype, Trends Glycosci. Glycotechnol., 1997, pp. 447-460, vol. 9, Iss. 50.

Meroni et al., Effect of N-Acetylsphingosine (C2) and the Ceramidase Inhibitor (1S,2R)-D-erythro-2-(n-myristoylamino)-1 phenyl-1-propanol on the Regulation of Sertoli Cell Function, J. Androl., 1999, pp. 619-625, vol. 20, Iss. 5.

Merrill Jr. et al., Activities of serine palmitoyltransferase (3-ketosphinganine synthase) in microsomes from different rat tissues, J. Lipid Res., 1993, pp. 617-622, vol. 26, Iss. 5.

Merrill Jr. et al., Fumonisins and other inhibitors of de novo sphingolipid biosynthesis, Adv. Lipid Res., 1993, pp. 215-234, vol. 26.

Michel et al., Characterization of Ceramide Synthesis. A Dihydroceramide Desaturase Introduces the 4,5-Trans-Double Bond of Sphingosine At the Level of Dihydroceramide, J. Biol. Chem., 1997, pp. 22432-22437, vol. 272, Iss. 36.

(56) References Cited

OTHER PUBLICATIONS

Milstien et al., Targeting sphingosine-1-phosphate: A novel avenue for cancer therapeutics, Cancer Cell., 2006, pp. 148-150, vol. 9, Iss. 3.

Mingeot-Leclercq et al., Aminoglycosides: activity and resistance, Antimicrob. Agents Chemother., 1999, pp. 727-734, vol. 43, Iss. 4.

Mingeot-Leclercq et al., Aminoglycosides: nephrotoxicity, Antimicrob. Agents Chemother., 1999, pp. 1003-1012, vol. 43, Iss. 5.

Mitsutake et al., Purification, Characterization, Molecular Cloning, and Subcellular Distribution of Neutral Ceramidase of Rat Kidney, J. Biol. Chem., 2001, pp. 26249-26259, vol. 276, Iss. 28.

Miyake, Serine palmitoyltransferase is the primary target of a sphingosine-like immunosuppressant, ISP-1/myriocin, Biochem. Biophys. Res. Commun., 1995, pp. 396-403, vol. 211, Iss. 2.

Mohan et al., Evidence that Neutral Sphingomyelinase of Cultured Murine Neuroblastoma Cells is Oriented Externally on the Plasma Membrane, Biochem. Biophys. Acta, 1984, pp. 339-342, vol. 777, Iss. 2.

Mohler et al., Soluble Tumor Necrosis Factor (TNF) Receptors Are Effective Therapeutic Agents in Lethal Endotoxemia and Function Simultaneously as Both TNF Carries and TNF Antagonists, J. Immunol., 1993, pp. 1548-1561, vol. 151, Iss. 3.

Nakajima et al., Biophysical J., 2000, p. 319A, vol. 78, Iss. 1, Part 2.

Nakajima et al., Expression and characterization of Edg-1 receptors in rat cardiomyocytes: Calcium deregulation in response to sphingosine 1-phosphate, Eur. J. Biochem., 2000, pp. 5679-5686, vol. 267, Iss. 18.

Napoli et al., Ischaemic preconditioning of rat myocardium: effects on postischaemic coronary endothelium hypermaebility and microcirculatory damage, J. Clin. Bas. Cardiol., 1998, pp. 37-42, vol. 1, Iss. 1.

Nikolova-Karakashian et al., Ceramidases, Meth. Enzymol., 1999, pp. 194-201, vol. 311.

Ohta et al., A possible role of sphingosine in induction of apoptosis by tumor necrosis factor-a in human neutrophils, FEBS Lett., 1994, pp. 267-270, vol. 355, Iss. 3.

Ohta et al., Induction of apoptosis by sphingosine in human leukemic HL-60 cells: a possible endogenous modulator of apoptotic DNA fragmentation occurring during phorbol ester-induced differentiation, Cancer Res., 1995, pp. 691-697, vol. 55, Iss. 3.

Okamoto et al., EDG1 Is a Functional Sphingosine-1-phosphate Receptor That Is Linked via a Gi/o to Multiple Signaling Pathways, Including Phospholipase C Activation, Ca2+ Mobilization, Ras-Mitogen-activated Protein Kinase Activation, and Adenylate Cyclase Inhibition, J. Biol. Chem., 1998, pp. 27104-27110, vol. 273, Iss. 42.

Okamoto et al., EDG3 Is a Functional Receptor Specific for Sphingosine 1-Phosphate and Sphingosylphosphorylcholine with Signaling Characteristics Distinct from EDG1 and AGR16, Biochem. Biophys. Res. Commun., 1999, pp. 203-208, vol. 260, Iss. 1.

Okazaki et al., Characteristics and partial purification of a novel cytosolic, magnesium-independent, neutral sphingomyelinase activated in the early signal transduction of 1 alpha,25-dihydroxyvitamin D3-induced HL-60 cell differentiation, J. Biol. Chem., 1994, pp. 4070-4077, vol. 269, Iss. 6.

Okino et al., Molecular Cloning, Sequencing, and Expression of the Gene Encoding Alkaline Ceramidase from Pseudomonas aeruginosa: Cloning of A Ceramidase Homologue from mycobacterium Tuberculosis, J. Biol. Chem., 1999, pp. 36616-36622, vol. 274, Iss. 51.

Olivera et al., Sphingosine-1-phosphate as second messenger in cell proliferation induced by PDGF and FCS mitogens, Nature, 1993, pp. 557-560, vol. 365, No. 6446.

Olivera et al., Assaying Sphingosine Kinase Activity, Methods Enzymol., 1999, pp. 215-223, vol. 311.

Olshefski et al., Glucosylceramide Synthase Inhibition Enhances Vincristine-Induced Cytotoxicity, Int. J. Cancer, 2001, pp. 131-138, vol. 93, Iss. 1.

Oral et al., Sphingosine mediates the immediate negative inotropic effects of tumor necrosis factor-alpha in the adult mammalian cardiac myocyte, J. Biol. Chem., 1997, pp. 4836-4842, vol. 272, Iss. 8.

Parrill et al., Identification of Edg1 Receptor Residues That Recognize Sphingosine 1-Phosphate, J. Biol. Chem., 2000, pp. 39379-39384, vol. 275, Iss. 50.

Pitson et al., Expression of a catalytically inactive sphingosine kinase mutant blocks agonist-induced sphingosine kinase activation. A dominant-negative sphingosine kinase, J. Biol. Chem., 2000, pp. 33945-33950, vol. 275, Iss. 43.

Pitson et al., Human sphingosine kinase: purification, molecular cloning and characterization of the native and recombinant enzymes, Biochem J., 2000, pp. 429-441, vol. 350, Pt. 2.

Presta et al., Humanization of an Anti-Vascular Endothelial Growth Factor Monoclonal Antibody for the Therapy of Solid Tumors and Other Disorders, Canc. Res., 1997, pp. 4593-4599, vol. 57, Iss. 20.

Raag et al., Single-chain Fvs, FASEB J., 1995, pp. 73-80, vol. 9, Iss. 1.

Rani et al., Cell Cycle Arrest Induced by an Inhibitor of Glucosylceramide Synthase, J. Biol. Chem., 1995, pp. 2859-2867, vol. 270, Iss. 6.

Riley et al., Alteration of tissue and serum sphinganine to sphingosine ratio: an early biomarker of exposure to fumonisin-containing feeds in pigs, Toxicol. Appl. Pharmacol., 1993, pp. 105-112, vol. 118, Iss. 1 (Abstract Only).

Riley et al., Fermentation, partial purification, and use of serine palmitoyltransferase inhibitors from Isaria (= Cordyceps) sinclairii, Meth. Enzymol., 1999, pp. 348-361, vol. 311.

Romiti et al., Characterization of sphingomyelinase activity released by thrombin-stimulated platelets, Mol. Cell. Biochem., 2000, pp. 75-81, vol. 205, Iss. 1-2.

Runcie at al, A Short and Efficient Route to Novel Scyphostatin Analogues, Organic Lett., 2001, pp. 3237-3239, vol. 3, Iss. 21.

Sabbadini et al., Sphingosine is endogenous to cardiac and skeletal muscle, Biochem. Biophys. Res. Comm., 1993, pp. 752-758, vol. 193, Iss. 2.

Sabbadini et al., The Mirf trial: predicting the incidence and severity of CAD using serum sphingolipids, Circulation, 2000, p. II699, vol. 102, Iss. 18 Suppl.

Saito et al., Absolute Configuration of Scyphostatin, Organic Letts, 2000, pp. 505-506, vol. 2, Iss. 4.

Sakai et al., A devise for recording left ventricular contraction and electrocardiogram in nonworking isolated perfused rat heart, Jpn J. Pharmacol., 1978, pp. 223-229, vol. 28, Iss. 2.

Sato, A new role of lipid receptors in vascular and cardiac morphogenesis, J. Clin. Invest., 2000, pp. 939-940, vol. 106, Iss. 8.

Sawada et al., Ordering of ceramide formation, caspase activation, and Bax/Bcl-2 expression during etoposide-induced apoptosis in C6 glioma cells, Cell Death Differ., 2000, pp. 761-772, vol. 7, Iss. 9.

Sawai et al., Function of the Cloned Putative Neutral Sphingomyelinase as Lyso-platelet Activating FactorPhospholipase C, J. Biol. Chem., 1999, pp. 38131-38139, vol. 274, Iss. 53.

Sawai et al., Identification of ISC1 (YER019w) as Inositol Phosphosphingolipid Phospholipase C Saccharomyces cerevisiae, J. Biol. Chem., 2000, pp. 39793-39798, vol. 275, Iss. 50.

Schissel et al., Zn2+-stimulated Sphingomyelinase Is Secreted by Many Cell Types and Is a Product of the Acid Sphingomyelinase Gene, J. Biol. Chem., 1996, pp. 18431-18436, vol. 271, Iss. 31.

Sergeyev et al., Lipid Spectrum of the Myocardium of White Rats Exposed to Hypoxic Hypoxia, Kosm. Biol. Aviakosm. Med. (Russian), 1981, pp. 71-74, vol. 15, Iss. 6 (English Translation pp. 104-108).

Shayman et al., Glucosylceramide Synthase: Assay and Properties, Methods Enzymol., 1999, pp. 42-49, vol. 311.

Shayman et al., Inhibitors of Glucosylceramide Synthase, Methods Enzymol., 1999, pp. 373-387, vol. 311.

Shinghal et al., Ceramide 1-Phosphate Phosphatase Activity in Brain, J. Neurochem., 1993, pp. 2279-2285, vol. 61, Iss. 6.

Siehler et al., Sphingosine 1-Phosphate Activates Nuclear Factor-kappa B through Edg Receptors: Activation Through Edg-3 and Edg-5, but not Edg-1, in Human Embryonic Kidney 293 Cells, J. Biol. Chem., 2001, pp. 48733-48739, vol. 276, Iss. 52.

(56) References Cited

OTHER PUBLICATIONS

Siess et al., Lysophosphatidic Acid and Sphingosine 1-Phosphate: Two Lipid Villains Provoking Cardiovascular Diseases?, IUBMB Life, 2000, pp. 161-171, vol. 49, Iss. 3.

Yu et al., Picotal role for acidic sphingomyelinase in cerebral ischemia-induced ceramide and cytokine production, and neuronal apoptosis, J. Mol. Neurosci., 2000, pp. 85-97, vol. 15, Iss. 2.

Zager et al., Decreased expression of mitochondrial-derived H2O2 and hydroxyl radical in cytoresistant proximal tubules, Kidney Int., 1997, pp. 942-952, vol. 52, Iss. 4.

Zechner et al., MKK6 inhibits myocardial cell apoptosis via a p38 MAP kinase-dependent pathway, J. Biol. Chem., 1998, pp. 8232-8239, vol. 273, Iss. 14.

Zelinski et al., Phosphatidylcholine biosynthesis in isolated hamster heart, J. Biol. Chem., 1980, pp. 11423-11428, vol. 255, Iss. 23.

Zhang et al., Comparative analysis of three murine G-protein coupled receptors activated by sphingosine-1-phosphate, Gene, 1999, pp. 89-99, vol. 227, Iss. 1.

Zhang et al., Human Acid Ceramidase Gene: Novel Mutations in Farber Disease, Mol. Genet. Metab., 2000, pp. 301-309, vol. 70, Iss. 4.

Zhou et al., Identification of the First Mammalian Sphingosine Phosphate Lyase Gene and its Functional Expression in Yeast, Biochem. Biophys. Res. Comm., 1998, pp. 502-507, vol. 242, Iss. 3.

Zweerink et al., Characterization of a Novel, Potent, and Specific Inhibitor of Serine Palmitoyltransferase, J. Biol. Chem., 1992, pp. 25032-25038, vol. 267, Iss. 35.

Kihara et al., Direct Measurement of Changes in Intercellular Calcium Transients During Hypoxia, Ischemia, and Reperfusion of the Intact Mammalian Heart, Circ. Res., 1989, pp. 1029-1044, vol. 65, Iss. 4.

Kimura et al., Two Novel Xenopus Homologs of Mammalian LPA1/EDG-2 Function as Lysophosphatidic Acid Receptors in Xenopus Oocytes and Mammalian Cells, J. Biol. Chem., 2001, pp. 15208-15215, vol. 276, Iss. 18.

Kita et al., Reverse hydrolysis reaction of a recombinant alkaline ceramidase of Pseudomonas aeruginosa, Biochim. Biophys. Acta, 2000, pp. 111-120, vol. 1485, Iss. 2-3.

Kohama et al., Molecular cloning and functional characterization of murine sphingosine kinase, J. Biol. Chem., 1998, pp. 23722-23728, vol. 273, Iss. 37.

Kolesnick, The thereapeutic potential of modulating the ceramide/sphingomyelin pathway, J. Clin. Inv., 2002, pp. 3-8, vol. 110, Iss. 1.

Kolesnick et al., Characterization of a Ceramide Kinase Activity from Human Leukemia (HL-60) Cells: Separation From Diacylglycerol Kinase Activity, J. Biol. Chem., 1990, pp. 18803-18808, vol. 265, Iss. 31.

Krown et al., Tumor necrosis factor alpha-induced apoptosis in cardiac myocytes. Involvement of the sphingolipid signaling cascade in cardiac cell death, J. Clin. Invest., 1996, pp. 2854-2865, vol. 98, Iss. 12.

Kubota et al., Accumulation of ceramide in ischemic human brain of an acute case of cerebral occlusion, Japan J. Exp. Med., 1989, pp. 59-64, vol. 59, Iss. 2.

Kubota et al., Sphingomyelin changes in rat cerebral cortex during focal ischemia, Neurol. Res., 1996, pp. 337-341, vol. 18, Iss. 4.

Lanterman et al., Characterization of sphingosine kinase (SK) activity in Saccharomyces cerevisiae and isolation of SK-deficient mutants, Biochem. J., 1998, pp. 525-531, vol. 332, Pt. 2.

Lee et al., Cell-cycle-dependent changes in ceramide levels preceding retinoblastoma protein dephosphorylation in G2/M, Biochem. J., 1998, pp. 457-461, vol. 334, Pt. 2.

Lee et al., Effect of Ischemia on Calcium-Dependent Fluorescence Transients in Rabbit Hearts Containing Indo 1. Correlation with Monophasic Action Potentials and Contraction, Circ., 1988, pp. 1047-1051, vol. 78 Iss. 4.

Lee et al., Improved Inhibitors of Glucosylceramide Synthase, J. Bio. Chem., 1999, pp. 14662-14669, vol. 274, Iss. 21.

Lee et al., Sphingosine 1-Phosphate Induces Angiogenesis: Its Angiogenic Action and Signaling Mechanism in Human Umbilical Endothelial Cells, Biochem. Biophys. Res. Commun., 1999, pp. 743-755, vol. 264, Iss. 3.

Lee et al., Lysophosphatidic acid and sphingosine 1-phosphate stimulate endothelial cell wound healing, Am. J. Physiol. Cell Physiol., 2000, pp. C612-C618, vol. 278, Iss. 3.

Levade, et al., Sphingomyelinases and Niemann-Pick disease, J. Clin. Chem. Clin. Biochem., 1986, pp. 205-220, vol. 24, Iss. 4.

Li et al., The Human Acid Ceramidase Genes (ASAH): Structure, Chromosomal Location, Mutation Analysis, and Expression, Genomics, 1999, pp. 223-231, vol. 62, Iss. 2.

Liliom et al., Sphingosylphosphocholine is a naturally occurring lipid mediator in blood plasma: a possible role in regulating cardiac function via sphingolipid receptors, Biochem. J., 2001, pp. 189-197, vol. 355, Pt. 1.

Lin et al., Identification of neutral and acidic sphingomyelinases in Helicobacter pylori, FEBS Lett., 1998, pp. 249-253, vol. 423, Iss. 2.

Linn et al., Regulation of de novo sphingolipid biosynthesis and the toxic consequences of its disruption, Biochem. Soc., 2001, pp. 831-835, vol. 29, Pt. 6.

Lister et al., Interaction of sphingomyelinase with sphingomyelin analogs modified at the G1 and C-3 positions of the sphingosine backbone, Biochim. Biophys. Acta, 1995, pp. 25-30, vol. 1256, Iss. 1.

Little at al, Surface display of antibodies, Biotechn. Adv., 1994, pp. 539-555, vol. 12, Iss. 3.

Liu et al., Inhibition of the neutral magnesium-dependent sphingomyelinase by glutathione, J. Biol. Chem., 1997, pp. 16281-16287, vol. 272, Iss. 26.

Liu et al., Glutathione regulation of neutral sphingomyelinase in tumor necrosis factor-alpha-induced cell death, J. Biol. Chem., 1998, pp. 11313-11320, vol. 273, Iss. 18.

Liu et al., Advances in the signal transduction of ceramide and related sphingolipids, Crit. Rev. Clin. Lab. Sci., 1999, pp. 511-573, vol. 36, Iss. 6.

Liu et al., Purification and Characterization of a Membrane Bound Neutral pH Optimum Magnesium-dependent and Phosphatidylserine-stimulated Sphingomyelinase from Rat Brain, J. Biol. Chem., 1998, pp. 34472-34479, vol. 273, Iss. 51.

Liu et al., Molecular Cloning and Functional Characterization of a Novel Mammalian Sphingosine Kinase Type 2 Isoform, J. Biol. Chem., 2000, pp. 19513-19520, vol. 275, Iss. 26.

Liu et al., Sphingomyelinase Assay Using Radiolabeled Substrate, Meth. Enzymol., 2000, pp. 164-167, vol. 311.

Lochhead at al, Fluorinated anesthetic exposure activates the renal cortical sphingomyelinase cascade, Kidney Int., 1998, pp. 373-381, vol. 54, Iss. 2.

Luberto et al., Sphingomyelin synthase, a potential regulator of intracellular levels of ceramide and diacylglycerol during SV40 transformation. Does sphingomyelin synthase account for the putative phosphatidylcholine-specific phospholipase C?, J. Biol. Chem., 1998, pp. 14550-14559, vol. 273, Iss. 23.

Luberto at al., Sphingolipid Metabolism in the Regulation of Bioactive Molecules, Lipids, 1999, S5-S11, vol. 34, Supp. 1.

Lynch at al., Life on the edg, Trends Pharmacol. Sci., 1999, pp. 473-475, vol. 20, Iss. 12.

Magnelli et al., BCL-2 Overexpression Abolishes Early Calcium Waving Preceding Apoptosis in NIH-3T3 Murine, Biochem. Biophys. Res. Comm., 1994, pp. 84-90, vol. 204, Iss. 1.

Mandala et al., Inhibition of Serine Palmitoyl-Transferase Activity by Lipdxamycin, J. Antibiot. (Tokyo), 1994, pp. 376-379, vol. 47, Iss. 3.

Mandala et al., The Discovery of Australifungin, a novel Inhibitor of Sphinganine N-Acyltransferase from Sporormiella australis. Producing Organism, Fermentation, Isolation, and Biological Activity, J. Antibiot. (Tokyo), 1995, pp. 349-356, vol. 48, Iss. 5.

Mandala et al., Khafrefungin, a novel inhibitor of sphingolipid synthesis, J. Biol. Chem., 1997, pp. 32709-32714, vol. 272, Iss. 51.

Mandala et al., Viridiofungins, Novel Inhibitors of Sphingolipid Synthesis, J. Antibiot. (Tokyo), 1997, pp. 339-343, vol. 50, Iss. 4.

Mandala et al., Sphingoid base 1-phosphate phosphatase: a key regulator of sphingolipid metabolism and stress response, Proc. Natl. Acad. Sci. USA, 1998, pp. 150-155, vol. 95, Iss. 1.

(56) References Cited

OTHER PUBLICATIONS

Mandala et al., Isolation and Characterization of Novel Inhibitors of Sphingolipid Synthesis: Australifungin, Viridiofungins, Rustmicin, and Khafrefungin, Methods Enzymol., 1999, pp. 335-348, vol. 311.
Mandala et al., Molecular cloning and characterization of a lipid phosphohydrolase that degrades sphingosine-1-phosphate and induces cell death, Proc. Natl. Acad. Sci. USA, 2000, pp. 7859-7864, vol. 97, Iss. 14.
Mandala et al., Sphingosine-1-Phosphate Phosphatases, Prostaglandins Other Lipid Mediat., 2001, pp. 143-156, vol. 64, Iss.1-4.
Mao et al., Molecular cloning and characterization of SCaMPER, a Sphingolipid Ca2+ release-mediating protein from endoplasmic reticulum, Proc. Natl. Acad. Sci. USA, 1996, pp. 1993-1996, vol. 93, Iss. 5.
Mao et al., Cloning of an Alkaline Ceramidase from Saccharomyces cerevisiae: An Enzyme with Reverse (CoA-Independent) Ceramide Synthase Activity, J. Biol. Chem., 2000, pp. 6876-6884, vol. 275, Iss. 10.
Mao et al., Cloning and Characterization of a Saccharomyces cerevisiae Alkaliine Ceramidase with Specificity for Dihydroceramide, J. Biol. Chem., 2000, pp. 31369-31378, vol. 275, Iss. 40.
Mao et al., Cloning and Characterization of a Novel Human Alkaline Ceramidase: A Mammalian Enzyme That Hydrolyzes Phytoceramide, J. Biol. Chem., 2001, pp. 26577-26588, vol. 276, Iss. 28.
Marks et al., Methods for Studying Glucosylceramide Synthase, Methods Enzymol., 1999, pp. 50-59, vol. 311.
Martin et al., Neutral Magnesium-Dependent Sphingomyelinase from Liver Plasma Membrane: Purification and Inhibition by Ubiquinol, J. Bioenerg. Biomember., 2001, pp. 143-153, vol. 33, Iss. 2.
Meacci et al., Receptor-mediated activation of phospholipase D by sphingosine 1-phosphate in skeletal muscle C2C12 cells: A role for protein kinase C, FEBS Lett., 1999, pp. 184-188, vol. 457, Iss. 2.
Meldrum, Tumor necrosis factor in the heart, Am. J. Physiol., 1998, pp. R577-R595, vol. 274, Iss. 3.
Melendez et al., Human sphingosine kinase: molecular cloning, functional characterization and tissue distribution, Gene, 2000, pp. 19-26, vol. 251, Iss. 1.
Abe et al., Structural and stereochemical studies of potent inhibitors and glucosylceramide synthase and tumor cell growth, J. Lipid Res., 1995, pp. 611-621, vol. 36, Iss. 3.
Abe et al., Glycosphingolipid depletion in Fabry disease lymphoblasts with potent inhibitors of glucosylceramide synthase, Kidney Int., 2000, pp. 446-454, vol. 57, Iss. 2.
Abe et al., Use of Sulfobutyl Ether-Cyclodextrin as a Vehicle for D-threo-1-Phenyl-2- decanoylamino-3-morpholinopropanol—Related Glucosylceramide Synthase Inhibitors, Anal. Biochem., 2000, pp. 344-347, vol. 287, Iss. 2.
Ambati, Age-related macular degeneration: etiology, pathogenesis, and therapeutic strategies, Surv. Ophthalmol., 2003, pp. 257-293, vol. 48, Iss. 3.
An et al., Identification of cDNAs encoding two G protein-coupled receptors for lysosphingolipids, FEBS Letts., 1997, pp. 279-282, vol. 417, Iss. 3.
An et al., Characterization of a Novel Subtype of Human G Protein-coupled Receptor for Lysophosphotatidic Acid, J. Biol. Chem., 1998, pp. 7906-7910, vol. 273, Iss. 14.
An et al., Sphingosine 1-phosphate-induced cell proliferation, survival, and related signaling events mediated by G protein-coupled receptors Edg3 and Edg5, J. Biol. Chem., 2000, pp. 288-296, vol. 275, Iss. 1.
Ancellin et al., Extracelluar export of sphingosine kinase-1 enzyme: Sphingosine 1 phosphate generation and the induction of angiogenic vascular maturation, J. Biol. Chem., 2001, pp. 6667-6675, vol. 277, Iss. 8.

Andrieu-Abadie et al., L-carnitine prevents doxorubicin-induced apoptosis of cardiac myocytes: role of inhibition of ceramide generation, FASEB J., 1999, pp. 1501-1510, vol. 13, Iss. 12.
Arenz et al., Synthese des ersten selektiven irreverilben Inhibitors der neutralen Sphingomyelinase, Angew Chem., 2000, pp. 1498-1500, vol. 112 (German); Synthesis of the First Selective Irreversible Inhibitor of Neutral Sphingomyelinase, Angew. Chem. Int. Ed., 2000, pp. 1440-1442, vol. 39, Iss. 8 (English Equivalent).
Arenz et al., Manumycin A and its Analogues Are Irreversible Inhibitors of Neutral Sphingomyelinase, Chem. Biochem., 2001, pp. 141-143, vol. 2, Iss. 2.
Arenz et al., Synthesis and Biochemical Investigation of Scyphostatin Analogues as Inhibitors of Neutral Sphingomyelinase, Bioorg. Medicinal Chem., 2001, pp. 2901-2904, vol. 9, Iss. 11.
Arenz et al., Synthesis of the First Selective Irreversible Inhibitor of Neutral Sphingomyelinase, Eur. J. Org. Chem., 2001, pp. 137-140, vol. 2001, Iss.1.
Ariga et al., Role of Sphingolipid-mediated cell death in neurodegenerative diseases, J. Lip. Res., 1998, pp. 1-16, vol. 39, Iss. 1.
Bajjalieh et al., Ceramide Kinase, Methods Enzymol. 311:207-215 (1999).
Barbone et al., Robotic Assay of Sphingomyelinase Activity for High Throughput Screening, Meth. Enzymol., 1999, pp. 168-176, vol. 311.
Bawab et al., Molecular Clonging and Characterization of a Human Mitochondrial Ceramidase, J. Biol. Chem., 2000, 21508-21513, vol. 275, Iss. 28.
Bernardo et al., Purification and Characterization of Magnesium-dependent Neutral Sphingomyelinase from Bovine Brain, J. Biol. Chem., 2000, pp. 7641-7647, vol. 275, Iss. 11.
Betto et al., Sphingosylphosphocholine modulates the ryanodine receptor/calcium-release channel of cardiac sarcoplasmic reticulum memberances, Biochem. J., 1997, pp. 327-333, vol. 322, Iss. 1.
Bielawska et al., (1S,2R)-D-erhthro-2-(N-My-ristoylamino)-1-phenyl-1-propanol as an Inhibitor of Ceramidase, J. Biol. Chem., 1996, pp. 12646-12654, vol. 271, Iss. 21.
Bielawska et al., Ceramide Is Involved in Triggering of Cardiomyocyte Apoptosis Induced by Ischemia and Reperfusion, Am. J. Pathol., 1997, pp. 1257-1263, vol. 151, Iss. 5.
Boudker et al., Detection and Characterization of Ceramide-1-phosphate Phosphatase Activity in Rat Liver Plasma Membrane, J. Biol. Chem., 1993, pp. 22150-22155, vol. 268, Iss. 29.
Brady et al., The metabolism of sphingomyelin. II. Evidence of an enzymatic deficiency in Niemann-Pick disease, Proc. Natl. Acad. Sci. USA, 1966, pp. 366-369, vol. 55, Iss. 2.
Brindley et al., Analysis of Ceramide 1-phosphate and Sphingosine-1-phosphate Phosphatase Activities, Methods Enzymol., 1999, pp. 233-244, vol. 311.
Brownlee, Intracellular signalling: sphingosine-1-phosphate branches out, Current Biol., R535-R538, 2001, vol. 11, Iss. 13.
Burton et al., Human antibodies from combinatorial libraries, Adv. Immunol., 1994, pp. 191-280, vol. 57.
Byers, What can randomized control trials tell us about nutrition and cancer prevention?, CA Canc. J., 1999, pp. 353-361, vol. 49, Iss. 6.
Cain et al., Therapeutic Strategies to Reduce TNF-a Mediated Cardiac Contractile Depression Following Ischemia and Reperfusion, J. Mol. Cell. Cardiol., 1999, pp. 931-947, vol. 31, Iss. 5.
Caligan et al., A High-Performance Liquid Chromatographic Method to Measure Sphingosine 1-Phosphate and Related Compounds from Sphingosine Kinase Assays and Other Biological Samples, Anal. Biochem., 2000, pp. 36-44, vol. 281, Iss. 1.
Chan et al., Ceramide Path in Human Lung Cell Death, Am. J. Respir. Cell Mol. Biol., 2000, pp. 460-468, vol. 22, Iss. 4.
Chan et al., Purification and Characterization of Neutral Sphingomyelinase from Helicobacter pylori, Biochemistry, 2000, pp. 4838-4845, vol. 39, Iss. 16.
Chatterjee, Neutral Sphingomyelinase, Adv. Lip. Res., 1993, pp. 25-48, vol. 26.
Chatterjee, Sphingolipids in Atherosclerosis and Vascular Biology, Arterioscler. Throm. Vasc. Biol., 1998, pp. 1523-1533, vol. 18, Iss. 10.

(56) References Cited

OTHER PUBLICATIONS

Chatterjee et al., Molecular Cloning, Characterization, and Expression of a Novel Human Neutral Sphingomyelinase, J. Biol. Chem., 1999, pp. 37407-37412, vol. 274, Iss. 52.
Chatterjee, Neutral Sphingomyelinase: past, present, and future, Chem. Phys. Lipids, 1999, pp. 79-96, vol. 102, Iss. 1.
Chau et al., Synthesis of Simple Aryl Neutral Sphingomyelinase Inhibitors, 221st ACS Natl. Mtg., San Diego, CA, USA, 2001, Am. Chem. Soc. (Abstract Only).
Chun, Lysophospholipid receptors: implications for neural signaling, Crit. Rev. Neuro., 1999, pp. 151-168, vol. 13, Iss. 2 (Abstract Only).
Chun et al., A Growing Family of Receptor Genes for Lysophosphatidic Acid (LPA) and other Lysophospholipids (LPs), Cell Biochem. Biophys., 1999, pp. 213-242, vol. 30, Iss. 2.
Cordis et al., HPTLC analysis of sphingomylein, ceramide and sphingosine in ischemic/reperfused rat heart, J. Pharm. Biomed. Anal., 1998, pp. 1189-1193, vol. 16, Iss. 7.
Cuvlilier et al., Suppression of ceramide-mediated programmed cell death by sphingosine-1-phosphate, Nature, 1996, pp. 800-803, vol. 381, No. 6585.
Dickson et al., Serine Palmitoyltransferase, Methods Enzymol., 1999, pp. 3-9, vol. 311.
Edsall et al., N, N-Dimethylsphingosine is a potent competitive inhibitor of sphingosine kinase but not of protein kinase C: modulation of cellular levels of sphingosine 1-phosphate and ceramide, Biochem., 1998, pp. 12892-12898, vol. 37, Iss. 37.
Edson et al., The Aminoglycosides, Mayo Clin. Proc., 1999, pp. 519-528, vol. 74, Iss. 5.
Eichler et al., Peptide, peptidomimetic, and organic synthetic combinatorial libraries, Med. Res. Rev., 1995, pp. 481-496, vol. 15, Iss. 6 (Abstract Only).
Fensome et al., A Neutral Magnesium-dependent Sphingomyelinase Isoform Associated with Intracellular Membranes and Reversibly Inhibited by Reactive Oxygen Species, J. Biol. Chem., 2000, pp. 1128-1136, vol. 275, Iss. 2.
Fujii et al., Mg2+ binding and catalytic function of sphingomyelinase from Bacillus cereus, J. Biochem (Tokyo), 1998, pp. 1178-1187, vol. 124, Iss. 6.
Fukushima et al., A single receptor encoded by vzg-1/IpA1/edg-2 couples to G proteins and mediates multiple cellular responses to lysophosphatidic acid, Proc. Natl. Acad. Sci. USA, 1998, pp. 6151-6156, vol. 95, Iss. 11.
Furneisen et al., Enzymological properties of the LPP1-encoded lipid phosphatase from Saccharomyces cerevisiae, Biochim. Biophys. Acta, 2000, pp. 71-82, vol. 1484, Iss. 1.
Garcia-Ruiz, Human placenta sphingomyelinase, an exogenous acidic pH-optimum sphingomyelinase, induces oxidative stress, glutathione depletion, and apoptosis in rat hepatocytes, Hepatology, 2000, pp. 56-65, vol. 32, Iss. 1.
Gates et al., Serum amyloid p component: its role in platelet activation stimulated by sphingomyelinase d purified from the venom of the brown recluse spider (*Loxosceles reclusa*), Toxicon., 1990, pp. 1303-1315, vol. 28, Iss. 11.
Anliker et al., J. Biol. Chem., 2001, 20555-20558, 279(20).
Lebrun-Julien et al., Invest. Opthalamol. Vis. Sci., 2005, 46(5), E-Abstract 1319.
Mills, DTIC [online], 2006, 1-17, 125-138.
Pyne et al., Biochem. J., 2000, 385-402, 349(Pt. 2).
Svetlov et al., Biochim. Biophys. Acta, 2002, 251-256, 1582(1-3).
Thoreson et al., Invest. Opthalamol. Vis. Sci., 2002, 2450-2461, 43(7).
Yadav et al., Tetrahedron Lett., 2003, 2983-2985, 44(14).
Chen et al., Anal. Chem. 2000, 2949-2956, 72(13).
Visentin et al., Cancer Cell., 2006, 225-238, 9(3).
Kohler et al., Nature, 1975, 495-497, 256(5517).
Kotani et al., New Engl. J. Med., 2000, 1514-1519, 343(21).
Krishnamurthy et al., J. Lipid Res., 2007, 968-975, 48(4).
Lagerqvist et al., Br. Heart J., 1992, 282-285, 68(9).
Lam et al., J. Pharm. Sci., 1997, 1250-1255, 86(11).
Larson et al., Cytometry, 2000, 203-208, 41(3).
Lee et al., Cancer Res., 2006, 2740-2748, 66(5).
Leung et al., J. Neuroinflamm., 2010, 27, 7(1).
Luster et al., J. Biol. Chem., 2006, 29863-29871, 281(40).
Ma et al., J. Pharmacol. Exp. Ther., 2010, 540-546, 333(2).
MacEyka et al., Biochim. Biophys. Acta, 2002, 192-201, 1585(2-3).
Maneta-Peyret et al., J. Immunol. Methods, 1988, 123-127, 108(1-2).
Maneta-Peyret et al., J. Immunol. Methods, 1989, 155-159, 122(2).
Marks et al., J. Mol. Biol., 1991, 581-597, 222(3).
Matsumoto et al., Rheumatol. Int., 2006, 1096-1100, 26(12).
Matteo et al., Proc. Ann. Meeting Am. Assoc. Canc. Res., 2007, 971, 48.
Millan, Prog. Neurobiol., 1999, 1-164, 57(1).
Mills et al., Nat. Rev. Cancer, 2003, 582-591, 3(8).
Moolenaar, Exp. Cell Res., 1999, 230-238, 253(1).
Moolenaar et al., BioEssays, 2004, 870-881, 26(8).
Morrison et al., Proc. Natl. Acad. Sci. USA, 1984, 6851-6855, 81(21).
Moulin, Pain Res. Manag., 2006, 30A-36A, 11(Suppl. A).
Mueller et al., Nat. Rev. Drug Discov., 2005, 387-398, 4(5).
Murphy et al. (Ed.), Janeway's Immunobiology, Fifth Edition, 2001, Garland Publishing, London, UK (Electronic Table of Contents Only).
Myers et al., Drug Disc. Today, (2006), 8-20, 11(1-2).
Nolli et al., Ann. 1st Super Sanita, 1991, 149-154, 27(1).
Ohlsson et al., Tetrahedron, 2000, 9975-9984, 56(51).
Polomano et al., Pain, 2001, 293-304, 94(3).
Presta, Curr. Opin. Struct. Biol., 1992, 593-596, 2(4).
Queen et al., Proc. Natl. Acad. Sci. USA, 1989, 10029-10033, 86(24).
Ramakers et al., Exp. Cell Res., 1998, 252-262, 245(2).
Ramer et al. J. Neurosci., 2004, 10796-10805, 24(48).
Ran et al., Clin. Cancer Res., 2005, 1551-1562, 11(4).
1990 Remington's Pharmaceutical Sciences 16th edition (1990) (Table of Contents).
Riechmann et al., Nature, 1988, 323-329, 332(6162).
Scherer et al., Cardiovasc. Res., 2006, 79-87, 70(1).
Schousboe, Biochim. Biophys. Acta, 1979, 396-408, 579(2).
Seltzer et al., Pain, 1990, 205-218, 43(2).
Shen et al., Gynecol. Oncol., 2001, 25-30, 83(1).
Simard et al., Nat. Med., 2006, 433-440, 12(4).
Simon et al., J. Biol. Chem., 2005, 14656-14662, 280(15).
Spiegel et al., Leukemia, 2002, 1596-1602, 16(9).
Spiegel et al., Nat. Rev. Mol. Cell Biol., 2003, 397-407, 4(5).
Suomalainen et al., Am. J. Pathol., 2005, 773-781, 166(3).
Sutcliffe et al., Proc. Natl. Acad. Sci. USA, 2000, 1976-1981, 97(5).
Sutphen, Cancer Epidemiol. Biomarkers Prev., 2004, 1185-1191, 13(7).
Tamamura et al., Jpn. J. Exp. Med., 1971, 31-38, 41(1).
Tigyi et al., J. Biol. Chem., 1992, 21360-21367, 267(30).
Tomii et al., Jpn J. Med. Sci. Biol., 1991, 75-80, 44(2).
Ueda, Pharmacol. Ther., 2006, 57-77, 109(1-2).
Umeda et al., J. Mol. Biol., 1989, 601-614, 208(4).
Van Leeuwen et al., Biochem. Soc. Trans., 2003, 1209-1212, 31(6).
Vaswani et al., Ann. Allergy Asthma Immunol., 1998, 105-119, 81(2).
Vemuri et al., Lepr. Rev., 1996, 95-103, 67(2).
Vielhaber et al., Glycobiology, 2001, 451-457, 11(6).
Weiner et al., J. Neurosci., 2001, 7069-7078, 21(18).
Wu, Methods, 2005, 1-2, 36(1).
Wu et al., Endocrinology, 2005, 3387-3400, 146(8).
Xiao et al., Anal. Biochem., 2001, 302-313, 29(2).
Xu et al., Cytokine, 1997, 1028-1033, 9(12).
Xu et al., JAMA, 1998, 719-723, 280(8).
Yuan et al. Nat. Cell Biol., 2003, 38-45, 5(1).
Zapata et al., Protein Eng., 1995, 1057-1062, 8(10).
Zwaal et al., Blood, 1997, 1121-1132, 89(4).
Adzick et al., Ann. Surg., 1994, 10-18, 220(1).
Arruda et al., Brain Res., 2000, 216-225, 879(1-2).
Baker et al., Anal. Biochem., 2001, 287-295, 292(2).
Banerji et al., Biochem. Cell Biol., 1990, 96-101, 68(1).
Baranauskas et al., Prog. Neurobiol., 1998, 349-365, 54(3).
Baudhuin et al., FASEB J., 2004, 341-343, 18(2).
Berge et al., J. Pharm. Sci., 1977, 1-19, 66(1).
Brazma et al., FEBS Lett., 2000, 17-24, 480(1).

(56) References Cited

OTHER PUBLICATIONS

Brindley, J. Cell. Biochem., 2004, 900-912, 92(5).
Calcutt et al., Anesthesiology, 2000, 1271-1278, 93(5).
Carmeliet, Nature, 2005, 932-936, 438(7070).
Celts et al., FEBS Lett., 2000, 2-16, 480(1).
Chen et al., Lipid Mediat., 2005, 65-76, 77(1-4).
Chintalacharuvu et al., Methods, 1995, 73-82, 8.
Chothia et al., J. Mol. Biol., 1985, 651-663, 186(3).
Chothia et al., J. Mol. Biol., 1987, 901-917, 196(4).
Chun et al, Curr. Pharm. Des., 2006, 161-171, 12(2).
Clackson et al., Nature, 1991, 624-628, 352(6336).
Coderre et al., J. Neurosci, 1992, 3665-3670, 12(9).
Coyle et al., Chem. Mater., 1989, 606-611, 1(6).
Desgeorges et al., J. Rheumatol., 1997, 1510-1516, 24(8).
Deutschman et al., Am. Heart J., 2003, 62-68, 146(1).
Diaz et al., Bioconjug. Chem., 1998, 250-254, 9(2).
Dubner et al., Trends Neurosci., 1992, 96-103, 15(3).
Fabianowski et al., Langmuir, 1989, 35-41, 5(1).
Fang et al., Biochim. Biophys. Acta, 2002, 257-264, 1582(1-3).
Flatters et al., Pain, 2006, 245-257, 122(3).
French et al., Cancer Res., 2003, 5962-5969, 63(18).
Fujita et al., Neurochem. Int. 2007, 351-355, 50(2).
Fujiwara et al., J. Biol. Chem., 2005, 35038-35050, 280(41).
Fukushima et al., Dev Biol., 2000, 6-18, 228(1).
Fukushima et al., Neurochem. Int., 2007, 302-307, 50(2).
Gardell et al., Trends Mol. Med., 2006, 65-75, 12(2).
George et al., Pain, 2000, 267-275, 88(3).
Goetzl et al., Scientific World J., 2002, 324-338, 2.
Goetzl et al., J. Clin. Invest., 2004, 1531-1537, 114(11).
Hargreaves et al., Pain, 1988, 77-88, 32(1).
Holliger et al., Proc. Natl. Acad. Sci. USA, 1993, 6444-6448, 90(14).
Huang et al., Cancer Res., 2005, 4408-4416, 65(10).
Igarashi et al., Proc. Natl. Acad. Sci. USA, 2003, 10664-10669, 100(19).
Inoue et al., Nat. Med., 2004, 712-718, 10(7).
Inoue et al., J. Neurochem., 2008, 1556-1565, 107(6).
Jalink et al., Cell Growth Differ., 1993, 247-255, 4(4).
Jin et al., Exp. Neurol., 2008, 229-237, 210(1).
Jolivalt et al., Pain, 2006, 14-21, 121(1-2).
Jones et al., Nature, 1986, 522-525, 321(6069).
Jozwiak et al., Eur. J. Cancer Clin. Oncol., 1982, 617-621, 18(7).
Kabat, Pharmacol. Rev., 1982, 23-38, 34(1).
Khachigan, Circ. Res., 2006, 186-191, 98(2).
Kingsbury et al., Nat. Neurosci., 2003, 1292-1299, 6(12).
Qian, Molecular Design and Chemical Synthesis of Affinity Probes for Lysophosphatadic Acid Receptors, Dissertation U. of Utah, 2004, 1-131.
Chen et al., Production and Application of LPA Polyclonal Antibody, Bioorg. Med. Chem. Lett., 2000, 1691-1693, 10 (15).

\* cited by examiner

Synthesis of Typical Thiolated S1P-Related Antigen

Synthesis of Typical Thiolated S1P-Related Antigen (Continued)

Synthesis of Typical Thiolated S1P-Related Antigen (Continued)

Synthesis of Typical Protected Thiolated Fatty Acid

Synthesis of Typical Thiolated Fatty Acid

Synthesis of Typical Thiolated LPA Hapten

Synthesis of Typical Thiolated LPA Hapten (Continued)

Figure 6

V$_H$
QAHLQQSDAELVKPGASVKISCKVSGFIFI DH
TIH WMKQRPEQGLEWIG CISPRHDITKYNEM
FRG KATLTADKSSTTAYIQVNSLTFEDSAVYF
CAR GGFYGSTIWFDF WGQGTTLTVS

V$_L$
ETTVTQSPASLSMAIGEKVTIRC ITTTDIDDDM
N WFQQKPGEPPNLLIS EGNILRP GVPSRFSS
SGYGTDFLFTIENMLSEDVADYYC LQSDNLP
FT FGSGTKLEIK

FIG. 7A pATH50: Nucleotide Sequence: Chimeric Light Chain (SEQ ID NO:42; = nucl. 15-403 of SEQ ID NO:16)

```
 15  atgattgcct ctgcactgt cttgtctc ctgttgctct gtttttcaagg taccagatgt gaaacaactg tgaccagtc tccagcatcc ctgtccatgg
     ‾‾‾‾‾‾‾‾‾‾ ‾‾‾‾‾‾‾‾‾‾ ‾‾‾‾‾‾‾‾‾‾ ‾‾‾‾‾‾‾‾‾‾ ‾‾‾‾‾‾‾‾‾‾                                    ‾‾‾‾‾‾‾‾‾‾
            Leader                                                                                 FW1
     >>..........Sphingomab Chimeric Light Chain..........>

115  ctataggaga aaaagtcacc atcagatgca taaccaccac tgatattgat gatgatatga actggttcca gcagaagcca gggaacctc ctaacctcct
                                                ‾‾‾‾‾‾‾‾‾‾ ‾‾‾‾‾‾‾‾‾‾ ‾‾‾‾‾‾‾‾‾‾                              
                                                       CDR1                                FW2
     >..........Sphingomab Chimeric Light Chain..........>

215  tatttccgaa ggcaatattc ttcgtcctgg agtcccatcc cgattctcca gcagtggcta tggtacagac tttcttttta caattgaaaa catgctctca
     ‾‾‾‾‾‾‾‾‾‾ ‾‾‾‾‾‾‾‾‾‾                                                                                     
           CDR2                                                        FW3
     >..........Sphingomab Chimeric Light Chain..........>

315  gaagatgttg cagattacta ctgtttgcag agtgataact taccattcac gttcggctcg gggacaaagt tggaaataaa acgtgagtg
                          ‾‾‾‾‾‾‾‾‾‾ ‾‾‾‾‾‾‾‾‾‾ ‾‾‾‾‾‾‾‾‾‾                                           
                                   CDR3                                FW4
     >..........Sphingomab Chimeric Light Chain..........>>
``` pATH50: Chimeric Light Chain protein sequence (SEQ ID NO: 17)

```
  1  miasaqflgl lllcfqgtrc ettvtqspas lsmaigekvt ircitttdid ddmnwfqqkp geppnllise gnilrpgvps rfsssgygtd flftienmls
101  edvadyyclq sdnlpftfgs gtkleikre
```

Nucleotide alignment of pATH50 plasmid mutations to replace the methionine residue (SEQ ID NOs 16 & 18-21 respectively in order of appearance):

```
pATH50     1 agcttgcgccaccatgattgcctctgcactgtccttgtctctgttgctctgtttcaaggtaccagatgtgaaacaactgtgaccagtctccagc
pATH52C1 416 ................................................................................................
pATH53C1 416 ................................................................................................
pATH54C1 408 ................................................................................................
pATH55C1 408 ................................................................................................

pATH50   101 atccctgtccatggctataggagaaaaagtcaccatcagatgcataaccaccactgatattgatgatgataactgttcagcagaagcagggaa
pATH52C1 516 ..............................................................g.................................
pATH53C1 516 .............................................................c.t.................................
pATH54C1 508 ..............................................................ggt................................
pATH55C1 508 ..............................................................cc.................................
```

FIG. 7B

Protein alignment of pATH50 plasmid mutations to replace the methionine residue (SEQ ID NOs 17 & 22-25 respectively in order of appearance):

```
pATH50   15  miasaqflglllcfqgtrcettvtqspaslsmaigekvtircitttdidddmnwfgqkpgeppnllisegnilrpgvpsrfsssygtdflftienmls
pATH52C1 430 ..............................................................v.................................
pATH53C1 430 ..............................................................l.................................
pATH54C1 422 ..............................................................g.................................
pATH55C1 422 ..............................................................p.................................

pATH50   315 edvadyyclqsdnlpftfgsgtkleikre
pATH52C1 730 ............................
pATH53C1 730 ............................
pATH54C1 722 ............................
pATH55C1 722 ............................
```

FIG. 7C

```
pATH52 [DNA: SEQ ID NO: 43 (=nucl 15-403 of SEQ ID NO: 18); PRT: SEQ ID NO: 22]
430  atgattgcct ctgctcagtt ccttggtctc ctgttgctct gttttcaagg taccagatgt gaaacaactg taccagatcc ctgtcatgg
                leader                                                              FW1
     m  i  a  s  a  q  f  l  g  l  l  l  l  c  f  q  g  t  r  c  e  t  t  v  t  q  s  p  a  s  l  s  m
     >>.........Sphingomab Chimeric Light Chain..................................................^
530  ctatagagaga aaaagtcacc atcagatgca taaccaccac tgatattgat gatgatgtga actggttcca gcagaagcca gggaacctc ctaacctcct
                                                        CDR1                                FW2
     a  i  g  e  k  v  t  i  r  c  i  t  t  d  i  d  d  d  v  n  w  f  q  q  k  p  g  e  p  p  n  l
     >.........Sphingomab Chimeric Light Chain..................................................^
                                      M33V >>>
630  tatttccgaa ggcaatattc ttcgtcctgg agtccccatcc cgattctcca gcagtggcta tggtacagac tttcttttta caattgaaaa catgctctca
         CDR2                                                        FW3
     l  i  s  e  g  n  i  l  r  p  g  v  p  s  r  f  s  s  s  g  y  g  t  d  f  l  f  t  i  e  n  m  l  s
     >.........Sphingomab Chimeric Light Chain..................................................^
730  gaagatgttg cagattacta ctgtttgcag agtgataact taccattcac gttcggctcg gggacaaagt tggaaataaa acgtgagtg
                                  CDR3                                    FW4
     e  d  v  a  d  y  y  c  l  q  s  d  n  l  p  f  t  f  g  s  g  t  k  l  e  i  k  r  e
     >.........Sphingomab Chimeric Light Chain..............^ pATH53 [DNA: SEQ ID NO: 44 (=nucl 15-403 of SEQ ID NO: 19); PRT: SEQ ID NO: 23]
430  atgattgcct ctgctcagtt ccttggtctc ctgttgctct gttttcaagg taccagatgt gaaacaactg taccagatcc ctgtcatgg
                leader                                                              FW1
     m  i  a  s  a  q  f  l  g  l  l  l  l  c  f  q  g  t  r  c  e  t  t  v  t  q  s  p  a  s  l  s  m
     >>.........Sphingomab Chimeric Light Chain..................................................^
530  ctatagagaga aaaagtcacc atcagatgca taaccaccac tgatattgat gatgatctta actggttcca gcagaagcca gggaacctc ctaacctcct
                                                        CDR1                                FW2
     a  i  g  e  k  v  t  i  r  c  i  t  t  d  i  d  d  d  l  n  w  f  q  q  k  p  g  e  p  p  n  l
     >.........Sphingomab Chimeric Light Chain..................................................^
                                      M33L >>>
630  tatttccgaa ggcaatattc ttcgtcctgg agtccccatcc cgattctcca gcagtggcta tggtacagac tttcttttta caattgaaaa catgctctca
         CDR2                                                        FW3
     l  i  s  e  g  n  i  l  r  p  g  v  p  s  r  f  s  s  s  g  y  g  t  d  f  l  f  t  i  e  n  m  l  s
     >.........Sphingomab Chimeric Light Chain..................................................^
730  gaagatgttg cagattacta ctgtttgcag agtgataact taccattcac gttcggctcg gggacaaagt tggaaataaa acgtgagtg
                                  CDR3                                    FW4
     e  d  v  a  d  y  y  c  l  q  s  d  n  l  p  f  t  f  g  s  g  t  k  l  e  i  k  r  e
     >.........Sphingomab Chimeric Light Chain..............^
```

FIG. 7D pATH54 [SEQ ID NO: 45 (=nucl. 15-403 of SEQ ID NO: 20); PRT: SEQ ID NO: 24]
422 atgattgcct ctgctcagtt ccttggtctc ctgtgtctct gtttcaagg. taccagatgt gaaacaactg tgaccagtc tccagcatcc ctgtccatgg
    m   i   a   s   a   q   f   l   g   l   l   c   f   q   g   t   r   c   e   t   t   v   t   q   s   p   a   s   l   s   m
    Leader                                                                                                                FW1
    >>.........Sphingomab Chimeric Light Chain........................................................................>
522 ctataggaga aaagtcacc atcagatgca taaccaccac tgatattgat gatgatggta actgttcca gcagaagca gggaacctc ctaacctcct
    a   i   g   e   k   v   t   i   r   c   i   t   t   d   i   d   d   d   g   n   w   f   q   q   k   p   g   e   p   p   n   l
                                            CDR1                                        FW2
    >.........Sphingomab Chimeric Light Chain........................................................................>
                                            M33G >>>
622 tatttccgaa ggcaatattc ttcgtcctgg agtccatcc cgattctcca gcagtggcta tggtacagac tttctttta caattgaaaa catgctctca
    l   i   s   e   g   n   i   l   r   p   g   v   p   s   r   f   s   s   g   y   g   t   d   f   l   f   t   i   e   n   m   l   s
                CDR2                                                    FW3
    >.........Sphingomab Chimeric Light Chain........................................................................>
722 gaagatgttg cagattacta ctgtttgcag agtgataact taccattcac gttcggctcg gggacaaagt tggaaataaa acgtgagtg
    e   d   v   a   d   y   y   c   l   q   s   d   n   l   p   f   t   f   g   s   g   t   k   l   e   i   k   r   e
                                CDR3                            FW4
    >.........Sphingomab Chimeric Light Chain........................................................................> pATH55 [DNA: SEQ ID NO: 46 (=nucl. 15-403 of SEQ ID NO: 21); PRT: SEQ ID NO: 25]
422 atgattgcct ctgctcagtt ccttggtctc ctgtgtctct gtttcaagg. taccagatgt gaaacaactg tgaccagtc tccagcatcc ctgtccatgg
    m   i   a   s   a   q   f   l   g   l   l   c   f   q   g   t   r   c   e   t   t   v   t   q   s   p   a   s   l   s   m
    Leader                                                                                                                FW1
    >>.........Sphingomab Chimeric Light Chain........................................................................>
522 ctataggaga aaagtcacc atcagatgca taaccaccac tgatattgat gatgatcga actgttcca gcagaagca gggaacctc ctaacctcct
    a   i   g   e   k   v   t   i   r   c   i   t   t   d   i   d   d   d   p   n   w   f   q   q   k   p   g   e   p   p   n   l
                                            CDR1                                        FW2
    >.........Sphingomab Chimeric Light Chain........................................................................>
                                            M33P >>>
622 tatttccgaa ggcaatattc ttcgtcctgg agtccatcc cgattctcca gcagtggcta tggtacagac tttctttta caattgaaaa catgctctca
    l   i   s   e   g   n   i   l   r   p   g   v   p   s   r   f   s   s   g   y   g   t   d   f   l   f   t   i   e   n   m   l   s
                CDR2                                                    FW3
    >.........Sphingomab Chimeric Light Chain........................................................................>
722 gaagatgttg cagattacta ctgtttgcag agtgataact taccattcac gttcggctcg gggacaaagt tggaaataaa acgtgagtg
    e   d   v   a   d   y   y   c   l   q   s   d   n   l   p   f   t   f   g   s   g   t   k   l   e   i   k   r   e
                                CDR3                            FW4
    >.........Sphingomab Chimeric Light Chain........................................................................>

FIG. 7E pATH10: Nucleotide Sequence: Chimeric Heavy Chain (SEQ ID NO: 26)

```
  1 atggcatgga gctgggtctt tctcttcttc ctgtcagtaa ctaccggcgt ccactcccag gctcacctgc aacagtctga cgctgaattg gtgaaacctg
                     Leader
    >>......Sphingomab Chimeric Heavy Chain..........................................................>
101 gagcttcagt gaagatatcc tgcaaggtct ctggcttcat tttcattgac catactattc actgatgaa gcagaggcct gaacaggcc tcgaatggat
                   FW1                                    CDR1                              FW2
    >......Sphingomab Chimeric Heavy Chain..........................................................>
201 cggatgtatt tctcccagac atgatattac taaatacaat gagatgttca gggcaaggc cacctgact gcagacaagt cctccactac agcctacata
                                        CDR2                                      Sphingomab Chimeric Heavy Chain..>
301 caagtcaaca gtctgacatt tgaagactct gcagtctatt tctgtgcaag aggggggttc tacgtagta ctatctggtt tgacttttgg ggccaaggca
                    FW3                                              CDR3
    >......Sphingomab Chimeric Heavy Chain..........................................................>
401 ccactctcac agtccctca gcctccacca agggcc
           FW4
    >..Sphingomab Chimeric Heavy Chain..>>
``` pATH10 protein sequence: (SEQ ID NO: 27)

```
  1 mawswvflff lsvttgvhsq ahlqqsdael vkpgasvkis ckvsgfifid htihwmkqrp eqglewigci sprhditkyn emfrgkatlt adkssttayi
101 qvnsltfeds avyfcarggf ygstiwfdfw gqgttltvss astkg
```

Nucleotide alignment of pATH10 plasmid mutations: (SEQ ID NOS 26 & 28-34 respectively in order of appearance):

```
pATH10    1 atggcatggagctgggtctttctcttcttcctgtcagtaactaccggcgtccactcccagctcacctgcaacagtctgacgctgaattggtgaaacctg
pATH11C1 415 .....................................................................................................
pATH12C2 415 .....................................................................................................
pATH13C2 271 .....................................................................................................
pATH14C1 378 .....................................................................................................
pATH15C1 414 .....................................................................................................
pATH16C1 265 .....................................................................................................
pATH17C1 282 .....................................................................................................
```

Protein alignment of pATH10 plasmid mutations to replace the cysteine residue (SEQ ID NOs 27 & 35-41 respectively in order of appearance):

```
pATH10     1 mawswvflfflsvttgvhsqahlqqsdaelvkpgasvkisckvsgfifidhtihwmkqrpeqglewigcisprhdiitkynemfrgkatltadkssttayi
pATH11C1 415 ..............................................................................a......................
pATH12C2 415 ..............................................................................s......................
pATH13C2 271 ..............................................................................w......................
pATH14C1 378 ..............................................................................y......................
pATH15C1 414 ..............................................................................r......................
pATH16

FIG. 7H

```
  815 ccactctcac agtctcctca gctccacca agggcc
           FW4
      t  t  l  t  v  s  s  a  s  t  k  g
      >..........................................> Sphingomab Chimeric Heavy Chain (path11C1)

pATH12 (DNA: SEQ ID NO: 29; PRT: SEQ ID NO: 36)

415 atggcatgga gctgggtctt tctcttcttc ctgtcagtaa ctaccggcgt ccactcccag gctcacctgc aacagtctga cgctgaattg gtgaaacctg
                   Leader
      m  a  w  s  w  v  f  l  f  f  l  s  v  t  t  g  v  h  s  q  a  h  l  q  q  s  d  a  e  l  v  k  p
      >>.........Sphingomab Chimeric Heavy Chain (path12C2).......................................>

515 gagcttcagt gaagatacc tgcaaggttt ctggcttcat tttcattgac catactgac actggatgaa gcagaggcct gaacagggcc tcgaatggat
                              FW1                      CDR1                         FW2
      g  a  s  v  k  i  s  c  k  v  s  g  f  i  f  i  d  h  t  i  h  w  m  k  q  r  p  e  q  g  l  e  w
      >..........Sphingomab Chimeric Heavy Chain (path12C2)......................................>

615 cggatctatt tctcccagac atgatattac taaatacaat gagatgttca gggcaaggc caccctgact cctccactac agcctacata
                 CDR2
      i  g  s  i  s  p  r  h  d  i  t  k  y  n  e  m  f  r  g  k  a  t  l  t  a  d  k  s  s  t  t  a  y  i
      >..........Sphingomab Chimeric Heavy Chain (path12C2)....................................>
      C51S >>>

715 caagtcaaca gtctgacatt tgaagactct gcagtctatt tctgtgcaag aggggggttc tacggtagta ctatctggtt tgacttttgg ggccaaggca
                        FW3                                                         CDR3
      q  v  n  s  l  t  f  e  d  s  a  v  y  f  c  a  r  g  g  f  y  g  s  t  i  w  f  d  f  w  g  q  g
      >..........Sphingomab Chimeric Heavy Chain (path12C2).......................................>

815 ccactctcac agtctcctca gctccacca agggcc
           FW4
      t  t  l  t  v  s  s  a  s  t  k  g
      >..........................................> Sphingomab Chimeric Heavy Chain (path12C2)

pATH13 (DNA: SEQ ID NO: 30; PRT: SEQ ID NO: 37)

271 atggcatgga gctgggtctt tctcttcttc ctgtcagtaa ctaccggcgt ccactcccag gctcacctgc aacagtctga cgctgaattg gtgaaacctg
                   Leader
      m  a  w  s  w  v  f  l  f  f  l  s  v  t  t  g  v  h  s  q  a  h  l  q  q  s  d  a  e  l  v  k  p
      >>.........Sphingomab Chimeric Heavy Chain (path13C2).......................................>

371 gagcttcagt gaagatacc tgcaaggttt ctggcttcat tttcattgac catactgac actggatgaa gcagaggcct gaacagggcc tcgaatggat
                              FW1                      CDR1                         FW2
      g  a  s  v  k  i  s  c  k  v  s  g  f  i  f  i  d  h  t  i  h  w  m  k  q  r  p  e  q  g  l  e  w
      >..........Sphingomab Chimeric Heavy Chain (path13C2)......................................>
```

FIG. 7I

```
471  cggatggatt tctcccagac atgatattac taaatacaat gagatgttca ggggcaaggc caccctgact gcagacaagt cctccactac agcctacata
                                  CDR2
     i  g  w  i  s  p  r  h  d  i  t  k  y  n  e  m  f  r  g  k  a  t  l  t  a  d  k  s  s  t  t  a  y  i
     >..................................................................Sphingomab Chimeric Heavy Chain (path13C2)
     C51W >>>

571  caagtcaaca gtctgacatt tgaagactct gcagtctatt tctgtgcaag aggggggttc tacgtagta ctatctggtt tgactttgg ggccaaggca
                              FW3                                                          CDR3
     q  v  n  s  l  t  f  e  d  s  a  v  y  f  c  a  r  g  g  f  y  g  s  t  i  w  f  d  f  w  g  q  g
     >..................................................................Sphingomab Chimeric Heavy Chain (path13C2)

671  ccactctcac agtctcctca gcctccacca agggcc
                FW4
     t  t  l  t  v  s  s  a  s  t  k  g
     >..................................................................> Sphingomab Chimeric Heavy Chain (path13C2)

pATH14 (DNA: SEQ ID NO: 31; PRT: SEQ ID NO: 38)

378  atggcatgga gctggtctt tctcttctc ctgtcagtaa ctacgggt ccactcccag gctcacctgc aacagtctga cgctgaattg gtgaaacctg
          Leader
     m  a  w  s  w  v  f  l  f  f  l  s  v  t  t  g  v  h  s  q  a  h  l  q  q  s  d  a  e  l  v  k  p
     >..................................................................Sphingomab Chimeric Heavy Chain 478  gagcttcagt gaagatatcc tgcaaggtt ctgtcacctg tttcattgac catactattc actgatgaa gcagaggcct gaacaggggcc tcgaatggat
                              FW1                      CDR1                              FW2
     g  a  s  v  k  i  s  c  k  v  s  g  f  i  f  d  h  t  i  h  w  m  k  q  r  p  e  q  g  l  e  w
     >..................................................................Sphingomab Chimeric Heavy Chain 578  cggatatatt tctcccagac atgatattac taaatacaat gagatgttca ggggcaaggc caccctgact gcagacaagt cctccactac agcctacata
                                  CDR2
     i  g  y  i  s  p  r  h  d  i  t  k  y  n  e  m  f  r  g  k  a  t  l  t  a  d  k  s  s  t  t  a  y  i
     >..................................................................Sphingomab Chimeric Heavy Chain
     C51Y >>>

678  caagtcaaca gtctgacatt tgaagactct gcagtctatt tctgtgcaag aggggggttc tacgtagta ctatctggtt tgactttgg ggccaaggca
                              FW3                                                          CDR3
     q  v  n  s  l  t  f  e  d  s  a  v  y  f  c  a  r  g  g  f  y  g  s  t  i  w  f  d  f  w  g  q  g
     >..................................................................Sphingomab Chimeric Heavy Chain 778  ccactctcac agtctcctca gcctccacca agggcc
                FW4
     t  t  l  t  v  s  s  a  s  t  k  g
     >...Sphingomab Chimeric Heavy Chain...>
```

FIG. 7J

```
pATH15 (DNA: SEQ ID NO: 32; PRT: SEQ ID NO: 39)

414 atggcatgga gctgggtctt tctcttcttc ctgtcagtaa ctacgggcgt ccactcccag aacagtctga cgctgaacctg gtgaaacctg
            m  a  w  s  w  v  f  l  f  f  l  s  v  t  t  g  v  h  s  q  a  h  l  q  q  s  d  a  e  l  v  k  p
            >>.......................Sphingomab Chimeric Heavy Chain..........................................>
                        Leader 514 gagcttcagt gaagatatcc tgcaaggttt ctggcttcat ctgtttcatt gac catactattg actggatgaa gcagaggcct gaacagggcc tcgaatggat
            g  a  s  v  k  i  s  c  k  v  s  g  f  i  f  i  d  h  t  i  h  w  m  k  q  r  p  e  q  g  l  e  w
            >.........................Sphingomab Chimeric Heavy Chain.......................................>
                        FW1                                CDR1                            FW2

614 cggagtatt tctcccagac atgatattac taaatacaat gagatgttca gggcaaggc caccctgact gcagacaagt cctccactac agcctacata
            i  g  r  i  s  p  r  h  d  i  t  k  y  n  e  m  f  r  g  k  a  t  l  t  a  d  k  s  s  t  t  a  y  i
            >........................Sphingomab Chimeric Heavy Chain..........................................>
            C51R >>>                     CDR2

714 caagtcaaca gtctgacatt tgaagactct gcagtctatt tctgtgtcaag gcagtagta ctatctgttt tgacttttgg ggccaaggca
            q  v  n  s  l  t  f  e  d  s  a  v  y  f  c  a  r  g  g  f  y  g  s  t  i  w  f  d  f  w  g  q  g
            >........................Sphingomab Chimeric Heavy Chain.........................................>
                       FW3                                     CDR3

814 ccactctcac agtctcctca gctccacca agggc
            t  t  l  t  v  s  s  a  s  t  k  g
            >...Sphingomab Chimeric Heavy Chain...>
               FW4 pATH16 (DNA: SEQ ID NO: 33; PRT: SEQ ID NO: 40)

265 atggcatgga gctgggtctt tctcttcttc ctgtcagtaa ctacgggcgt ccactcccag aacagtctga cgctgaacctg gtgaaacctg
            m  a  w  s  w  v  f  l  f  f  l  s  v  t  t  g  v  h  s  q  a  h  l  q  q  s  d  a  e  l  v  k  p
            >>......................Sphingomab Chimeric Heavy Chain..........................................>
                        Leader 365 gagcttcagt gaagatatcc tgcaaggttt ctggcttcat ctgtttcatt gac catactattg actggatgaa gcagaggcct gaacagggcc tcgaatggat
            g  a  s  v  k  i  s  c  k  v  s  g  f  i  f  i  d  h  t  i  h  w  m  k  q  r  p  e  q  g  l  e  w
            >.......................Sphingomab Chimeric Heavy Chain.........................................>
                        FW1                               CDR1                            FW2

465 cggatttatt tctcccagac atgatattac taaatacaat gagatgttca gggcaaggc caccctgact gcagacaagt cctccactac agcctacata
            i  g  f  i  s  p  r  h  d  i  t  k  y  n  e  m  f  r  g  k  a  t  l  t  a  d  k  s  s  t  t  a  y  i
            >.......................Sphingomab Chimeric Heavy Chain..........................................>
            C51F >>>                    CDR2
```

FIG. 7K

```
565  caagtcaaca gtctgacatt tgaagactct gcagtctatt tctgtgcaag aggggggttc tacggtagta ctatctggtt tgactttttgg ggccaaggca
                                        FW3                                                       CDR3
     q   v   n   s   l   t   f   e   d   s   a   v   y   f   c   a   r   g   g   f   y   s   t   i   w   f   d   f   w   g   q   g
     >..........................................................Sphingomab Chimeric Heavy Chain...>

665  ccactctcac agtctcctca gctccacca agggcc
                 FW4
     t   t   l   t   v   s   s   a   s   t   k   g
     >...Sphingomab Chimeric Heavy Chain...> pATH17 (DNA: SEQ ID NO: 34; PRT: SEQ ID NO: 41)

282  atggcatgga gctgggtctt tctcttcttc ctgtcagtaa ctaccggcgt ccactcccag gctcacctgc aacagtctga cgctgaattg gtgaaacctg
                     Leader
     m   a   w   s   w   v   f   l   f   f   l   s   v   t   t   g   v   h   s   q   a   h   l   q   q   s   d   a   e   l   v   k   p
     >>.....................................................Sphingomab Chimeric Heavy Chain..........>

382  gagcttcagt gaagatatcc tgcaaggttt ctggcttcat tttcattgac catactattg catactattg acagaggcct gaacaggggcc tcgaatggat
                                                            CDR1                                       FW2
     g   a   s   v   k   i   s   c   k   v   s   g   f   i   f   i   d   h   t   i   h   w   m   k   q   r   p   e   q   g   l   e   w
     >..........................................................Sphingomab Chimeric Heavy Chain...>

482  cggaatgatt tctccagac atgatattac taaatacaat gagatgttca gggcaaggc caccctgact gcagacaagt cctccactac agcctacata
                       CDR2
     i   g   m   i   s   p   r   h   d   i   t   k   y   n   e   m   f   r   g   k   a   t   l   t   a   d   k   s   s   t   t   a   y   i
     >...........................................................Sphingomab Chimeric Heavy Chain...>
     C51M >>>

582  caagtcaaca gtctgacatt tgaagactct gcagtctatt tctgtgcaag aggggggttc tacggtagta ctatctggtt tgactttttgg ggccaaggca
                                          FW3                                                      CDR3
     q   v   n   s   l   t   f   e   d   s   a   v   y   f   c   a   r   g   g   f   y   g   s   t   i   w   f   d   f   w   g   q   g
     >..........................................................Sphingomab Chimeric Heavy Chain...>

682  ccactctcac agtctcctca gctccacca agggcc
                 FW4
     t   t   l   t   v   s   s   a   s   t   k   g
     >...Sphingomab Chimeric Heavy Chain...>
```

# IMMUNE-DERIVED MOIETIES REACTIVE AGAINST LYSOPHOSPHATIDIC ACID

RELATED APPLICATIONS

This patent application claims priority to U.S. provisional patent application Ser. No. 60/810,185, filed 31 May 2006, U.S. provisional patent application Ser. No. 60/835,569, filed 4 Aug. 2006, and U.S. provisional patent application Ser. No. 60/923,644, filed 16 Apr. 2007. These applications are hereby incorporated by reference in their entirety for any and all purposes.

GOVERNMENT FUNDING

This invention was funded at least in part by funds supplied by the U.S. government pursuant to grant application NCI 2R44CA110298-2. As a result, the U.S. government may have certain rights in the inventions described herein.

SEQUENCE LISTING

The instant application contains a Sequence Listing that has been submitted via EFS-Web and is hereby incorporated by reference in its entirety. Said ASCII copy, created on Aug. 4, 2009, is named LPT3100UT4.txt, and is 53,940 bytes in size.

TECHNICAL FIELD

The present invention relates to monoclonal antibodies, and methods for generating antibodies against immunogens that comprise a bioactive lipid molecule that plays a role in human and/or animal disease as a signaling molecule. One particular class of signaling bioactive lipids that can be addressed in accordance with the invention is lysolipids. Particularly preferred signaling lysolipids are sphingosine-1-phosphate (S1P) and the various lysophosphatidic acids (LPAs). The antibodies of the invention can be further modified to make them suitable for use in a particular animal species, including humans, without eliciting a neutralizing immune response. Such antibodies, and derivatives and variants thereof, can be used in the treatment and/or prevention of various diseases or disorders through the delivery of pharmaceutical compositions that contain such antibodies, alone or in combination with other therapeutic agents and/or treatments. In addition, the antibodies can be also be used to detect bioactive signaling lipids in biologic samples, thereby providing useful information for many purposes including, but not limited to, the diagnosis and/or prognosis of disease and the discovery and development of new treatment modalities that modify the production and or actions of the particular targeted lipid. The diseases or conditions to be affected by the compositions of the invention include, but are not limited to, diseases that have hyperproliferation, angiogenesis, inflammation, fibrosis, and/or apoptosis as part of their underlying pathology.

BACKGROUND OF THE INVENTION

1. Introduction
The following description includes information that may be useful in understanding the present invention. It is not an admission that any such information is prior art, or relevant, to the presently claimed inventions, or that any publication specifically or implicitly referenced is prior art or even particularly relevant to the presently claimed invention.

2. Background
A. Bioactive Signaling Lipids
Lipids and their derivatives are now recognized as important targets for medical research, not as just simple structural elements in cell membranes, solubilizing agents, feedstock for vitamins or hormones or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. "Lipid signaling" refers to any of a number of cellular signal transduction pathways that use bioactive lipids as first or second messengers, including direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids derived from arachidonic acid (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG) and cardiolipins as well as lysophospholipids such as lysophosphatidyl choline (LPC) and various lysophosphatidic acids (LPA). Bioactive signaling lipid mediators also include the sphingolipids such as ceramide, ceramide-1-phosphate, sphingosine, sphinganine, sphingosylphosphorylcholine (SPC) and sphingosine-1-phosphate (S1P). Sphingolipids and their derivatives represent a group of extracellular and intracellular signaling molecules with pleiotropic effects on important cellular processes. Other examples of bioactive signaling lipids include phosphatidylinositol (PI), phosphatidylethanolamine (PEA), diacylglyceride (DG), sulfatides, gangliosides, and cerebrosides.

As expected, biological lipids (i.e., lipids that occur in nature, particularly in living organisms) are typically non-immunogenic or very weakly immunogenic. As such, lipids have traditionally been considered to be poor targets for antibody-based therapeutic and diagnostic/prognostic approaches. The literature contains a report of a monoclonal antibody that targets a derivatized form of phosphatidylserine (PS) conjugated to a carrier protein. Phosphatidylserine is a plasma membrane aminophospholipid. Loss of membrane lipid sidedness, in particular the emergence of phosphatidylserine at the cell surface, results in the expression of altered surface properties that modulates cell function and influences the cells interaction with its environment [Zwaal and Schroit, (1997) Blood, 89:1121-1132]. For example, PS redistributes from the cell membrane's inner leaflet (its normal location) to the outer leaflet during apoptosis.

Diaz, Balasubramanian and Schroit [Bioconj. Chem. (1998) 9:250-254] disclose production of lipid antigens that elicit specific immune responses against PS. The covalent coupling of PS to a protein carrier (BSA) via the lipid's fatty acyl side chain preserves the PS head group intact as an epitope. Schroit (U.S. Pat. No. 6,300,308, U.S. Pat. No. 6,806,354) discloses antibodies that specifically bind to phosphatidylserine (PS) or a phosphatidylcholine (PC)/polypeptide or a PS/polypeptide conjugate, that are made by administering a PS/polypeptide conjugate or a PC/polypeptide conjugate to an animal. Methods for detecting PS, a PC/polypeptide or a PS/polypeptide conjugate are also disclosed. Methods for making an antibody that specifically binds to PS by administering to an animal a pharmaceutical composition comprising a PS/polypeptide conjugate composition are also disclosed, as are methods for treating cancer in the animal to which the conjugate is administered, i.e., as a cancer vaccine. Also disclosed is induction of autoimmunity for the therapy of cancer by immunization of animals with β2-glycoprotein I/lipid complexes (i.e., non-covalently associated lipid and glycoprotein). The authors assert that several autoimmune responses are directed against β2-glycoprotein I/lipid complexes (citing Schousboe, (1979) Biochim. Biophys. Acta, 579:396-408), and thus the generation of an anti-complex response may represent substantial breakthroughs in the treatment of cancers.

Thorpe, Schroit et al. describe a monoclonal antibody (3G4) that binds anionic phospholipids in the presence of serum or the serum protein β 2-glycoprotein I (β2-GPI). Luster et al., J. Biol. Chem. 281: 29863-29871. Originally described as specifically targeting anionic phospholipids, this antibody localizes to vascular endothelial cells in tumors in mice. Ran et al. (2005) Clin. Cancer Res. 11:1551-1562. Subsequently, the antibody was shown to bind to complexes of anionic phospholipids and β2-GPI on tumor vessels, so that antibody binding to PS is dependent on β2-GPI. Huang et al (2005) Cancer Res. 65:4408-4416. The antibody enhances binding of β2-GPI to endothelial cells via dimerization of β2GPI. In fact, artificial β2-GPI dimers can bind to endothelial cell membranes even in the absence of antibody. Luster et al., J. Biol. Chem. 281: 29863-29871. A humanized version of 3G4 (Tarvacin, Bavituximab) is in clinical trials for treatment of cancer and viral diseases.

Thorpe et al. (WO 2004/006847) disclose antibodies, fragments or immunoconjugates thereof that bind to PS and compete with antibody 3G4 for binding to PS. Thorpe et al (U.S. Pat. No. 6,818,213, U.S. Pat. No. 6,312,294 and U.S. Pat. No. 6,783,760) disclose therapeutic conjugates that bind to aminophospholipids and have an attached therapeutic agent.

Baldo et al. (U.S. Pat. No. 5,061,626) disclose antibodies to platelet activating factor (PAF), PAF analogues used to generate antibodies and immunoassays using PAF or PAF analogues. PAF is a choline plasmalogen in which the C-2 (sn2) position of glycerol is esterified with an acetyl group instead of a long chain fatty acid.

Vielhaber et al. report characterization of two antibody reagents supposedly specific for ceramide, one an IgM-enriched polyclonal mouse serum and the other an IgM monoclonal antibody. The monoclonal was found to be specific for sphingomyelin and the antiserum was found to react with various ceramide species in the nanomolar range. Vielhaber, G. et al., (2001) Glycobiology 11:451-457. Also citing the deficiencies of commercially available antibody reagents against ceramide, Krishnamurthy et al. recently reported generation of rabbit IgG against ceramide. J. Lipid Res. (2007) 48:968-975.

B. Lysolipids

Lysolipids are low molecular weight lipids that contain a polar head group and a single hydrocarbon backbone, due to the absence of an acyl group at one or both possible positions of acylation. Relative to the polar head group at sn-3, the hydrocarbon chain can be at the sn-2 and/or sn-1 position(s) (the term "lyso," which originally related to hemolysis, has been redefined by IUPAC to refer to deacylation). See "Nomenclature of Lipids, www.chem.qmul.ac.uk/iupac/lipid/lip1n2.html. These lipids are representative of signaling, bioactive lipids, and their biologic and medical importance highlight what can be achieved by targeting lipid signaling molecules for therapeutic, diagnostic/prognostic, or research purposes (Gardell, et al. (2006), Trends in Molecular Medicine, vol 12: 65-75). Two particular examples of medically important lysolipids are LPA (glycerol backbone) and S1P (sphingoid backbone). Other lysolipids include sphingosine, lysophosphatidylcholine (LPC), sphingosylphosphorylcholine (lysosphingomyelin), ceramide, ceramide-1-phosphate, sphinganine (dihydrosphingosine), dihydrosphingosine-1-phosphate and N-acetyl-ceramide-1-phosphate. In contrast, the plasmalogens, which contain an O-alkyl (—O—CH$_2$—) or O-alkenyl ether at the C-1 (sn1) and an acyl at C-2, are excluded from the lysolipid genus.

The structures of selected LPAs, S1P, and dihydro S1P are presented below.

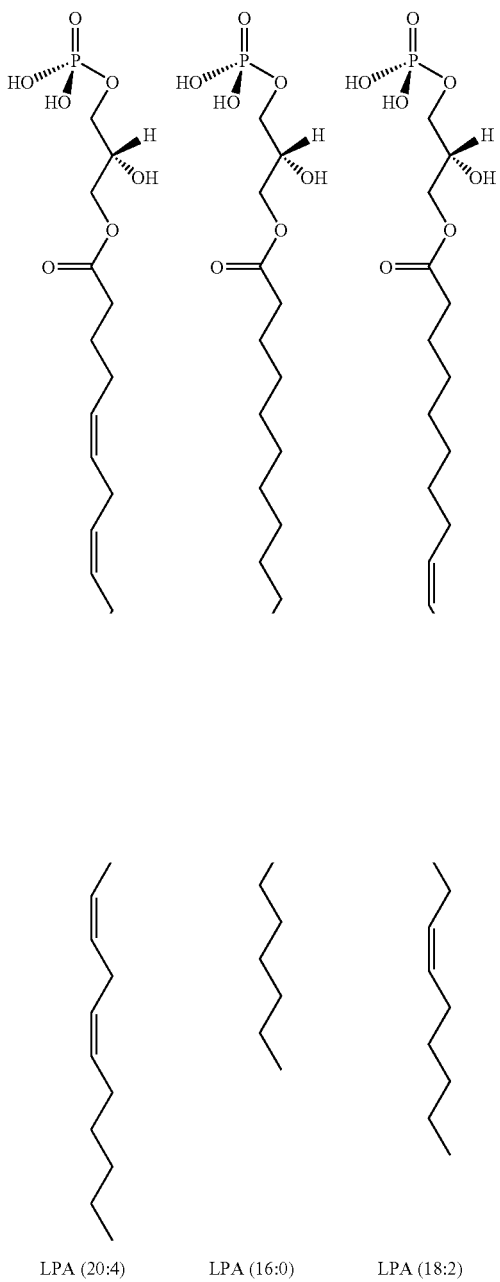

LPA (20:4)    LPA (16:0)    LPA (18:2)

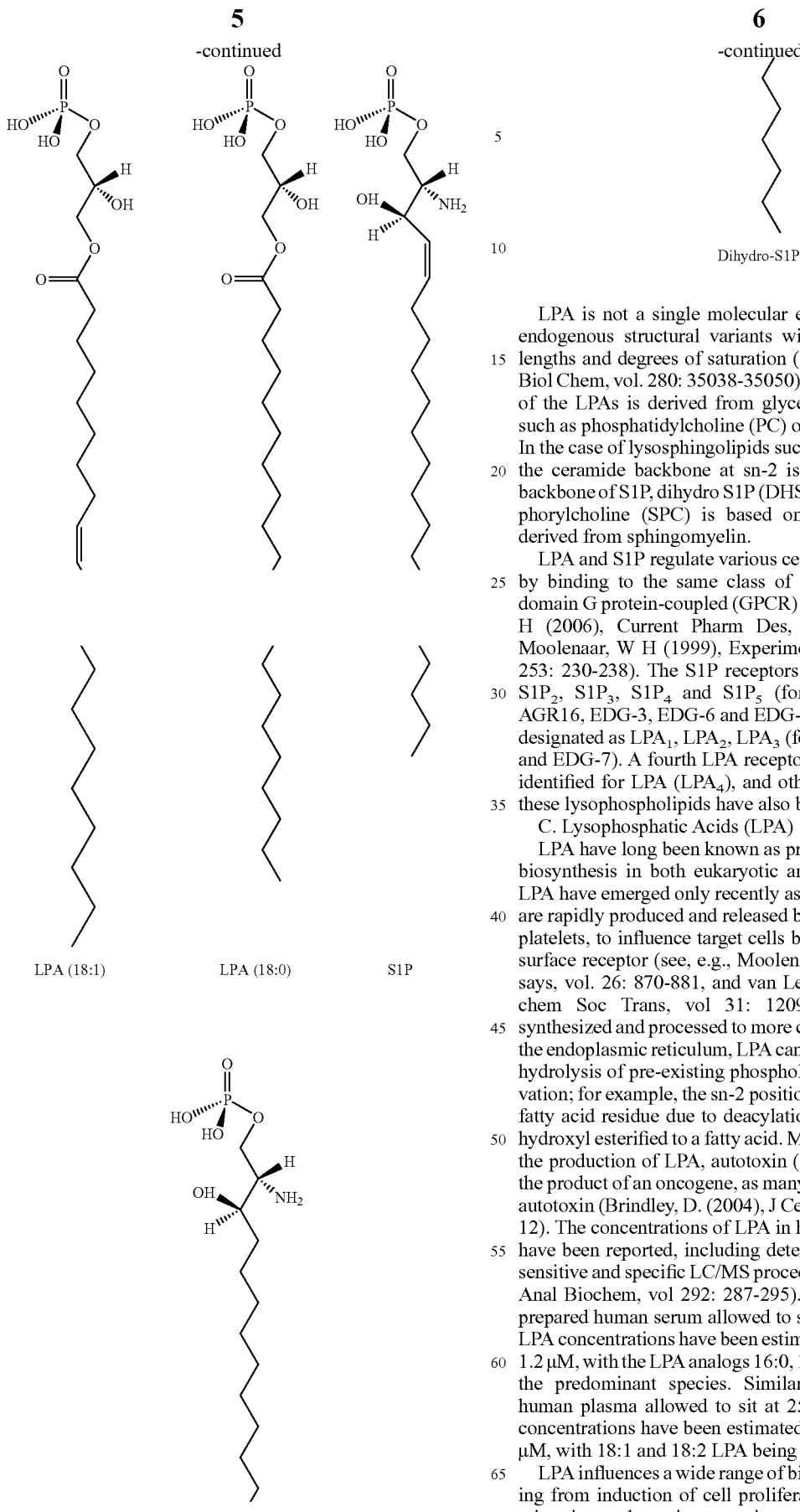

LPA is not a single molecular entity but a collection of endogenous structural variants with fatty acids of varied lengths and degrees of saturation (Fujiwara, et al. (2005), J Biol Chem, vol. 280: 35038-35050). The structural backbone of the LPAs is derived from glycerol-based phospholipids such as phosphatidylcholine (PC) or phosphatidic acid (PA). In the case of lysosphingolipids such as S1P, the fatty acid of the ceramide backbone at sn-2 is missing. The structural backbone of S1P, dihydro S1P (DHS1P) and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors (Chun J, Rosen H (2006), Current Pharm Des, vol. 12: 161-171, and Moolenaar, W H (1999), Experimental Cell Research, vol. 253: 230-238). The S1P receptors are designated as $S1P_1$, $S1P_2$, $S1P_3$, $S1P_4$ and $S1P_5$ (formerly EDG-1, EDG-5/AGR16, EDG-3, EDG-6 and EDG-8) and the LPA receptors designated as $LPA_1$, $LPA_2$, $LPA_3$ (formerly, EDG-2, EDG-4, and EDG-7). A fourth LPA receptor of this family has been identified for LPA ($LPA_4$), and other putative receptors for these lysophospholipids have also been reported.

C. Lysophosphatic Acids (LPA)

LPA have long been known as precursors of phospholipid biosynthesis in both eukaryotic and prokaryotic cells, but LPA have emerged only recently as signaling molecules that are rapidly produced and released by activated cells, notably platelets, to influence target cells by acting on specific cell-surface receptor (see, e.g., Moolenaar, et al. (2004), BioEssays, vol. 26: 870-881, and van Leewen et al. (2003), Biochem Soc Trans, vol 31: 1209-1212). Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotoxin (lysoPLD/NPP2), may be the product of an oncogene, as many tumor types up-regulate autotoxin (Brindley, D. (2004), J Cell Biochem, vol. 92: 900-12). The concentrations of LPA in human plasma and serum have been reported, including determinations made using a sensitive and specific LC/MS procedure (Baker, et al. (2001), Anal Biochem, vol 292: 287-295). For example, in freshly prepared human serum allowed to sit at 25° C. for one hour, LPA concentrations have been estimated to be approximately 1.2 µM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 µM, with 18:1 and 18:2 LPA being the predominant species.

LPA influences a wide range of biological responses, ranging from induction of cell proliferation, stimulation of cell migration and neurite retraction, gap junction closure, and even slime mold chemotaxis (Goetzl, et al (2002), Scientific World Journal, vol. 2: 324-338). The body of knowledge about the biology of LPA continues to grow as more and more cellular systems are tested for LPA responsiveness. For instance, it is now known that, in addition to stimulating cell growth and proliferation, LPA promote cellular tension and cell-surface fibronectin binding, which are important events in wound repair and regeneration (Moolenaar, et al. (2004), BioEssays, vol. 26: 870-881). Recently, anti-apoptotic activity has also been ascribed to LPA, and it has recently been reported that peroxisome proliferation receptor gamma is a receptor/target for LPA (Simon, et al. (2005), J Biol Chem, vol. 280: 14656-14662).

LPA has proven to be difficult targets for antibody production, although there has been a report in the scientific literature of the production of polyclonal murine antibodies against LPA (Chen et al. (2000) Med Chem Lett, vol 10: 1691-3).

D. Sphingosine-1-Phosphate

S1P is a mediator of cell proliferation and protects from apoptosis through the activation of survival pathways (Maceyka, et al. (2002), BBA, vol. 1585: 192-201, and Spiegel, et al. (2003), Nature Reviews Molecular Cell Biology, vol. 4: 397-407). It has been proposed that the balance between CER/SPH levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

S1P is abundantly generated and stored in platelets, which contain high levels of SPHK and lacks the enzymes for S1P degradation. When platelets are activated, S1P is secreted. In addition, other cell types, for example, mast cells, are also believed to be capable of secreting S1P. Once secreted, S1P is thought to be bound at high concentrations on carrier proteins such as serum albumin and lipoproteins. S1P is found in high concentrations in plasma, with concentrations in the range of 0.5-5 uM having been reported. Intracellular actions of S1P have also been suggested (see, e.g., Spiegel S, Kolesnick R (2002), Leukemia, vol. 16: 1596-602; Suomalainen, et al (2005), Am J Pathol, vol. 166: 773-81).

Widespread expression of the cell surface S1P receptors allows S1P to influence a diverse spectrum of cellular responses, including proliferation, adhesion, contraction, motility, morphogenesis, differentiation, and survival. This spectrum of response appears to depend upon the overlapping or distinct expression patterns of the S1P receptors within the cell and tissue systems. In addition, crosstalk between S1P and growth factor signaling pathways, including platelet-derived growth factor (PDGF), vascular endothelial growth factor (VEGF), and basic fibroblastic growth factor (bFGF), have recently been demonstrated (see, e.g., Baudhuin, et al. (2004), FASEB J, vol. 18: 341-3). The regulation of various cellular processes involving S1P has particular impact on neuronal signaling, vascular tone, wound healing, immune cell trafficking, reproduction, and cardiovascular function, among others. Alterations of endogenous levels of S1P within these systems can have detrimental effects, eliciting several pathophysiologic conditions, including cancer, heart failure, and infectious and autoimmune diseases.

A recent novel approach to treating cancer invented by Dr. Sabbadini involves reducing the biologically available extracellular levels of S1P, either alone or in combination with conventional anti-cancer treatments, including the administration of chemotherapeutic agents, such as an anthracycline. To this end, the generation of antibodies specific for S1P has been described. See, e.g., commonly owned U.S. patent application Ser. No. 10/820,582. Such antibodies, which can selectively adsorb S1P from serum, act as molecular sponges to neutralize extracellular S1P. See also commonly owned U.S. Pat. Nos. 6,881,546 and 6,858,383 and U.S. patent application Ser. Nos. 10/028,520, 10/029,372, and 11/101,976. Since S1P has also been shown to be pro-angiogenic, an added benefit to the antibody's effectiveness is its ability to starve growing tumors of nutrients and oxygen by limiting blood supply.

What is particularly unique about the anti-S1P approach is that while sphingolipid-based anti-cancer strategies that target key enzymes of the sphingolipid metabolic pathway, such as SPHK, have been proposed, the lipid mediator S1P itself was not previously emphasized, largely because of difficulties in directly mitigating this lipid target, in particular because of the difficulty first in raising antibodies against a lipid target such as S1P, and second, in detecting antibodies in fact produced against the S1P target. As already noted, similar difficulties exist with respect to treatments and diagnostic approaches directed at other lipid targets. This invention provides an effective solution to both of these dilemmas by providing patentable methods, in particular, the generation of monoclonal antibodies against bioactive lipids.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "anti-S1P antibody" refers to any antibody or antibody-derived molecule that binds S1P.

A "bioactive lipid" refers to a lipid signaling molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or GPCRs or enzymes or factors that, in turn, activate complex signaling systems that result in changes in cell function or survival. As intracellular mediators, bioactive lipids can exert their actions by directly interacting with intracellular components such as enzymes, ion channels or structural elements such as actin. Representative examples of bioactive lipids include LPA and S1P.

Examples of bioactive lipids include sphingolipids such as ceramide, ceramide-1-phosphate, sphingosine, sphinganine, sphingosylphosphorylcholine (SPC) and sphingosine-1-phosphate (S1P). Sphingolipids and their derivatives and metabolites are characterized by a sphingoid backbone (derived from sphingomyelin). Sphingolipids and their derivatives and metabolites represent a group of extracellular and intracellular signaling molecules with pleiotropic effects on important cellular processes. They include sulfatides, gangliosides and cerebrosides. Other bioactive lipids are characterized by a glycerol-based backbone; for example, lysophospholipids such as lysophosphatidyl choline (LPC) and various lysophosphatidic acids (LPA), as well as phosphatidylinositol (PI), phosphatidylethanolamine (PEA), phosphatidic acid, platelet activating factor (PAF), cardiolipin, phosphatidylglycerol (PG) and diacylglyceride (DG). Yet other bioactive lipids are derived from arachidonic acid; these include the eicosanoids (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators. Other bioactive lipids, including other phospholipids and their derivatives, may also be used according to the instant invention.

In some embodiments of the invention it may be preferable to target glycerol-based bioactive lipids (those having a glycerol-derived backbone, such as the LPAs) for antibody production, as opposed to sphingosine-based bioactive lipids (those having a sphingoid backbone, such as sphingosine and S1P). In other embodiments it may be desired to target arachidonic acid-derived bioactive lipids for antibody generation, and in other embodiments arachidonic acid-derived and glycerol-derived bioactive lipids but not sphingoid-derived bioactive lipids are preferred. Together the arachidonic acid-derived and glycerol-derived bioactive lipids may be referred to in the context of this invention as "non-sphingoid bioactive lipids."

Specifically excluded from the class of bioactive lipids according to the invention are phosphatidylcholine and phosphatidylserine, as well as their metabolites and derivatives that function primarily as structural members of the inner and/or outer leaflet of cellular membranes.

A "biomarker" is a specific biochemical in the body which has a particular molecular feature that makes it useful for measuring the progress of disease or the effects of treatment. For example, S1P is a biomarker for certain hyperproliferative and/or cardiovascular conditions.

A "carrier" refers to a moiety adapted for conjugation to a hapten, thereby rendering the hapten immunogenic. A representative, non-limiting class of carriers is proteins, examples of which include albumin, keyhole limpet hemocyanin, hemaglutanin, tetanus, and diptheria toxoid. Other classes and examples of carriers suitable for use in accordance with the invention are known in the art. These, as well as later discovered or invented naturally occurring or synthetic carriers, can be adapted for application in accordance with the invention.

The term "chemotherapeutic agent" means anti-cancer and other anti-hyperproliferative agents. Put simply, a "chemotherapeutic agent" refers to a chemical intended to destroy cells and tissues. Such agents include, but are not limited to: DNA damaging agents and agents that inhibit DNA synthesis: anthracyclines (doxorubicin, donorubicin, epirubicin), alkylating agents (bendamustine, busulfan, carboplatin, carmustine, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), and topoisomerase inhibitors (Camptosar); anti-metabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, 6-thioguanine); anti-angiogenics (bevacizumab, thalidomide, sunitinib, lenalidomide, TNP-470, 2-methoxyestradiol, ranibizumab, sorafenib, erlotinib, bortezomib, pegaptanib, endostatin); vascular disrupting agents (flavonoids/flavones, DMXAA, combretastatin derivatives such as CA4DP, ZD6126, AVE8062A, etc.); biologics such as antibodies (Herceptin, Avastin, Panorex, Rituxin, Zevalin, Mylotarg, Campath, Bexxar, Erbitux); endocrine therapy: aromatase inhibitors (4-hydroandrostendione, exemestane, aminoglutehimide, anastrazole, letozole), anti-estrogens (Tamoxifen, Toremifine, Raoxifene, Faslodex), steroids such as dexamethasone; immuno-modulators: cytokines such as IFN-beta and IL2), inhibitors to integrins, other adhesion proteins and matrix metalloproteinases); histone deacetylase inhibitors like suberoylanilide hydroxamic acid; inhibitors of signal transduction such as inhibitors of tyrosine kinases like imatinib (Gleevec); inhibitors of heat shock proteins like 17-N-allylamino-17-demethoxygeldanamycin; retinoids such as all trans retinoic acid; inhibitors of growth factor receptors or the growth factors themselves; anti-mitotic compounds and/or tubulin-depolymerizing agents such as the taxoids (paclitaxel, docetaxel, taxotere, BAY 59-8862), navelbine, vinblastine, vincristine, vindesine and vinorelbine; anti-inflammatories such as COX inhibitors and cell cycle regulators, e.g., check point regulators and telomerase inhibitors.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody. Alternatively, a combination therapy may involve the administration of an anti-lipid antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

A "derivatized bioactive lipid conjugate" refers to a derivatized bioactive lipid covalently conjugated to a carrier. The carrier may be a protein molecule or may be a moiety such as polyethylene glycol, colloidal gold, adjuvants or silicone beads. A derivatized bioactive lipid conjugate may be used as an immunogen for generating an antibody response according to the instant invention, and the same or a different bioactive lipid conjugate may be used as a detection reagent for detecting the antibody thus produced. In some embodiments the derivatized bioactive lipid conjugate is attached to a solid support when used for detection.

An "epitope" or "antigenic determinant" refers to that portion of an antigen that reacts with an antibody antigen-binding portion derived from an antibody.

A "hapten" is a substance that is non-immunogenic but can react with an antibody or antigen-binding portion derived from an antibody. In other words, haptens have the property of antigenicity but not immunogenicity.

The term "hyperproliferative disorder" refers to diseases and disorders associated with, the uncontrolled proliferation cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (i.e., fibrogenesis) include but are not limited to disorders of excessive scarring (i.e., fibrosis) such as age-related macular degeneration, cardiac remodeling and failure associated with myocardial infarction, excessive wound healing such as commonly occurs as a consequence of surgery or injury, keloids, and fibroid tumors and stenting.

An "immunogen" is a molecule capable of inducing a specific immune response, particularly an antibody response in an animal to whom the immunogen has been administered. In the instant invention, the immunogen is a derivatized bioactive lipid conjugated to a carrier, i.e., a "derivatized bioactive lipid conjugate". The derivatized bioactive lipid conjugate used as the immunogen may be used as capture material for detection of the antibody generated in response to the immunogen. Thus the immunogen may also be used as a detection reagent. Alternatively, the derivatized bioactive lipid conjugate used as capture material may have a different linker and/or carrier moiety from that in the immunogen.

To "inhibit," particularly in the context of a biological phenomenon, means to decrease, suppress or delay. For example, a treatment yielding "inhibition of tumorigenesis" may mean that tumors do not form at all, or that they form more slowly, or are fewer in number than in the untreated control.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

"Monotherapy" refers to a treatment regimen based on the delivery of one therapeutically effective compound, whether administered as a single dose or several doses over time.

"Neoplasia" refers to abnormal and uncontrolled cell growth. A "neoplasm", or tumor, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatic or blood circulating systems. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the non-patentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, non-reacted chemicals, proteins, carbohydrates, lipids, and unbound molecules.

The term "species" is used herein in various contexts, e.g., a particular species of chemotherapeutic agent. In each context, the term refers to a population of chemically indistinct molecules of the sort referred in the particular context.

"Specifically associate," "specifically bind" and the like refer to a specific, non-random interaction between two molecules, which interaction depends on the presence of structural, hydrophobic/hydrophilic, and/or electrostatic features that allow appropriate chemical or molecular interactions between the molecules. An antibody may be said to "bind" or be "reactive with" (or, equivalently, "reactive against") the epitope of its target antigen. Antibodies are commonly described in the art as being "against" or "to" their antigens as shorthand for antibody binding to the antigen.

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-humans primates) animals being particularly preferred examples.

A "surrogate marker" refers to laboratory measurement of biological activity within the body that indirectly indicates the effect of treatment on disease state. Examples of surrogate markers for hyperproliferative and/or cardiovascular conditions include SPHK and/or S1PRs.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The term "treatment" or "treating" means any treatment of a disease or disorder, including preventing or protecting against the disease or disorder (that is, causing the clinical symptoms not to develop); inhibiting the disease or disorder (i.e., arresting, delaying or suppressing the development of clinical symptoms; and/or relieving the disease or disorder (i.e., causing the regression of clinical symptoms). As will be appreciated, it is not always possible to distinguish between "preventing" and "suppressing" a disease or disorder because the ultimate inductive event or events may be unknown or latent. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, aptamers and other biologics such as antibodies and antibody variants, receptor decoys and other protein-based therapeutics.

SUMMARY OF THE INVENTION

The object of this invention is to provide patentable compositions and methods for generating antibodies, particularly monoclonal antibodies and derivatives thereof, reactive with bioactive lipids correlated, involved, or otherwise implicated in disease processes in animals, particularly in mammals, especially humans.

Thus, one aspect of the invention concerns patentable intermediates used to produce patentable immunogens that can be used to raise patentable bioactive lipid-reactive antibodies. This patentable class of compounds comprises derivatized bioactive lipids, each of which comprises a bioactive lipid having a polar head group and at least one hydrocarbon chain, wherein a carbon atom within the hydrocarbon chain is derivatized with a pendant reactive group [e.g., a sulfhydryl (thiol) group, a carboxylic acid group, a cyano group, an ester, a hydroxy group, an alkene, an alkyne, an acid chloride group or a halogen atom] that may or may not be protected. Representative bioactive lipids include lysolipids, for example, sphingolipids and sphingolipid metabolites such as ceramide, ceramide-1-phosphate, N-acetyl-ceramide-1-phosphate, sphingosine-1-phosphate (S1P), sphingosine, sphingosylphosphorylcholine (SPC), dihydrosphingosine and dihydrosphingosine-1-phosphate. Other bioactive lipids include lysolipids such as lysophosphatidic acids (LPAs), as well as lysophosphatidic acid metabolites or precursors such as lysophosphatidylinositol (LPI) or lysophosphatidylcholine (LPC). In the context of an LPA, exemplary reactive group positioning includes appending the reactive group to a carbon atom within the hydrocarbon chain or at the sn-1 position of the glycerol backbone of the lysophosphatidic acid moiety. Particularly preferred derivatized bioactive lipids include sulfhydryl derivatives of LPA and S1P.

A related aspect of the invention relates to immunogens produced from a derivatized bioactive lipid according to the invention. In general, such immunogens comprise a derivatized bioactive lipid covalently linked to a carrier. Examples of suitable carrier moieties include carrier proteins such as keyhole limpet hemocyanin (KLH) and albumin, polyethylene glycol, colloidal gold, adjuvants or silicone beads. Preferred embodiments of an immunogen according to the invention include a sulfhydryl derivative of LPA covalently linked to KLH or albumin. In the context of sphingolipid-based immunogen, preferred immunogen embodiments include sulfhydryl derivatives of S1P covalently linked to KLH or albumin.

Immunogens of the invention are prepared by reaction of a derivatized bioactive bioactive lipid with a carrier moiety under conditions that allow covalent linkage between the carrier and the bioactive lipid to occur through the pendant reactive group to yield the particular species of bioactive lipid-carrier immunogen. Such immunogens are then preferably isolated or purified prior to administration to a host animal as part of an immunization procedure, which may involve one or several administrations (typically by injection) of the desired immunogen. In preferred embodiments of this aspect, the pendant reactive group of the derivatized bioactive lipid is protected with a suitable protecting group, which is removed and the derivatized bioactive lipid is "deprotected" prior to or as part of the chemistry employed to covalently link the carrier and the bioactive lipid.

As discussed above, another aspect of the invention concerns methods of making monoclonal antibody reactive against a bioactive lipid. In such methods, an immune competent host animal (e.g., a rodent such as a mouse, a rat, a guinea pig, or rabbit) is immunized with a bioactive lipid immunogen as described herein. Following immunization, the host mounts an antibody response against the bioactive lipid, resulting in the production of antibodies reactive to the particular bioactive lipid species present in the immunogen. The resultant antibodies may be polyclonal or, preferably, monoclonal. With regard to monoclonal antibodies, cell lines that produce a desired antibody are preferably cloned and immortalized to facilitate production of the desired lipid-specific antibody in desired quantities. In preferred embodiments, a desired monoclonal antibody, e.g., a monoclonal antibody reactive against LPA is used to produce antibody derivatives, such as chimeric or humanized antibodies or antibody fragments. In some embodiments, fully humanized antibodies may be produced by immunizing an animal, e.g., a mouse or rat, engineered to contain some or all of a competent human system.

It is known that lipids are in general a particularly intractable class of molecules for antibody production. One facet of the invention rests on the appreciation that this problem, at least in part, resides in the difficulty in detecting antibodies reactive against a particular target lipid species. However, this problem can be elegantly overcome through the use of the derivatized form of the particular target bioactive lipid, such as a lysolipid or a sphingolipid or sphingolipid metabolite).

In certain preferred embodiments, such a derivatized bioactive lipid may be used to identify an antibody reactive against an epitope of the particular bioactive lipid present in the immunogen used to generate the antibodies being detected. To perform this role a particular derivatized bioactive lipid or derivatized bioactive lipid conjugate may be attached to a solid support, preferably the solid phase of an assay device, such as an ELISA plate, a Biacore chip, etc. Attachment to a solid support minimizes the likelihood that the bioactive lipid will be washed away during antibody binding and detection.

Another aspect of the invention concerns pharmaceutical or veterinary compositions that comprise a carrier and an isolated immune-derived moiety according to the invention, for example, a monoclonal antibody or antibody fragment, variant, or derivative. Preferred carriers include those that are pharmaceutically acceptable, particularly when the composition is intended for therapeutic use in humans. For non-human therapeutic applications (e.g., in the treatment of companion animals, livestock, fish, or poultry), acceptable carriers for veterinary use may be employed.

Related aspects of the invention relate to methods of use or treatment, including preventative or prophylactic treatment, and administration. Such methods typically involve administering to a subject (for example, mammal, particularly a human patient) in need of therapeutic or prophylactic treatment an amount of an immune-derived moiety reactive against a bioactive lipid target, effective to accomplish the desired treatment. In some embodiments the bioactive lipid target is a non-sphingoid bioactive lipid. One preferred example of a therapeutically useful immune-derived moiety is a humanized monoclonal antibody reactive against a lysolipid such as LPA. Routes of administration of an immune-derived moiety according to the invention, preferably as part of a therapeutic composition, may vary depending upon whether local or systemic treatment is desired and upon the area to be treated. Administration may be topical (including transdermal, ophthalmic and to mucous membranes including vaginal, intrauterine and rectal delivery, pulmonary delivery, intratracheal, intranasal, and epidermal delivery), oral or parenteral. Parenteral administration includes intravenous, intraarterial, subcutaneous, intraperitoneal or intramuscular injection or infusion; or intracranial, e.g., intrathecal or intraventricular, administration.

Other aspects of the invention concern various diagnostic, prognostic, and/or research-enabling methods. One such aspect involves use of the derivatized lipid analog to detect the presence of autoantibodies against the natural bioactive lipid in a sample of fluid or tissue from an animal or from an antibody library. Another such aspect concerns methods of detecting target bioactive lipids, other than sphingolipids or metabolites thereof. In general, such methods involve binding of an immune-derived moiety with the target bioactive lipid against which it is reactive. Detection of binding may result, for example, by exposing a sample (e.g., a biopsy or fluid or liquid sample, for instance, blood, serum, plasma, urine, saliva, tears, cerebrospinal fluid, cell culture, etc.) known or suspected to contain the target bioactive lipid with an immune-derived moiety under conditions that allow the immune-derived moiety to bind to the target bioactive lipid, if present in the sample.

To perform such diagnostic methods, reagents are required, and diagnostic reagents that employ a derivatized lipid according to the invention represent another aspect of the invention. With such reagents in hand, diagnostic assays that utilize such reagents may be prepared.

These and other aspects and embodiments of the invention are discussed in greater detail in the sections that follow.

BRIEF DESCRIPTION OF THE DRAWINGS

FIG. 1. Organic synthesis scheme for making of a typical thiolated-S1P analog that was used as a key component of an immunogen according to the invention, as well as a key component of the laydown material for the ELISA and BiaCore assays.

FIG. 2. Organic synthesis scheme for making the thiolated-related fatty acid used in the synthesis of the thiolated-LPA analog of FIG. 3.

FIG. 3. Organic synthesis scheme for making the thiolated-LPA analog that is a key component of an immunogen according to the invention, as well as a key component of the laydown material for the ELISA and other assays.

FIG. 6. Amino acid sequences of the mouse $V_H$ (SEQ ID NO: 6) and $V_L$ (SEQ ID NO: 9) domains of murine Sphingomab™. CDR residues are boxed.

FIG. 7. Nucleotide and amino acid sequences of the $V_H$ and $V_L$ domains of murine Sphingomab™ (SEQ ID NOs: 16-46 as indicated).

Figure 1A:
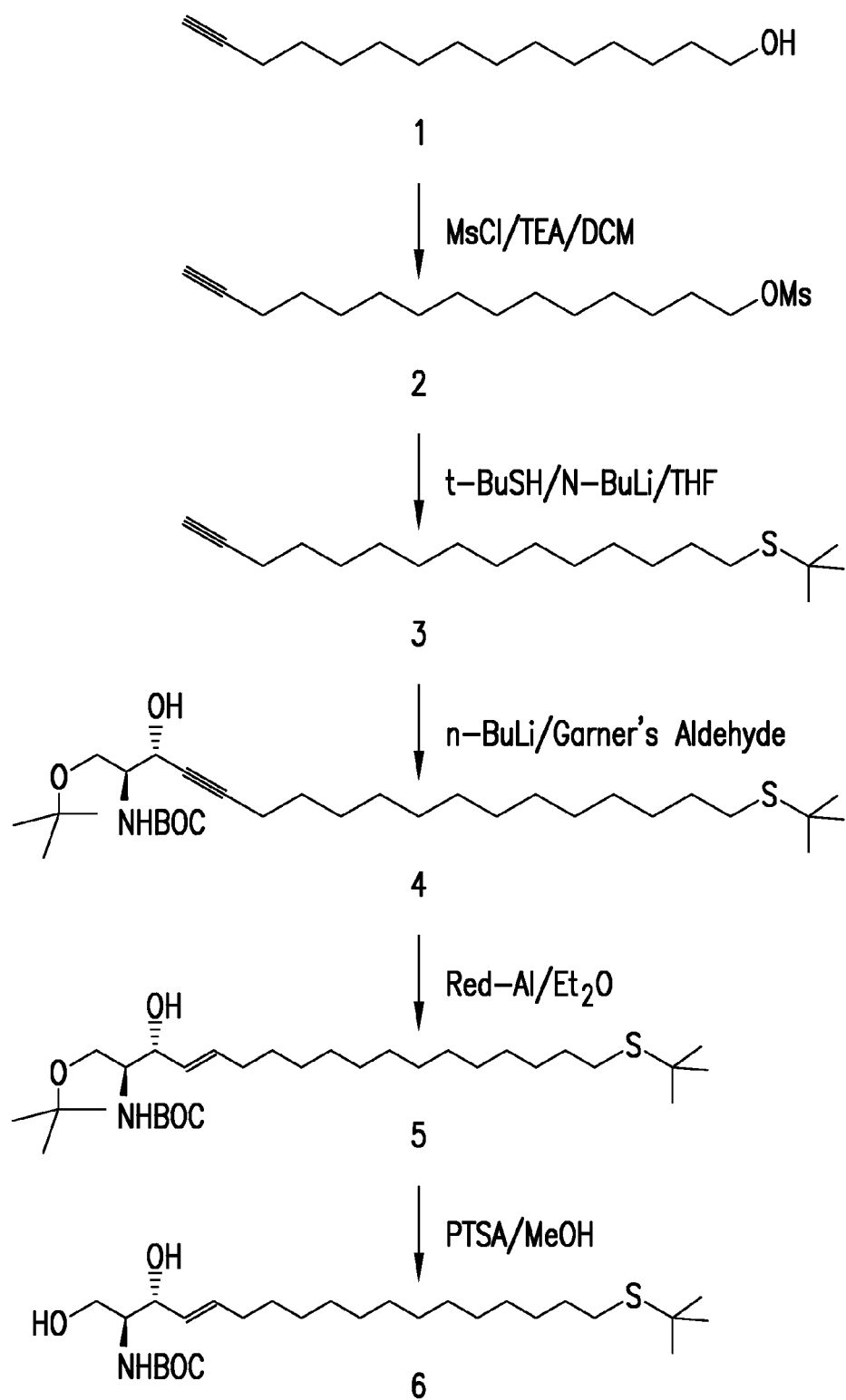
FIG. 1a shows the initial portion of a synthesis scheme for a typical thiolated S1P-related antigen.

As those in the art will appreciate, the following description describes certain preferred embodiments of the invention in detail, and is thus only representative and does not depict the actual scope of the invention. Before describing the present invention in detail, it is understood that the invention is not limited to the particular molecules, systems, and methodologies described, as these may vary. It is also to be understood that the terminology used herein is for the purpose of describing particular embodiments only, and is not intended to limit the scope of the invention defined by the appended claims.

DETAILED DESCRIPTION OF THE INVENTION

The present invention relates to compositions and methods for generating and identifying antibodies against bioactive lipid molecules that play a role in human and/or animal disease as a signaling molecule. The invention also relates to these antibodies themselves, and methods of using them therapeutically, diagnostically and as research reagents.

1. Methods for Antibody Production and Identification

It is known that lipids are in general a particularly intractable class of molecules for antibody production. Antibody production can typically be described as a two-part process: a suitable immunogen must be provided which will generate the desired antibody response in an animal, and the resulting antibody, if present, must be detectable.

As discussed above, effective antibody production requires both antibody generation and antibody detection. As disclosed in the Examples hereinbelow, generation of antibodies targeted to certain bioactive lipids has been achieved using derivatized bioactive lipid as immunogen. In the examples, the thiolated bioactive lipid (e.g., S1P) analog was conjugated to Keyhole Limpet Hemocyanin (KLH) or to fatty-acid free Bovine Serum Albumin (BSA) via SMCC (Pierce, Rockford Ill.) using protocols recommended by the manufacturer. SMCC is a heterobifunctional crosslinker that reacts with primary amines and sulfhydryl groups, and represents a preferred crosslinker. Iodoacetamide (IOA) can also be used for maleimide-activated proteins.

However, other immunogens and methods of generating antibodies known in the art may also be used. For example, antibodies against phospholipid species have been generated by immunization with liposomes (Maneta-Peyret et al., 1988, 1989; Benerji and Alving, 1990) or by adsorption of monomeric phospholipids to proteins (Tamamura et al., 1971; Maneta-Peyret et al., 1989), to bacteria (Umeda et al., 1989), to acrylamide (Maneta-Peyret et al., 1988, 1989) and to gold [Tomii et al., (1991) Jpn J. Med. Sci. Biol. 44:75-80]. In many cases, presentation of the bioactive lipid as emulsions or liposomal complexes has resulted in IgMs with limited specificity, sensitivity and/or biological activity in comparison to IgG. For example, two commercially available reagents supposedly specific for ceramide, one an IgM-enriched polyclonal mouse serum and the other an IgM monoclonal antibody, were characterized. The monoclonal was found to be specific for sphingomyelin and the antiserum was found to react with various ceramide species in the nanomolar range. Vielhaber, G. et al., (2001) Glycobiology 11:451-457. In a different approach, Ran et al. [(2005) Clin. Cancer Res. 11: 1551-1562] used b.End3 endothelial cells that had been treated with peroxide (intended to cause translocation of anionic phospholipids to the external surface of the cells) as an immunogen to elicit generation of antibodies specific for anionic phospholipids. Thus numerous methods are known by which an antibody response to a desired antigenic target may be elicited; any of these may be used in the instant invention as long as the resulting antibodies can be detected and shown to be reactive with the desired bioactive lipid.

Antibody generation, while of course necessary, is not sufficient if the antibody cannot be detected. Thus one facet of the invention rests on the appreciation that previous failures of others to produce antibodies to bioactive lipids may be attributable at least to shortcomings in the detection step. This problem of detection has been elegantly overcome in the following examples through the use of a derivatized bioactive lipid. The derivatized bioactive lipid is used to detect and identify an antibody reactive against an epitope of the particular bioactive lipid present in the immunogen used to generate the antibodies being detected; the bioactive lipid used for detection in derivatized form contains the same epitope to which antibodies were generated. To perform this role the derivatized lipid may be associated with the solid phase of an assay device, such as an ELISA plate, a BiaCore sensor chip, etc. In some embodiments the derivatized bioactive lipid is covalently conjugated directly to the solid support. By way of example, the derivatized lipid may be covalently conjugated to an activated BiaCore chip as described in Examples hereinbelow. In other embodiments, the derivatized bioactive lipid is covalently conjugated to a carrier moiety, yielding a "derivatized bioactive lipid conjugate" which is then bound to a solid support. As an example, derivatized lipid covalently conjugated to BSA is used as the laydown material (capture material) for ELISA as described in Examples hereinbelow. In either embodiment, attachment of the derivatized bioactive lipid to the solid support provides a stable detection means which is unlikely to be washed away, as is a risk of some detection methods. Detection of the antibody may be accomplished in a variety of ways. In a preferred embodiment of the invention, the detection is via ELISA, Biacore™ label-free interaction analysis systems, or other solid-support-based routine detection means in which the derivatized bioactive lipid is attached to said solid support. Examples of other solid supports include but are not limited to affinity columns, glass or synthetic beads, multiwell plates and the like.

The derivatized bioactive lipid conjugate used in the detection step may be the same derivatized bioactive lipid conjugate used as the immunogen, or the derivatized bioactive lipid may be conjugated to a different carrier than in the conjugate used as the immunogen. In some embodiments, e.g. as the laydown for ELISA, it is preferred to use a different derivatized bioactive lipid conjugate in the detection step, than was used as the immunogen, to minimize crossreactivity. By way of examples, the carrier may be BSA (preferably fatty-acid free, particularly in the detection step), KLH or other carriers known in the art. The crosslinker used to conjugate the derivatized bioactive lipid to the protein carrier may be, for example, SMCC or IOA. In one preferred embodiment the immunogen is S1P-IOA-KLH and S1P-SMCC-BSA (fatty acid free BSA) is the capture laydown material in the ELISA, wherein S1P refers to the derivatized S1P that reacts with the crosslinker (IOA or SMCC in this instance) to form a covalent bond with the protein carrier (KLH or BSA in this instance).

2. Compounds

The term "antibody" ("Ab") or "immunoglobulin" (Ig) refers to any form of a peptide, polypeptide derived from, modeled after or encoded by, an immunoglobulin gene, or fragment thereof, capable of binding an antigen or epitope. See, e.g., IMMUNOBIOLOGY, Fifth Edition, C. A. Janeway, P. Travers, M., Walport, M. J. Shlomchiked., ed. Garland Publishing (2001). Antibody molecules or immunoglobulins are large glycoprotein molecules with a molecular weight of approximately 150 kDa, usually composed of two different kinds of polypeptide chain. One polypeptide chain, termed the "heavy" chain (H) is approximately 50 kDa. The other polypeptide, termed the "light" chain (L), is approximately 25 kDa. Each immunoglobulin molecule usually consists of two heavy chains and two light chains. The two heavy chains are linked to each other by disulfide bonds, the number of which varies between the heavy chains of different immunoglobulin isotypes. Each light chain is linked to a heavy chain by one covalent disulfide bond. In any given naturally occurring antibody molecule, the two heavy chains and the two light chains are identical, harboring two identical antigen-binding sites, and are thus said to be divalent, i.e., having the capacity to bind simultaneously to two identical molecules.

The "light" chains of antibody molecules from any vertebrate species can be assigned to one of two clearly distinct types, kappa (k) and lambda (λ), based on the amino acid sequences of their constant domains. The ratio of the two types of light chain varies from species to species. As a way of example, the average k to λ ratio is 20:1 in mice, whereas in humans it is 2:1 and in cattle it is 1:20.

The "heavy" chains of antibody molecules from any vertebrate species can be assigned to one of five clearly distinct types, called isotypes, based on the amino acid sequences of their constant domains. Some isotypes have several subtypes. The five major classes of immunoglobulin are immunoglobulin M (IgM), immunoglobulin D (IgD), immunoglobulin G (IgG), immunoglobulin A (IgA), and immunoglobulin E (IgE). IgG is the most abundant isotype and has several subclasses (IgG1, 2, 3, and 4 in humans). The Fc fragment and hinge regions differ in antibodies of different isotypes, thus determining their functional properties. However, the overall organization of the domains is similar in all isotypes.

As used herein, "antibody fragment" and grammatical variants thereof refer to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Examples of antibody fragments are those that retain antigen-binding and include Fab, Fab', F(ab')$_2$, Fd, and Fv fragments; diabodies; triabodies; single-chain antibody molecules (sc-Fv); minibodies, nanobodies, and multispecific antibodies formed from antibody fragments. By way of example, a Fab fragment also contains the constant domain of a light chain and the first constant domain (CH1) of a heavy chain.

The term "variable region" refers to N-terminal sequence of the antibody molecule or a fragment thereof. In general, each of the four chains has a variable (V) region in its amino terminal portion, which contributes to the antigen-binding site, and a constant (C) region, which determines the isotype. The light chains are bound to the heavy chains by many noncovalent interactions and by disulfide bonds, and the V regions of the heavy and light chains pair in each arm of antibody molecule to generate two identical antigen-binding sites. Some amino acid residues are believed to form an interface between the light- and heavy-chain variable domains (see Kabat et al., Sequences of Proteins of Immunological Interest, Fifth Edition, National Institute of Health, Bethesda, Md. (1991); Clothia et al., J. Mol. Biol., vol. 186: 651 (1985)).

Of note, variability is not uniformly distributed throughout the variable domains of antibodies, but is concentrated in three segments called "complementarity-determining regions" (CDRs) or "hypervariable regions" both in the light-chain and the heavy-chain variable domains. The more highly conserved portions of variable domains are called the "framework region" (FR). The variable domains of native heavy and light chains each comprise four FR regions connected by three CDRs. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). Collectively, the 6 CDRs contribute to the binding properties of the antibody molecule. However, even a single variable domain (or half of an Fv comprising only three CDRs specific for an antigen) has the ability to recognize and bind antigen (see Pluckthun, in The Pharmacology of Monoclonal Antibodies, vol. 113, Rosenburg and Moore eds., Springer-Verlag, New York, pp. 269-315 (1994)).

The terms "constant domain" refers to the C-terminal region of an antibody heavy or light chain. Generally, the constant domains are not directly involved in the binding properties of an antibody molecule to an antigen, but exhibit various effector functions, such as participation of the antibody in antibody-dependent cellular toxicity. Here, "effector functions" refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

The term "variant" refers to an amino acid sequence which differs from the native amino acid sequence of an antibody by at least one amino acid residue modification. A native or parent or wild-type amino acid sequence refers to the amino acid sequence of an antibody found in nature. "Variant" of the antibody molecule includes, but is not limited to, changes within a variable region or a constant region of a light chain and/or a heavy chain, including in the Fc region, the Fab region, the $CH_1$ domain, the $CH_2$ domain, the $CH_3$ domain, and the hinge region.

The term "specific" refers to the selective binding of an antibody to its target epitope. Antibody molecules can be tested for specificity of binding by comparing binding to the desired antigen to binding to unrelated antigen or analogue antigen or antigen mixture under a given set of conditions. Preferably, an antibody according to the invention will lack significant binding to unrelated antigens, or even analogs of the target antigen. Here, the term "antigen" refers to a molecule that is recognized and bound by an antibody molecule or immune-derived moiety that binds to the antigen. The specific portion of an antigen that is bound by an antibody is termed the "epitope". A "hapten" refers to a small molecule that can, under most circumstances, elicit an immune response (i.e., act as an antigen) only when attached to a carrier, for example, a protein, polyethylene glycol (PEG), colloidal gold, silicone beads, and the like. The carrier may be one that also does not elicit an immune response by itself.

The term "antibody" is used in the broadest sense, and encompasses monoclonal, polyclonal, multispecific (e.g., bispecific, wherein each arm of the antibody is reactive with a different epitope of the same or different antigen), minibody, heteroconjugate, diabody, triabody, chimeric, and synthetic antibodies, as well as antibody fragments that specifically bind an antigen with a desired binding property and/or biological activity.

The term "monoclonal antibody" (mAb) refers to an antibody, or population of like antibodies, obtained from a population of substantially homogeneous antibodies, and is not to be construed as requiring production of the antibody by any particular method. For example, monoclonal antibodies can be made by the hybridoma method first described by Kohler G. and Milstein C. (1975), Nature, vol. 256:495-497, or by recombinant DNA methods.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., infra; Morrison et al., Proc. Natl. Acad. Sci. U.S.A., vol. 81:6851 (1984)).

The term "humanized antibody" means human antibodies that also contain selected sequences from non-human (e.g., murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly, et al, U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, et al., WO 86/01533; Neuberger, et al., European Patent No. 0,194,276 B1; Winter, U.S. Pat. No. 5,225,539; Winter, European Patent No. 0,239,400 B1; Padlan, et al., European Patent Application No. 0,519,596 A1; Queen, et al. (1989), Proc. Nat'l Acad. Sci. USA, vol. 86:10029-10033).

The term 'fully human' antibody can refer to an antibody produced in a genetically engineered (ie. Transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. The applicants believe that antibodies could be generated against bioactive lipids when presented to these genetically engineered mice or other animals who might be able to produce human frameworks for the relevant CDRs.

The term "bispecific antibody" can refer to an antibody, or a monoclonal antibody, having binding properties for at least two different epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. Alternatively, bispecific antibodies can be prepared using chemical linkage. One of skill can produce bispecific antibodies using these or other methods as may be known in the art. Bispecific antibodies include bispecific antibody fragments. One example of a bispecific antibody comprehended by this invention is an antibody having binding properties for an S1P epitope and an LPA epitope, which thus is able to recognize and bind to both S1P and LP1. Another example of a bispecific antibody comprehended by this invention is an antibody having binding properties for an epitope from a bioactive lipid and an epitope from a cell surface antigen. Thus the antibody is able to recognize and bind the bioactive lipid and is able to recognize and bind to cells, e.g., for targeting purposes.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

The term "biologically active" refers to an antibody or antibody fragment that is capable of binding the desired epitope and in some ways exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

A "vector" or "plasmid" or "expression vector" refers to a nucleic acid that can be maintained transiently or stably in a cell to effect expression of one or more recombinant genes. A vector can comprise nucleic acid, alone or complexed with other compounds. A vector optionally comprises viral or bacterial nucleic acids and/or proteins, and/or membranes. Vectors include, but are not limited to, replicons (e.g., RNA replicons, bacteriophages) to which fragments of DNA may be attached and become replicated. Thus, vectors include, but are not limited to, RNA, autonomous self-replicating circular or linear DNA or RNA and include both the expression and non-expression plasmids. "Plasmids" can be commercially available, publicly available on an unrestricted basis, or can be constructed from available plasmids as reported with published protocols. In addition, the expression vectors may also contain a gene to provide a phenotypic trait for selection of transformed host cells such as dihydrofolate reductase or neomycin resistance for eukaryotic cell culture, or such as tetracycline or ampicillin resistance in E. coli.

The term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Transcriptional regulatory regions suitable for use in the present invention include but are not limited to the human cytomegalovirus (CMV) immediate-early enhancer/promoter, the SV40 early enhancer/promoter, the E. coli lac or trp promoters, and other promoters known to control expression of genes in prokaryotic or eukaryotic cells or their viruses.

A. Antibodies to Sphingolipids

The present invention provides methods for preparing antibodies directed against certain bioactive lipids, including sphingolipids. The term "sphingolipid" refers to the sphingolipids as defined by http//www.lipidmaps.org, including the following: Sphingoid bases [including sphing-4-enines (sphingosines), sphinganines, 4-hydroxysphinganines (phytosphingosines), sphingoid base homologs and variants, sphingoid base 1-phosphates, lysosphingomyelins and lysoglycosphingolipids; N-methylated sphingoid bases, and sphingoid base analogs]; ceramides [including N-acylsphingosines (ceramides), N-acylsphinganines (dihydroceramides), N-acyl-4-hydroxysphinganines (phytoceramides), acylceramides and ceramide 1-phosphates]; phosphosphingolipids [including ceramide phosphocholines (sphingomyelins), ceramide phosphoethanolamines and ceramide phosphoinositols; phosphonosphingolipids; neutral glycosphingolipids [including the simple Glc series (GlcCer, LacCer, etc., GalNAcb1-3Gala1-4Galb1-4Glc- (Globo series), GalNAcb1-4Galb1-4Glc- (Ganglio series), Galb1-3GlcNAcb1-3Galb1-4Glc- (Lacto series), Galb1-4GlcNAcb1-3Galb1-4Glc- (Neolacto series), GalNAcb1-3Gala1-3Galb1-4Glc- (Isoglobo series), GlcNAcb1-2Mana1-3Manb1-4Glc- (Mollu series), GalNAcb1-4GlcNAcb1-3Manb1-4Glc- (Arthro series), Gal- (Gala series) or other neutral glycosphingolipids]; acidic glycosphingolipids [including gangliosides, sulfoglycosphingolipids (sulfatides), glucuronosphingolipids, phosphoglycosphingolipids and other acidic glycosphingolipids; basic glycosphingolipids; amphoteric glycosphingolipids; arsenosphingolipids and other sphingolipids.

Anti-sphingolipid antibodies are useful for treating or preventing disorders such as hyperproliferative disorders and cardiovascular or cerebrovascular diseases and disorders, as described in greater detail below. In particular embodiments the invention is drawn to methods of preparing antibodies to S1P and its variants which include S1P itself {defined as sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy] phosphonic acid] (CAS 26993-30-6)}, or DHS1P {defined as dihydro sphingosine-1-phosphate [sphinganine-1-phosphate; [(2S,3R)-2-amino-3-hydroxy-octadecoxy]phosphonic acid; D-Erythro-dihydro-D-sphingosine-1-phosphate] (CAS 19794-97-9)}. Antibodies to SPC {defined as sphingosylphosphoryl choline, lysosphingomyelin, sphingosylphosphocholine, sphingosine phosphorylcholine, ethanaminium; 2-((((2-amino-3-hydroxy-4-octadecenyl)oxy)hydroxyphosphinyl)oxy)-N,N,N-trimethyl-, chloride, (R—(R*,S*-(E))), 2-[[(E,2R,3S)-2-amino-3-hydroxy-octadec-4-enoxy]-hydroxy-phosphoryl]oxyethy 1-trimethyl-azanium chloride (CAS 10216-23-6)]} may also be useful.

1. A Preferred Anti-S1P Monoclonal Antibody.

A specific monoclonal anti-S1P antibody (anti-S1P mAb) is described. This antibody can be used as a therapeutic molecular sponge to selectively absorb S1P and thereby thus lower the effective in vivo extracellular concentrations of this pro-angiogenic, pro-fibrotic and tumor-facilitating factor. This can result in the reduction of tumor volume and metastatic potential, as well as the simultaneous blockage of new blood vessel formation that otherwise can feed the growing tumor. This antibody (and molecules having an equivalent activity) can also be used to treat other hyperproliferative disorders impacted by S1P, including unwanted endothelial cell proliferation, as occurs, for example, in age-related macular degeneration as well as in many cancers. In addition, the ability of S1P to protect cells from apoptosis can be reversed by the agents such as the antibody resulting in an increase in the efficacy of standard pro-apoptotic chemotherapeutic drugs.

B. Antibodies to Other Bioactive Signaling Lipids

The methods described herein can be used to prepare monoclonal antibodies against many additional extracellular and intracellular bioactive lipids beyond sphingolipids (e.g., SPC, ceramide, sphingosine, sphinganine, S1P and dihydro-S1P). Other bioactive lipid classes include the leukotrienes, eicosanoids, eicosanoid metabolites such as the HETEs, prostaglandins, lipoxins, epoxyeicosatrienoic acids and isoeicosanoids), non-eicosanoid cannabinoid mediators, phospholipids and their derivatives such as phosphatidic acid (PA) and phosphatidylglycerol (PG), cardiolipins, and lysophospholipids such as lysophosphatidyl choline (LPC) and lysophosphatidic acid (LPA). In short, this invention can be adapted for application to any desired extracellular and/or intracellular signaling bioactive lipid with pleiotropic effects on important cellular processes. Other examples of bioactive lipids include phosphatidylinositol (PI), phosphatidylethanolamine (PEA), diacylglyceride (DG), sulfatides, gangliosides, globosides and cerebrosides.

C. Conjugates

A monoclonal antibody, or antigen-binding fragment thereof, described herein can be used alone in vitro or can be administered to a subject, in non-derivatized or non-conjugated forms. In other embodiments, such antibodies, derivatives, and variants can be derivatized or linked to one or more molecular entities. Other molecular entities include naturally occurring, recombinant, or synthetic peptides, polypeptides, and proteins, nonpeptide chemical compounds such as isotopes, small molecule therapeutics, etc. Preferred small molecules include radiolabels, fluorescent agents, and small molecule chemotherapeutic agents. Preferred proteins include growth factors, cytokines, and antibodies (including identical antibodies and derivatives or variants of such antibodies). The active ingredients can be linked by any suitable method, taking into account the active ingredients and the intended application, among other factors. For example, a monoclonal antibody of the invention can be functionally linked to another molecule by chemical coupling, genetic fusion, non-covalent association, or another suitable approach.

The invention thus envisions conjugates formed between one or more monoclonal antibodies of the invention, or a variant or derivative thereof, with another active ingredient. Such conjugates may be covalent or non-covalent, and may occur via a linker or directly between the active ingredients.

Examples of such conjugates include one or more monoclonal antibodies of the invention (or an antigen-binding domain thereof) linked to another therapeutic monoclonal antibody of the same or different class. Alternatively, the monoclonal antibody or antibody derivative or variant of the invention may be linked to a different class of therapeutic agent, for example, a small molecule chemotherapeutic agent or radioisotope. In some embodiments, one or more of each of two or more different therapeutic agents (at least one of which is a compound of the invention) can be linked through a multivalent scaffold.

As an alternative to conjugates, a monoclonal antibody or antibody derivative or variant of the invention may simply be associated with one or more different therapeutic agents. As an example, a monoclonal antibody of the invention can be combined with one or more other types of therapeutic agents in a delivery vehicle, e.g., a liposome, micelle, nanoparticle, etc., suitable for administration to a subject.

The invention also envisions conjugating a monoclonal antibody or antibody derivative or variant of the invention, for example, one or more CDRs reactive against a particular target bioactive lipid, with a protein or polypeptide. As an example, one or more CDRs from the variable region of a immunoglobulin heavy or light chain can be grafted into monoclonal antibody.

3. Applications

The invention is drawn to compositions and methods for treating or preventing hyperproliferative disorders such as cancer, fibrosis and angiogenesis, and cardiovascular, cardiac, and other diseases, disorders or physical trauma, and/or cerebrovascular diseases and disorders, in which therapeutic agents are administered to a patient that alters the activity or concentration of an undesirable, toxic and/or bioactive lipids, or precursors or metabolites thereof. The therapeutic methods and compositions of the invention act by changing the absolute, relative and/or available concentration and/or activities of certain undesirable or toxic lipids. Here, "toxic" refers to a particular lipid's involvement in a disease process, for example, as a signaling molecule.

Without wishing to be bound by any particular theory, it is believed that inappropriate concentrations of lipids such as LPA and/or their metabolites cause or contribute to the development of various diseases and disorders, including heart disease, neuropathic pain, cancer, angiogenesis, inflammation, and cerebrovascular disease, including stroke-like inner ear pathologies (see, e.g., Scherer, et al. (2006), Cardiovascular Research, vol. 70; 79-87). As such, the instant compositions and methods can be used to treat these diseases and disorders, particularly by decreasing the effective in vivo concentration of a particular target lipid, for example, LPA. Several classes of diseases that may be treated in accordance with the invention are described below.

A. Hyperproliferative Diseases and Disorders i. Cancer

One cancer therapy strategy is to reduce the biologically available extracellular levels of the tumor-promoter, S1P, either alone or in combination with traditional anti-cancer treatments, including the administration of chemotherapeutic agents, such as an anthracycline. To this end, a monoclonal antibody (mAb) has been developed that is specific for S1P, which can selectively adsorb S1P from the serum, acting as a molecular sponge to neutralize extracellular S1P. Since S1P has been shown to be pro-angiogenic, an added benefit to the antibody's effectiveness can be derived from the antibody's ability to starve the blood supply of the growing tumor. Thus, another sphingolipid-based anti-neoplastic strategy involves combining known activators of CER and SPH production (doxorubicin and related anthracycline glycosides, radiation therapy, etc.) coupled with a strategy to reduce S1P levels.

While sphingolipid-based anti-cancer strategies that target key enzymes of the sphingolipid metabolic pathway, such as SPHK, have been proposed, S1P itself has not been emphasized, largely because of difficulties in attacking this and related targets. As described herein, a highly specific monoclonal antibody to S1P has been produced that recognizes S1P in the physiological range and is capable of neutralizing S1P by molecular combination. Use of this antibody (and its derivatives) will deprive growing tumor cells of an important growth and survival factor. Moreover, use of such an antibody-based cancer therapy could also be effective when used in combination with conventional cancer treatments, such as surgery, radiation therapy, and/or the administration of cytotoxic anti-cancer agents. Examples of cytotoxic agents include, for example, the anthracycline family of drugs, the vinca alkaloids, the mitomycins, the bleomycins, the cytotoxic nucleosides, the taxanes, the epothilones, discodermolide, the pteridine family of drugs, diynenes and the podophyllotoxins. Members of those classes include, for example, doxorubicin, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives, such as etoposide, etoposide phosphate or teniposide, melphalan, vinblastine, vincristine, leurosidine, vindesine, leurosine, paclitaxel and the like. Other antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. Other cytotoxic drugs are well known in the art. An antibody-based combination therapy may improve the efficacy of chemotherapeutic agents by sensitizing cells to apoptosis while minimizing their toxic side effects, although administration of the antibody alone may also have efficacy in delaying the progression of disease. Indeed, the ability of the anti-S1P mAb to retard tumor progression in mouse models of human cancer and in allograft mouse models demonstrates the utility of anti-S1P antibody approaches in treating both human and animal tumors. Moreover, the discovery that several human cancers types (e.g., ovarian, breast, lung, and melanoma) can be treated in xenograft models demonstrates that the anti-S1P antibody approaches are not limited to one cancer cell or tissue type.

LPA mediates multiple cellular responses including cell proliferation, differentiation, angiogenesis and motility. A large body of experimental findings suggests that extracellular LPA plays a key role in the progression of several types of human cancer by stimulating tumor cell proliferation, survival, invasion and by inducing angiogenesis and metastasis. In addition, LPA protects a variety of tumor cell types from apoptosis. LPA has long been associated with ovarian and breast cancer [Fang, X., et al., (2002) Biochim Biophys Acta, 1582: 257-64]; elevated levels of LPA have been found in both blood and ascites of patients and have been correlated with tumor progression, angiogenesis and metastatic potential. Furthermore, autotoxin (ATX), the enzyme primarily responsible for LPA production, has been correlated with the metastatic and invasive properties of human tumors including melanoma, lung cancer, neuroblastoma, hepatocellular carcinoma, and glioblastoma multiforme. Thus LPA is recognized to be an innovative and promising target for cancer therapy [Mills, G. B. and W. H. Moolenaar (2003) Nat Rev Cancer, 3: 582-91].

It is believed that neutralizing LPA with anti-LPA antibody (such as that disclosed herein) will be a novel anti-angiogenic and anti-metastatic therapeutic approach in the treatment of cancer. Monoclonal antibodies against LPA are believed to act as a "sponge" to selectively bind LPA and thereby lower the effective in vivo extracellular levels of LPA. This is believed to result in the reduction of tumorigenesis and tumor growth as well as the simultaneous blockage of blood vessel formation and the metastatic potential. In addition, the ability of LPA to protect cells from apoptosis is likely to be lost as a result of antibody neutralization, thus increasing the efficacy of standard pro-apoptotic chemotherapeutic drugs.

ii. Angiogenesis

Angiogenesis is the process by which new blood vessels are formed from existing blood vessels. The angiogenesis associated with solid and circulating tumors is now considered to be a crucial component of tumorigenesis, as today the view that tumor growth is dependent upon neovascularization is scientifically well accepted. Both S1P and LPA appear important to the angiogenic process.

LPA is the primary regulator of GROα, an oncogene believed to contribute to tumorigenesis through its pro-angiogenic effect (Lee, et al (2006), Cancer Res, vol. 66: 2740-8). LPA also enhances expression of matrix metalloproteinase-2, a recognized player in the cell migration underlying the angiogenic process (Wu, et al. (2005), Endocrinology, vol. 146: 3387-3400).

S1P stimulates DNA synthesis and chemotactic motility of human venous endothelial cells (HUVECs), while inducing differentiation of multicellular structures essential early blood vessel formation. S1P also promotes the migration of bone marrow-derived endothelial cell precursors to neovascularization sites, and cells that over-express S1P receptors are resistant the anti-angiogenic agents, thalidomide and Neovastat. Thus, S1P, and particularly S1 receptors, are required for angiogenesis and neovascularization. Finally, cross-talk occurs between S1P and other pro-angiogenic growth factors such as VEGF, EGF, PDGF, bFGF, and IL-8. For example, S1P transactivates EGF and VEGF2 receptors, and VEGF up-regulates S1P receptor expression (Igarashi, et al. (2003), PNAS (USA), vol. 100: 10664-10669).

As will be appreciated, clinical control of angiogenesis is a critical component for the treatment of cancer and other angiogenesis-dependent diseases such as age-related macular degeneration (AMD) and endometriosis. Anti-angiogenic therapeutics are also particularly attractive because the vascular endothelial cells that are involved in tumor angiogenesis do not mutate as easily as do cancer cells; consequently, vascular endothelial cells are less likely than cancer cells to gain resistance to prolonged therapy, making them useful therapeutic targets.

There are several lines of evidence suggesting that S1P is a potentially significant pro-angiogenic growth factor that may be important in tumor angiogenesis, including that: anti-S1P antibodies can neutralize S1P-induced tube formation, migration of vascular endothelial cells, and protection from cell death in various in vitro assays using HUVECs; injection of breast adenocarcinoma MCF-7 cells expressing elevated S1P levels into mammary fat pads of nude mice results in an increase of angiogenesis-dependent tumors that are both larger and more numerous than when control cells are used; anti-S1P antibodies can dramatically reduce tumor-associated angiogenesis in an orthotopic murine melanoma allograft model; S1P increases new capillary growth into Matrigel plugs implanted in mice, an effect that can be neutralized by the systemic administration of anti-S1P antibodies; in vivo administration of anti-S1P antibodies can completely neutralize pro-angiogenic growth factor-induced angiogenesis (e.g., by bFGF and VEGF) in murine Matrigel plug assays; S1P stimulates the release of bFGF and VEGF from tumor cells in vitro and in vivo, an effect that can be reversed by anti-S1P antibodies; S1P enhances in vitro motility and invasion of a large number of different types of cancer cells, including glioblastoma multiforme cells; and anti-S1P antibodies significantly reduce the neovascularization associated with animal models of AMD.

The importance of S1P in the angiogenic-dependent tumors makes S1P an excellent target for cancer treatment. Indeed, antibody neutralization of extracellular S1P may result in a marked decrease in cancer progression in mammals, including humans, as a result of inhibition of blood vessel formation with concomitant loss of the nutrients and oxygen needed to support tumor growth. Thus, anti-S1P antibodies have several mechanisms of action, including: (1) direct effects on tumor cell growth; (2) indirect anti-angiogenic effects on vascular endothelial cells; and (3) the indirect anti-angiogenic effects that prevent the release and action of other pro-angiogenic growth factors. Accordingly, anti-S1P antibodies can also serve as anti-metastatic therapeutics, in addition to providing anti-angiogenic therapy.

Control of angiogenesis is a critical component for the treatment of other angiogenesis-dependent diseases besides cancer, such as age-related macular degeneration, retinopathy of prematurity, diabetic retinopathy, endometriosis, and rheumatoid arthritis (Carmeliet, P. (2005), Nature, vol. Vol. 438 (15): 932-6).

Anti-angiogenic therapeutics are also particularly attractive because the vascular endothelial cells that are involved in tumor angiogenesis do not mutate as easily as do cancer cells; consequently, vascular endothelial cells are less likely than cancer cells to gain resistance to prolonged therapy, making them useful therapeutic targets. S1P antibodies, and derivatives thereof, will also be useful in treating other hyperproliferative disorders associated with S1P activity, such as those cause by aberrant endothelial cell proliferation, as occurs with the angiogenesis associated with AMD.

iii. Fibrogenesis and Scarring (a) S1P, Fibroblasts, and the Remodeling Process

It is clear that cardiac fibroblasts, particularly myofibroblasts, are key cellular elements in scar formation in response to the cell death and inflammation of a myocardial infarction (MI). Myofibroblast collagen gene expression is a hallmark of remodeling and necessary for scar formation. In addition to its other activities, S1P is also an inflammatory mediator that makes profound contributions to wound healing by activating fibroblast migration and proliferation, in addition to activating platelets, stimulating angiogenesis, and promoting smooth muscle function. Thus, S1P, perhaps produced locally by injured myocardium, could, in part, be responsible for the maladaptive wound healing associated with cardiac remodeling and failure, particularly by activating myofibroblasts in the heart.

There are three general responses of cells to S1P: protection from cell death; stimulation of proliferation; and the promotion of migratory responses. Accordingly, S1P activity or involvement with a particular disorder, cell line, etc. can be assessed by adapting assays of this sort for this purpose. There is evidence that fibroblasts respond to S1P in all three ways to promote wound healing. For instance, in several of the examples in the Example section below, evidence is presented that demonstrates that S1P contributes to remodeling by promoting cardiac myofibroblast activity (proliferation, migration, and collagen gene expression).

Anti-S1P antibodies or antibody derivatives will also prevent excess scarring associated with surgical procedures. Excess scarring post injury or surgery, a problem in adult but not fetal skin tissue (Adzick and Lorenz (1994), Ann Surg, vol. 220: 10-18), is attributed to excess TGF-β in adult skin tissue post injury. S1P has been implicated as a potent activator the TGF-β signaling system. Accordingly, an antiS1P antibody would be expected to limit excess scarring post injury or surgery.

(b) Protection from Cell Death by LPA and S1P

LPA is an agent that protects cancer cells from apoptosis. Thus, as discussed in detail above, an antibody to LPA, for example, will make cancer cells more susceptible to chemotherapy. This has, in fact, been demonstrated in the examples hereinbelow, using newly developed anti-LPA monoclonal antibodies.

As is the case for many cell types, fibroblasts are directly protected from apoptosis by addition of S1P, and apoptosis is enhanced by inhibitors of SPHK, and S1P blocks cytochrome C release and the resultant caspase activation. Further, fibroblasts transfected with SPHK1 exhibit protection from apoptosis, an effect that may depend upon translocation of SPHK1 to the plasma membrane. It is well-established that SPHK1 up-regulates Akt, thereby regulating Bcl-2 family members and protecting from apoptosis. Also, S1P$_3$ is required for Akt phosphorylation in mouse embryonic fibroblasts (MEFs). Also, up-regulation of SPHK and resulting increases in S1P levels protect cardiofibroblasts from apoptosis.

Ceramide, an upstream metabolite of S1P, decreases mitochondrial membrane potential coincident with increasing the transcription of death inducing mitochondrial proteins. Because of the rheostat mechanism, S1P may have the opposite effect and protect cardiac myofibroblasts (i.e., fully differentiated fibroblasts in the heart) from apoptosis. Indeed, S1P may even activate autophagy as a protection mechanism. These effects could be reversed by the neutralizing anti-S1P antibodies (or other molecules that bind and act to sequester S1P).

B. Pain

Bioactive lipids are believed to play important roles in the pathogenesis of pain, including neuropathic pain and pain associated with chemotherapy.

The significant role of LPA signaling in the development of neuropathic pain was established using various pharmacological and genetic approaches, including the use of mice lacking the LPA1 receptor (see. e.g., Ueda, et al. (2006), Pharmacol Ther, vol. 109: 57-77; Inoue, et al. (2004), Nat. Med., vol. 10: 712-8). Wild-type animals with nerve injury develop behavioral allodynia and hyperalgesia paralleled by demyelination in the dorsal root and increased expression of both the protein kinase C isoform within the spinal cord dorsal horn and the 21 calcium channel subunit in dorsal root ganglia. Intrathecal injection of LPA induced behavioral, morphological and biochemical changes similar to those observed after nerve ligation. In contrast, mice lacking a single LPA receptor (LPA-1, also known as EDG-2) that activates the Rho-Rho kinase pathway do not develop signs of neuropathic pain after peripheral nerve injury. Inhibitors of Rho and Rho kinase also prevented these signs of neuropathic pain. These results imply that receptor-mediated LPA signaling is crucial in the initiation of neuropathic pain and that an antibody to LPA would likely alleviate neuropathic pain in individuals suffering this condition [Moulin, Del. (2006), Pain Res Manag, vol. 11, Suppl A: 30A-6A].

In the context of other pain, that associated with chemotherapy is a major dose limiting toxicity of many small molecule chemotherapeutic agents. Indeed, many cases of chemotherapy-induced pain have been reported. For instance, Paclitaxel (Taxol), an anti-neoplastic agent derived from the Pacific yew tree *Taxus brevifolia*), is used to treat a variety of cancers, including ovarian, breast, and non-small cell lung cancer. Paclitaxel's effectiveness, however, is limited by the highly incidental development of severe painful peripheral neuropathy such as numbness and burning pain. A monoclonal antibody against a bioactive lipid correlated with such pain, for example, LPA (or a derivative of such an antibody that contains a lipid-binding portion thereof), could be administered in combination with Paclitaxel in order to reduce the pain associated with the chemotherapeutic agent. As a result of ameliorating this dose-limiting toxicity, the amount of Paclitaxel to be administered could be even higher (and thus even more effective) when used in combination with such a monoclonal antibody or antibody derivative. In some embodiments, the chemotherapeutic agent (or other drug) could be conjugated to or otherwise associated with the antibody or antibody derivative, for example, by covalently linking the small molecule chemotherapeutic agent to the antibody, by linking the small molecule chemotherapeutic to a multivalent scaffold to which is also linked a monoclonal antibody or at least one bioactive lipid binding domain derived from a monoclonal antibody specifically reactive against the target bioactive lipid, etc.

C Cardiovascular Diseases and Disorders

Ischemic heart disease is the leading cause of death in the U.S. Each year approximately 1.5 million people suffer heart attacks (myocardial infarctions), of which about one-third (i.e., about 500,000) are fatal. In addition, about 6.75 million Americans suffer from angina pectoris, the most common manifestation of cardiac ischemia. In total, there are more than 13 million patients living with ischemic heart disease in the U.S. alone. "Ischemia" is a condition associated with an inadequate flow of oxygenated blood to a part of the body, typically caused by the constriction or blockage of the blood vessels supplying it. Ischemia occurs any time that blood flow to a tissue is reduced below a critical level. This reduction in blood flow can result from: (i) the blockage of a vessel by an embolus (blood clot); (ii) the blockage of a vessel due to atherosclerosis; (iii) the breakage of a blood vessel (a bleeding stroke); (iv) the blockage of a blood vessel due to acute vasoconstriction; (v) a myocardial infarction (when the heart stops, the flow of blood to organs is reduced, and ischemia results); (vi) trauma; (vii) surgery, during which blood flow to a tissue or organ needs to be reduced or stopped to achieve the aims of surgery (e.g., angioplasty, heart and lung/heart transplants); (viii) exposure to certain agents, e.g., dobutamine or adenosine (Lagerqvist, et al. (1992), Br. Heart J., vol. 68:282-285); or (ix) anti-neoplastic and other chemotherapeutic agents, such as doxorubicin, that are cardiotoxic.

Even if the flow rate (volume/time) of blood is adequate, ischemia may nonetheless occur due to hypoxia, i.e., a condition in which the oxygen content of blood is insufficient to satisfy normal cellular oxygen requirements of the affected area(s). Hypoxic blood is, by definition, distinct from normoxic blood, i.e., blood in which the oxygen content is sufficient to satisfy normal cellular oxygen requirements. Hypoxic conditions may result from, but are not limited to, forms of heart failure that adversely affect cardiac pumping such as hypertension, arrhythmias, septic shock, trauma, cardiomyopathies, and congestive heart disease.

Myocardial ischemic disorders occur when cardiac blood flow is restricted (ischemia) and/or when oxygen supply to the heart muscle is compromised (hypoxia) such that the heart's demand for oxygen is not met by the supply. Coronary artery disease (CAD) arising from arteriosclerosis, particularly atherosclerosis, is the most common cause of ischemia, and has symptoms such as stable or unstable angina pectoris. CAD can lead to acute myocardial infarctions (AMI) and sudden cardiac death. The spectrum of ischemic conditions that results in heart failure is referred to as Acute Coronary Syndrome (ACS). Reperfusion injury is often a consequence of ischemia, in particular when anti-coagulants, thrombolytic agents, or anti-anginal medications are used or when the cardiac vasculature is surgically opened by angioplasty or by coronary artery grafting.

Presently, treatments for acute myocardial infarction and other cardiac diseases include, but are not limited, to mechanical devices and associated procedures therewith, e.g., coronary angioplasty; thrombolytic agents such as streptokinase, tPA, and derivatives thereof. Adjuvants to these therapies include beta-blockers, aspirin and heparin, and glycoprotein (GP) IIb/IIIa inhibitors. GP IIb/IIIa inhibitors decrease platelet aggregation and thrombus formation. Examples include monoclonal antibodies (e.g., abciximab), cyclic peptides (e.g., eptifibatide), and nonpeptide peptidomimetics (e.g., tirofiban, lamifiban, xemilofiban, sibrafiban, and lefradafibian).

Preventive treatments include those that reduce a patient's cholesterol levels by, e.g., diet management and pharmacological intervention. Statins are one type of agent used to reduce cholesterol levels. Statins are believed to act by inhibiting the activity of HMG-CoA reductase, which in turn increases the hepatic production of cholesterol receptors. Hepatic cholesterol receptors bind cholesterol and remove it from blood. Such agents include lovastatin, simvastatin, pravastatin, and fluvastatin. These and other statins slow the progression of coronary artery disease, and may induce regression of atherosclerotic lesions in patients, although the range of side effects from the use of such drugs is not fully understood.

As will be appreciated, monoclonal antibodies and derivatives, and other fragments and variants reactive against a bioactive lipid may be used to effect cardiac therapy, alone or in combination with other therapeutic approaches, including treatment with drugs and/or surgery. Here, "cardiac therapy" refers to the prevention and/or treatment of myocardial diseases, disorders, or physical trauma, including myocardial ischemia, AMI, CAD, and ACS, as well as trauma or cardiac cell and tissue damage that may occur during or as a consequence of interventional cardiology or other surgical or medical procedures or therapies that may cause ischemic or ischemic/reperfusion damage in mammals, particularly humans.

Besides the heart and brain, an anti-S1P approach can also be applied to other vascular-based, stroke-like conditions such as various inner ear pathologies (Scherer, et al. (2006), Cardiovasc Res, vol. 70:79-87).

D. Cerebrovascular Diseases and Disorders

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either focal or global. Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Global cerebral ischemia refers to reduction of blood flow within the cerebral vasculature resulting from systemic circulatory failure, which promptly leads to a reduction in oxygen and nutrients to tissues. Thus, global cerebral ischemia results from severe depression of cardiac performance, and is most frequently caused by AMI, although bother causes include pump failure resulting from acute myocarditis or depression of myocardial contractility following cardiac arrest or prolonged cardiopulmonary bypass; mechanical abnormalities, such as severe valvular stenosis, massive aortic or mitral regurgitation, and acutely acquired ventricular septal defects; as well as from cardiac arrhythmia, such as ventricular fibrillation, or from interventional procedures, such as carotid angioplasty, stenting, endarterectomy, cardiac catheterization, electrophysiologic studies, and angioplasty.

Ischemic injury post stroke and/or MI typically leads to cell death by depolarization of critical cells with resulting rise in intracellular $Na^+$ and $Ca^{++}$ followed by cell death. One channel controlling this process is the Transient Receptor Potential Protein, a non-voltage dependent channel and recently S1P was identified as an activator of this channel through a GPCR-dependent mechanism. In addition, Transient Receptor Potential Protein, sphingosine kinase 1 and sphingokinase 2 share promoter regions with Egr-1, an important master switch believed to regulate cardiovascular pathobiology (Khachigian, L M (2006), Circ Res, vol. 98: 186-91) and Sp1, a transcription factor that plays a critical role in the death of neural cells (Simard, et al. (2006), Nat Med., vol. 12: 433-40). Based on these findings, an antibody to S1P would be expected to mitigate cell death caused by ischemia post hypoxia.

Those skilled in the art are easily able to identify patients having a stroke or at risk of having a stroke, cerebral ischemia, head trauma, or epilepsy. For example, patients who are at risk of having a stroke include those having hypertension or undergoing major surgery. Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. In some circumstances, the ischemia resolves itself over a period of time due to the fact that some thrombi get absorbed into the circulation, or fragment and travel distally over a period of a few days. Tissue plasminogen activator (t-PA) or has been approved for treating acute stroke, although such systemic treatment has been associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

As will be appreciated, antibodies, antibody-derivatives, and other immune-derived moiety reactive against a bioactive lipid may be used to effect cerebrovascular therapy, alone or in combination with other therapeutic approaches, including treatment with drugs and/or surgery. Here, "cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, as well as trauma or surgical or medical procedures or therapies that may cause ischemic or ischemic/reperfusion cerebrovascular damage in mammals, particularly humans.

E. Diagnostic and Theranostic Applications for Antibodies that Bind Bioactive Lipids As the role of various bioactive lipids in disease is elucidated, new roles for antibody binders of bioactive lipids in diagnostics and theranostics may also be envisioned. According to the instant invention, methods are provided for enhanced detection of bioactive lipids using derivatized lipids bound to a solid support. In addition to use of these detection methods in antibody production and characterization and in research, enhanced detection of bioactive lipids may also provide a valuable diagnostic approach for diseases associated with bioactive lipids. When combined with other techniques, a theranostic approach for designing optimal patient treatment is provided. One nonlimiting example is use of anti-S1P antibodies in diagnostic and theranostic methods relating to the role of S1P as a biomarker for cancer. Diagnostic and theranostic methods using antibodies targeted to LPA or other bioactive lipids, and for other disease indications, are also envisioned.

Recently, scientific literature has suggested that S1P is a potent tumorigenic growth factor that is likely released from tumor cells, and that S1P may be a novel biomarker for early-stage cancer detection. SPHK, the enzyme which is responsible for the production of S1P, is significantly up-regulated in a variety of cancer types (French, Schrecengost et al. 2003). SPHK activity is up-regulated 2-3 fold in malignant breast, colon, lung, ovarian, stomach, uterine, kidney and rectal cancer when compared to adjacent normal tissue. These workers also showed that SPHK expression varies from patient to patient, suggesting that the tumors of some patients might be more dependent on S1P than those of other patients with the same tumor type. Searching commercially available genomics database (ASCENTA, Genelogic Inc., Gaithersburg Md.) confirms that the relative expression of SPHK is, in general, significantly elevated in a wide variety of malignant tumors.

Recent publications have also suggested that S1P may be a novel cancer biomarker [Xu, Y. et al., (1998) JAMA 280: 719-723; Shen, Z. et al., (2001) Gynecol Oncol 83: 25-30; Xiao, Y. J. et al., (2001) Anal Biochem 290(2): 302-13; Sutphen (2004) Cancer Epidemiology 13(7) 1185-91]. For example, Sutphen et al, have shown that serum S1P levels are elevated in early-stage ovarian cancer patients (Sutphen 2004). One might predict from the data that breast cancer patients might also demonstrate some variability in their dependence on S1P. Taken together, these preliminary observations suggest that the success of an anti-S1P therapeutic, e.g., an anti-S1P mAb therapeutic, might be predicted for an individual patient if that patient's biopsy tissue, blood, urine or other tissue or fluid sample show elevated S1P levels.

The potential use of S1P in biological fluids has been disclosed in the following patents, all of which are commonly assigned with the instant application. U.S. Pat. No. 6,534,323, U.S. Pat. No. 6,534,322; U.S. Pat. No. 6,210,976; U.S. Pat. No. 6,858,383; U.S. Pat. No. 6,881,546; U.S. Pat. No. 7,169,390 and U.S. Pat. No. 6,500,633.

Even though humanized antibodies have low toxicity and large therapeutic indices, they are quite costly to the patient and to health care providers. Thus directing utility of the anti-S1P mAb therapeutic to those who would most likely respond to this treatment would lower risks and minimize costs, while providing optimum patient benefit.

Outlined below are a few proposed applications of biolipid diagnostics and theranostics for improved disease management.

1. S1P may be used as a biomarker to predict individual patient therapeutic efficacy especially when combined with sphingolipid-based genomics. Based on recent findings, we would predict that S1P dependent tumors may produce their own S1P in addition to the abundant serum source of S1P. Highly aggressive tumors utilize a strategy of producing their own growth factors, and we suggest that S1P is one of the growth factors. Therefore, serum, plasma or urine measurements of total S1P from individual patients would be one predictor of patient outcome. Moreover, S1P production would be concentrated in the tumor itself and in the tumor microenvironment (e.g., interstitial fluid). Example 11 hereinbelow describes the use of an anti-S1P mAb in an immunohistochemical method of a tumor section to assess S1P production by the tumor itself. Up-regulation of SPHK may prove useful, but since the kinase is an enzyme, it is believed that the signal as measured by S1P production will be much higher than if one relied on RNA or protein expression of the kinase itself. In addition, it is hypothesized that patients whose tumors have an up-regulation of S1P-receptors and SPHK expression are more likely to have tumors that rely on S1P as a growth factor. It is believed that these patients would benefit most from our putative anti-S1P mAb therapy. Therefore, bioassays from biopsy tissue analyzed by quantitative-PCR for the relative expression of S1P receptors and SPHK would provide a strong theranostic platform. This theranostic platform would consist of serum S1P marker analysis in combination with the genomic or proteomic quantification of S1P-related protein markers as surrogate markers of disease. This novel multi-marker analysis would provide a very strong platform for prediction of individual responsiveness to an anti-S1P mAb (SPHINGOMAB™)-based therapy.

2. S1P may be used as a surrogate marker to titrate therapeutic regimen. The concentration of serum S1P from patients being treated with the anti-S1P mAb has the potential to be used as a surrogate marker for evaluating the course of treatment. An ELISA-based platform using patient serum, plasma or urine samples will allow for the accurate measurement of the S1P biomarker levels and to determine more precisely the anti-S1P mAb dosing regimen for individuals. Surrogate marker levels could be used in combination with the standard clinical endpoints to determine efficacy of the medical regimen.

3. S1P may be used as a screening tool for the early detection of cancer. The early detection of cancer is of concern due to the strong correspondence of stage of progression and success of therapy. Stage I of ovarian cancer is very difficult to detect due to the fact that majority of patients are asymptomatic. By the time ovarian cancer is diagnosed, most patients are in the later stages of the disease. Detection at an earlier stage has obvious benefits to patient outcome. As described above, ovarian cancer patient serum contains a 2-fold elevation of S1P, and this elevation is easily detectable with our current ELISA platform. Since many solid tumor types, including ovarian cancer, exhibit elevated SPHK expression, it is presumed that many of the patients with these cancers would display elevated blood and/or urine S1P that could allow the clinician to intervene earlier in disease progression.

Derivatized bioactive lipids described herein can also be used to detect the level of antibodies in a fluid or tissue sample of a patient. Without being limited by the following, such immunoassays that detect the presence of anti-sphingolipid antibodies in blood and can be used to indirectly test for increased sphingolipids in patients with chronic ischemic conditions, cancer or autoimmune disorders such as multiple sclerosis. This assay is based on the assumption that patients produce anti-sphingolipid antibodies as a consequence of elevated blood levels of sphingolipids by analogy to the anti-lactosylsphingosine antibodies observed in patients with colorectal cancer (Jozwiak W. & J. Koscielak, *Eur. J. Cancer Clin. Oncol.* 18:617-621, 1982) and the anti-galactocerebroside antibodies detected in the sera of leprosy patients (Vemuri N. et al., *Leprosy Rev.* 67:95-103, 1996).

F. Research

The bioactive signaling lipid targets of the invention are readily adaptable for use in high-throughput screening assays for screening candidate compounds to identify those which have a desired activity, e.g., inhibiting an enzyme that catalyzes a reaction that produces an undesirable bioactive signaling lipid, or blocking the binding of a bioactive signaling lipid to a receptor therefore. The compounds thus identified can serve as conventional "lead compounds" or can themselves be used as therapeutic agents. The methods of screening of the invention comprise using screening assays to identify, from a library of diverse molecules, one or more compounds having a desired activity. A "screening assay" is a selective assay designed to identify, isolate, and/or determine the structure of, compounds within a collection that have a pre-selected activity. The collection can be a traditional combinatorial libraries are prepared according to methods known in the art, or may be purchased commercially and may be a wide-range of organic structures or structures pre-selected for potential bioactive signaling activity. By "identifying" it is meant that a compound having a desirable activity is isolated, its chemical structure is determined (including without limitation determining the nucleotide and amino acid sequences of nucleic acids and polypeptides, respectively) the structure of, and, additionally or alternatively, purifying compounds having the screened activity. Biochemical and biological assays are designed to test for activity in a broad range of systems ranging from protein-protein interactions, enzyme catalysis, small molecule-protein binding, to cellular functions. Such assays include automated, semi-automated assays and high throughput screening assays.

EXAMPLES

The invention will be further described by reference to the following detailed examples. These Examples are in no way to be considered to limit the scope of the invention in any manner.

Example 1

Synthetic Scheme for Making a Representative Thiolated Analog of S1P

Figure 1B:
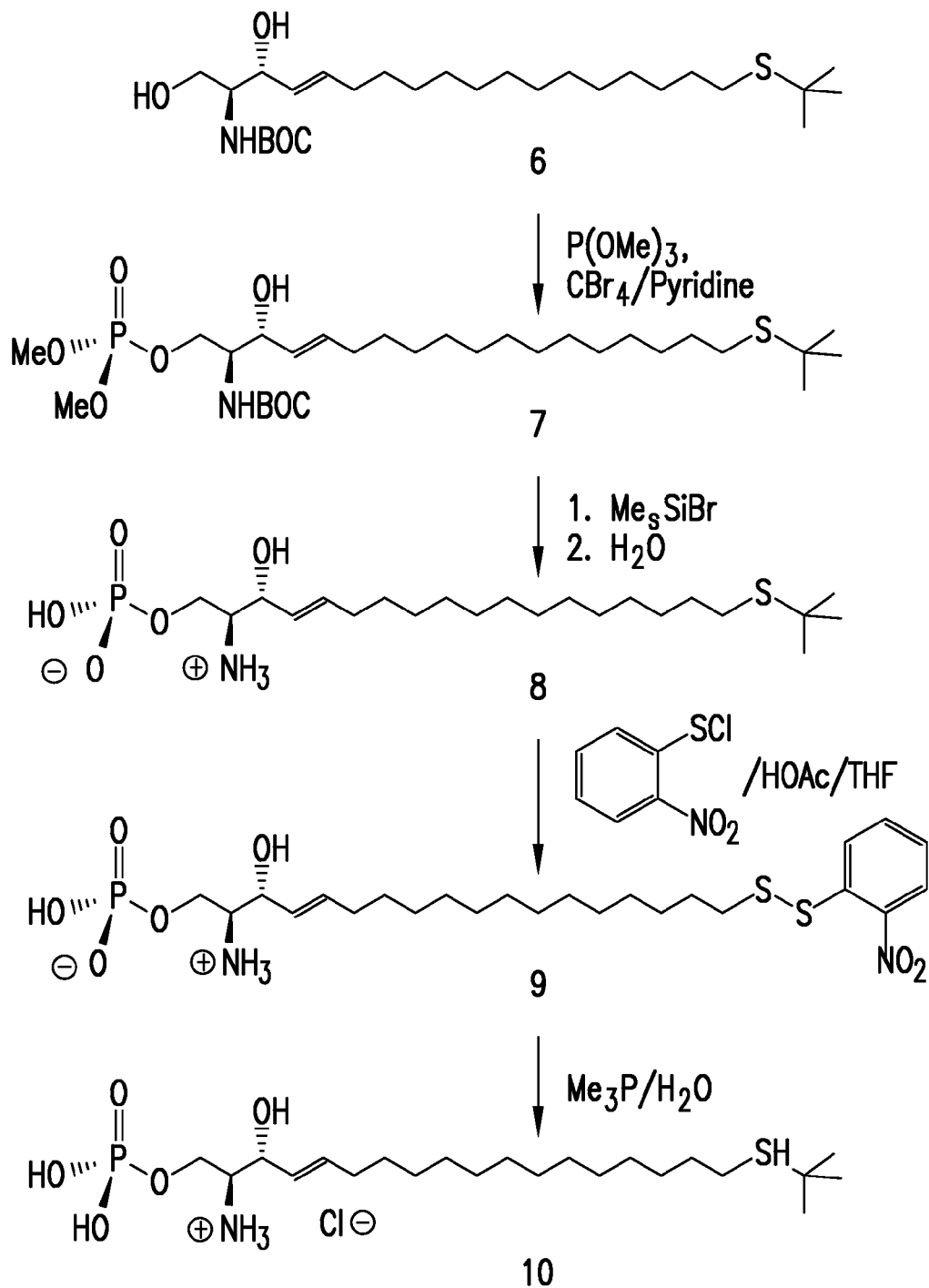
FIGS. 1b and 1c are continuations of FIG. 1a showing the remainder of the same synthetic scheme.
Figure 1C:
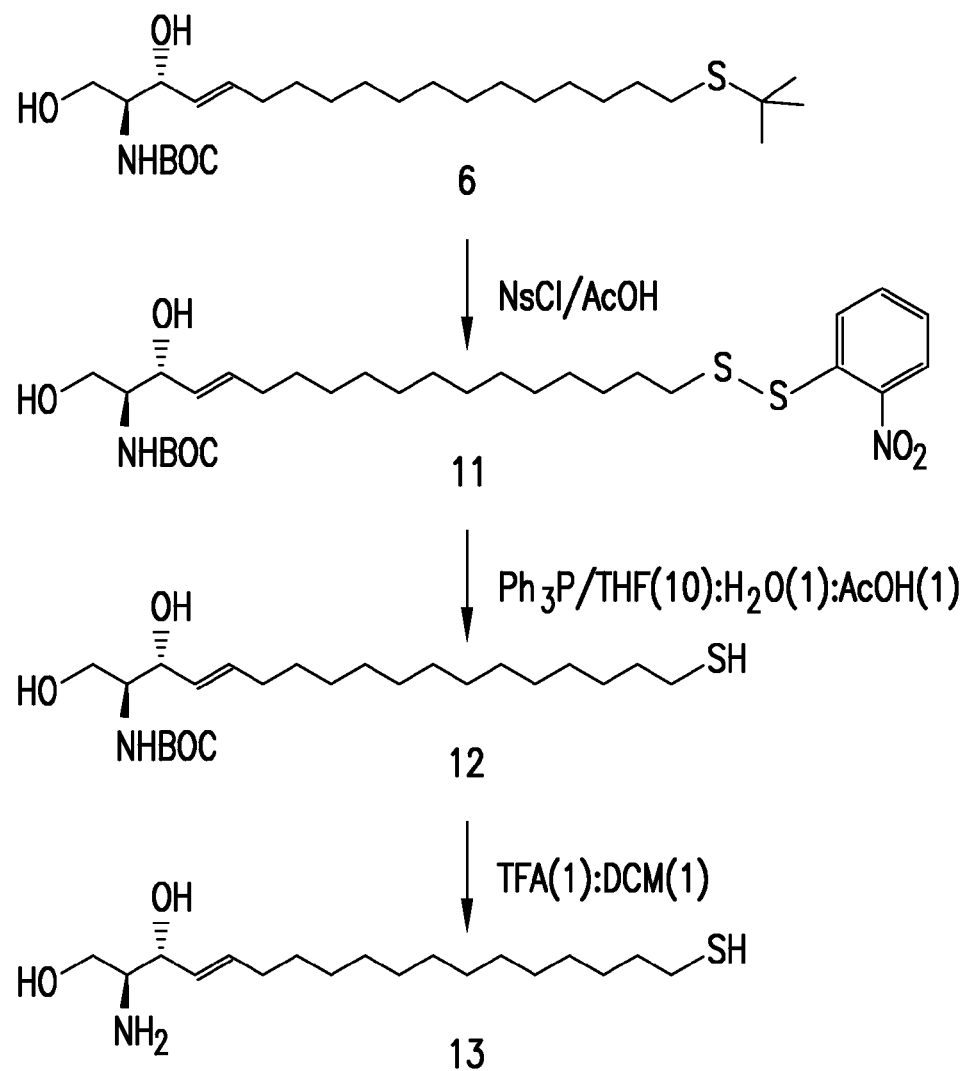

The synthetic approach described in this example results in the preparation of an antigen by serial addition of structural elements using primarily conventional organic chemistry. A scheme for the approach described in this example is provided in FIG. 1, and the compound numbers in the synthetic description below refer to the numbered structures in FIG. 1.

This synthetic approach began with the commercially available 15-hydroxyl pentadecyne, 1, and activation by methyl sulphonyl chloride of the 15-hydroxy group to facilitate hydroxyl substitution to produce the sulphonate, 2. Substitution of the sulphonate with t-butyl thiol yielded the protected thioether, 3, which was condensed with Garner's aldehyde to produce 4. Gentle reduction of the alkyne moiety to an alkene (5), followed by acid catalyzed opening of the oxazolidene ring yielded S-protected and N-protected thiol substituted sphingosine, 6. During this last step, re-derivatization with di-t-butyl dicarbonate was employed to mitigate loss of the N-BOC group during the acid-catalyzed ring opening.

As will be appreciated, compound 6 can itself be used as an antigen for preparing haptens to raise antibodies to sphingosine, or, alternatively, as starting material for two different synthetic approaches to prepare a thiolated S1P analog. In one approach, compound 6 phosphorylation with trimethyl phosphate produced compound 7. Treatment of compound 7 with trimethylsilyl bromide removed both methyl groups from the phosphate and the t-butyloxycarbonyl group from the primary amine, leaving compound 8 with the t-butyl group on the sulfur as the only protecting group. To remove this group, the t-butyl group was displaced by NBS to form the disulfide, 9, which was then reduced to form the thiolated S1P analog, 10.

Another approach involved treating compound 6 directly with NBSCl to form the disulfide, 11, which was then reduced to form the N-protected thiolated S1P analog, 12. Treatment of this compound with mild acid yielded the thiolated sphingosine analog, 13, which can be phosphorylated enzymatically with, e.g., sphingosine kinase, to yield the thiolated S1P analog, 10.

Modifications of the presented synthetic approach are possible, particularly with regard to the selection of protecting and de-protecting reagents, e.g., the use of trimethyl disulfide triflate described in Example 3 to de-protect the thiol.

Compound 2.

DCM (400 mL) was added to a 500 mL RB flask charged with 1 (10.3 g, 45.89 mmol), and the resulting solution cooled to 0° C. Next, TEA (8.34 g, 82.60 mmol, 9.5 mL) was added all at once followed by MsCl (7.88 g, 68.84 mmol, 5.3 mL) added drop wise over 10 min. The reaction was allowed to stir at RT for 0.5 h or until the disappearance of starting material ($R_f$=0.65, 5:1 hexanes:EtOAc). The reaction was quenched with $NH_4Cl$ (300 mL) and extracted (2×200 mL) DCM. The organic layers were dried over $MgSO_4$, filtered and the filtrate evaporated to a solid (13.86 g, 99.8% yield). $^1H$ NMR ($CDCl_3$) δ 4.20 (t, J=6.5 Hz, 2H), 2.98 (s, 3H), 2.59 (td, J=7 Hz, 3 Hz, 2H), 1.917 (t, J=3 Hz, 1H), 1.72 (quintet, J=7.5 Hz, 2H), 1.505 (quintet, J=7.5 Hz, 2H), 1.37 (br s, 4H), 1.27 (br s, 14H). $^{13}C\{^1H\}$ NMR ($CDCl_3$) δ 85.45, 70.90, 68.72, 46.69, 38.04, 30.22, 30.15, 30.14, 30.07, 29.81, 29.76, 29.69, 29.42, 29.17, 26.09, 19.06, 9.31. The principal ion observed in a HRMS analysis (ES-TOF) of compound 2 was m/z=325.1804 (calculated for $C_{16}H_{30}O_3S$: $M+Na^+$ 325.1808).

Compound 3.

A three-neck IL RB flask was charged with t-butylthiol (4.54 g, 50.40 mmol) and THF (200 mL) and then placed into an ice bath. n-BuLi (31.5 mL of 1.6 M in hexanes) was added over 30 min. Next, compound 2 (13.86 g, 45.82 mmol), dissolved in THF (100 mL), was added over 2 min. The reaction is allowed to stir for 1 hour or until starting material disappeared ($R_f$=0.7, 1:1 hexanes/EtOAc). The reaction was quenched with saturated $NH_4Cl$ (500 mL) and extracted with $EtO_2$ (2×250 mL), dried over $MgSO_4$, filtered, and the filtrate evaporated to yield a yellow oil (11.67 g, 86% yield). $^1H$ NMR ($CDCl_3$) δ 2.52 (t, J=7.5 Hz, 2H), 2.18 (td, J=7 Hz, 2.5 Hz, 2H), 1.93 (t, J=2.5 Hz, 1H), 1.55 (quintet, J=7.5 Hz, 2H), 1.51 (quintet, J=7 Hz, 2H), 1.38 (br s, 4H), 1.33 (s, 9H), 1.26

(s, 14H). $^{13}C\{^1H\}$ NMR (CDCl$_3$) δ 85.42, 68.71, 68.67, 54.07, 42.37, 31.68, 30.58, 30.28, 30.26, 30.19, 30.17, 29.98, 29.78, 29.44, 29.19, 29.02, 19.08.

Compound 4.

A 250 mL Schlenk flask charged with compound 3 (5.0 g, 16.85 mmol) was evacuated and filled with nitrogen three times before dry THF (150 mL) was added. The resulting solution cooled to −78° C. Next, n-BuLi (10.5 mL of 1.6M in hexanes) was added over 2 min. and the reaction mixture was stirred for 18 min. at −78° C. before the cooling bath was removed for 20 min. The dry ice bath was returned. After 15 min., Garner's aldehyde (3.36 g, 14.65 mmol) in dry THF (10 mL) was then added over 5 min. After 20 min., the cooling bath was removed. Thin layer chromatography (TLC) after 2.7 hr. showed that the Garner's aldehyde was gone. The reaction was quenched with saturated aqueous NH$_4$Cl (300 mL) and extracted with Et$_2$O (2×250 mL). The combined Et$_2$O phases were dried over Na$_2$SO$_4$, filtered, and the filtrate evaporated to give crude compound 4 and its syn diastereomer (not shown in FIG. 1) as a yellow oil (9.06 g). This material was then used in the next step without further purification.

Compound 5.

To reduce the triple bond in compound 4, the oil was dissolved in dry Et$_2$O (100 mL) under nitrogen. RED-Al (20 mL, 65% in toluene) was slowly added to the resulting solution at RT to control the evolution of hydrogen gas (H$_2$). The reaction was allowed to stir at RT overnight or when TLC showed the disappearance of the starting material (R$_f$=0.6 in 1:1 EtOAc:hexanes) and quenched slowly with cold MeOH or aqueous NH$_4$Cl to control the evolution of H$_2$. The resulting white suspension was filtered through a Celite pad and the filtrate was extracted with EtOAc (2×400 mL). Combined EtOAc extracts were dried over MgSO$_4$, filtered, and the filtrate evaporated to leave crude compound 5 and its syn diastereomer (not shown in FIG. 1) as a yellow oil (7.59 g).

Compound 6.

The oil containing compound 5 was dissolved in MeOH (200 mL), PTSA hydrate (0.63 g) was added, and the solution stirred at RT for 1 day and then at 50° C. for 2 days, at which point TLC suggested that all starting material (5) was gone. However, some polar material was present, suggesting that the acid had partially cleaved the BOC group. The reaction was worked up by adding saturated aqueous NH$_4$Cl (400 mL), and extracted with ether (3×300 mL). The combined ether phases were dried over Na$_2$SO$_4$, filtered, and the filtrate evaporated to dryness, leaving 5.14 g of oil. In order to re-protect whatever amine had formed, the crude product was dissolved in CH$_2$Cl$_2$ (150 mL), to which was added BOC$_2$O (2.44 g) and TEA (1.7 g). When TLC (1:1 hexanes/EtOAc) showed no more material remaining on the baseline, saturated aqueous NH$_4$Cl (200 mL) was added, and, after separating the organic phase, the mixture was extracted with CH$_2$Cl$_2$ (3×200 mL). Combined extracts were dried over Na$_2$SO$_4$, filtered, and the filtrated concentrated to dryness to yield a yellow oil (7.7 g) which was chromatographed on a silica column using a gradient of hexanes/EtOAc (up to 1:1) to separate the diastereomers. By TLC using 1:1 PE/EtOAc, the R$_f$ for the anti isomer, compound 6, was 0.45. For the syn isomer (not shown in FIG. 1) the R$_f$ was 0.40. The yield of compound 6 was 2.45 g (39% overall based on Garner's aldehyde). $^1$H NMR of anti isomer (CDCl$_3$) δ 1.26 (br s, 20H), 1.32 (s, 9H), 1.45 (s, 9H), 1.56 (quintet, 2H, J=8 Hz), 2.06 (q, 2H, J=7 Hz), 2.52 (t, 2H, J=7 Hz), 2.55 (br s, 2H), 3.60 (br s, 1H), 3.72 (ddd, 1H, J=11.5 Hz, 7.0 Hz, 3.5 Hz), 3.94 (dt, 1H, J=11.5 Hz, 3.5 Hz), 4.32 (d, 1H, J=4.5 Hz), 5.28 (br s, 1H), 5.54 (dd, 1H, J=15.5 Hz, 6.5 Hz), 5.78 (dt, 1H, J=15.5 Hz, 6.5 Hz). $^{13}C\{^1H\}$ NMR (CDCl$_3$) δ 156.95, 134.80, 129.66, 80.47, 75.46, 63.33, 56.17, 42.44, 32.98, 31.70, 30.58, 30.32, 30.31, 30.28, 30.20, 30.16, 30.00, 29.89, 29.80, 29.28, 29.08, 29.03.

Anal. Calculated for C$_{27}$H$_{53}$NO$_4$S: C, 66.48; H, 10.95; N, 2.87. Found: C, 65.98; H, 10.46; N, 2.48.

Compound 7.

To a solution of the alcohol compound 6 (609.5 mg, 1.25 mmol) dissolved in dry pyridine (2 mL) was added CBr$_4$ (647.2 mg, 1.95 mmol, 1.56 equiv). The flask was cooled in an ice bath and P(OMe)$_3$ (284.7 mg, 2.29 mmol, 1.84 equiv) was added drop wise over 2 min. After 4 min. the ice bath was removed and after 12 hr. the mixture was diluted with ether (20 mL). The resulting mixture washed with aqueous HCl (10 mL, 2 N) to form an emulsion which separated on dilution with water (20 mL). The aqueous phase was extracted with ether (2×10 mL), then EtOAc (2×10 mL). The ether extracts and first EtOAc extract were combined and washed with aqueous HCl (10 mL, 2 N), water (10 mL), and saturated aqueous NaHCO$_3$ (10 mL). The last EtOAc extract was used to back-extract the aqueous washes. Combined organic phases were dried over MgSO$_4$, filtered, and the filtrate concentrated to leave crude product (1.16 g), which was purified by flash chromatography over silica (3×22 cm column) using CH$_2$Cl$_2$, then CH$_2$Cl$_2$-EtOAc (1:20, 1:6, 1:3, and 1:1—product started to elute, 6:4, 7:3). Early fractions contained 56.9 mg of oil. Later fractions provided product (compound 7, 476.6 mg, 64%) as clear, colorless oil.

Anal. Calculated for C$_{29}$H$_{58}$NO$_7$PS (595.82): C, 58.46; H, 9.81; N, 2.35. Found: C, 58.09; H, 9.69; N, 2.41.

Compound 8.

A flask containing compound 7 (333.0 mg, 0.559 mmol) and a stir bar was evacuated and filled with nitrogen. Acetonitrile (4 mL, distilled from CaH$_2$) was injected by syringe and the flask now containing a solution was cooled in an ice bath. Using a syringe, (CH$_3$)$_3$SiBr (438.7 mg, 2.87 mmol, 5.13 equiv.) was added over the course of 1 min. After 35 min., the upper part of the flask was rinsed with an additional portion of acetonitrile (1 mL) and the ice bath was removed. After another 80 min., an aliquot was removed, the solution dried by blowing nitrogen gas over it, and the residue analyzed by $^1$H NMR in CDCl$_3$, which showed only traces of peaks ascribed to P—OCH$_3$ moieties. After 20 min., water (0.2 mL) was added to the reaction mixture, followed by the CDCl$_3$ solution used to analyze the aliquot, and the mixture was concentrated to ca. 0.5 mL volume on a rotary evaporator. Using acetone (3 mL) in portions the residue was transferred to a tared test tube, forming a pale brown solution. Water (3 mL) was added in portions. After addition of 0.3 mL, cloudiness was seen. After a total of 1 mL, a gummy precipitate had formed. As an additional 0.6 mL of water was added, more cloudiness and gum separated, but the final portion of water seemed not to change the appearance of the mixture. Overall, this process was accomplished over a period of several hours. The tube was centrifuged and the supernatant removed by pipet. The solid, no longer gummy, was dried over P$_4$O$_{10}$ in vacuo, leaving compound 8 (258.2 mg, 95%) as a monohydrate.

Anal. Calculated. for C$_{22}$H$_{46}$NO$_5$PS+H$_2$O (485.66): C, 54.40; H, 9.96; N, 2.88. Found: C, 54.59; H, 9.84; N, 2.95.

Compound 9.

Compound 8 (202.6 mg, 0.417 mmol) was added in a glove box to a test tube containing a stir bar, dry THF (3 mL) and glacial HOAc (3 mL). NBSCl (90 mg, 0.475 mmol, 1.14 equiv) were added, and after 0.5 hr., a clear solution was obtained. After a total of 9 hr., an aliquot was evaporated to dryness and the residue analyzed by $^1$H NMR in CDCl$_3$. The peaks corresponding to CH$_2$StBu and CH$_2$SSAr suggested that reaction was about 75% complete, and comparison of the spectrum with that of pure NBSCl in CDCl₃ suggested that none of the reagent remained in the reaction. Therefore, an additional portion (24.7 mg, 0.130 mmol, 0.31 equiv) was added, followed 3 hr. later by an additional portion (19.5 mg, 0.103 mmol, 0.25 equiv). After another 1 hr., the mixture was transferred to a new test tube using THF (2 mL) to rinse and water (1 mL) was added.

Compound 10.

PMe₃ (82.4 mg, 1.08 mmol, 1.52 times the total amount of 2-nitrobenzenesulfenyl chloride added) was added to the clear solution compound 9 described above. The mixture grew warm and cloudy, with precipitate forming over time. After 4.5 hr., methanol was added, and the tube centrifuged. The precipitate settled with difficulty, occupying the bottom 1 cm of the tube. The clear yellow supernatant was removed using a pipet. Methanol (5 mL, deoxygenated with nitrogen) was added, the tube was centrifuged, and the supernatant removed by pipet. This cycle was repeated three times. When concentrated, the final methanol wash left only 4.4 mg of residue. The bulk solid residue was dried over $P_4O_{10}$ in vacuo, leaving compound 10 (118.2 mg, 68%) as a monohydrochloride.

Anal. Calculated for $C_{18}H_{38}NO_5S+HCl$ (417.03): C, 51.84; H, 9.43; N, 3.36. Found: C, 52.11; H, 9.12; N, 3.30.

Compound 11.

Compound 6 (1.45 g, 2.97 mmol) was dissolved in AcOH (20 mL), and NBSCl (0.56 g, 2.97 mmol) was added all at once. The reaction was allowed to stir for 3 hr. or until the disappearance of the starting material and appearance of the product was observed by TLC [product $R_f$=0.65, starting material $R_f$=0.45, 1:1 EtOAc/hexanes]. The reaction was concentrated to dryness on a high vacuum line and the residue dissolved in THF/H₂O (100 mL of 10:1).

Compound 12.

Ph₃P (0.2.33 g, 8.91 mmol) was added all at once to the solution above that contained compound 11 and the reaction was allowed to stir for 3 hr. or until the starting material disappeared. The crude reaction mixture was concentrated to dryness on a high vacuum line, leaving a residue that contained compound 12.

Compound 13.

The residue above containing compound 12 was dissolved in DCM (50 mL) and TFA (10 mL). The mixture was stirred at RT for 5 hr. and concentrated to dryness. The residue was the loaded onto a column with silica gel and chromatographed with pure DCM, followed by DCM containing 5% MeOH, then 10% MeOH, to yield the final product, compound 13, as a sticky white solid (0.45 g, 46% yield from 5). ¹H NMR (CDCl₃) δ 1.27 (s), 1.33 (br m,), 1.61 (p, 2H, J=7.5 Hz), 2.03 (br d, 2H, J=7 Hz), 2.53 (q, 2H, J=7.5 Hz), 3.34 (br s, 1H), 3.87 (br d, 2H, J=12 Hz), 4.48 (br s, 2H), 4.58 (br s, 2H), 5.42 (dd, 1H, J=15 Hz, 5.5 Hz), 5.82 (dt, 1H, J=15 Hz, 5.5 Hz), 7.91 (br s, 4H). ¹³C{¹H} NMR (CDCl₃) δ 136.85, 126.26, 57.08, 34.76, 32.95, 30.40, 30.36, 30.34, 30.25, 30.19, 30.05, 29.80, 29.62, 29.09, 25.34.

Example 2

Synthetic Schemes for Making Thiolated Fatty Acids

Figure 2A:
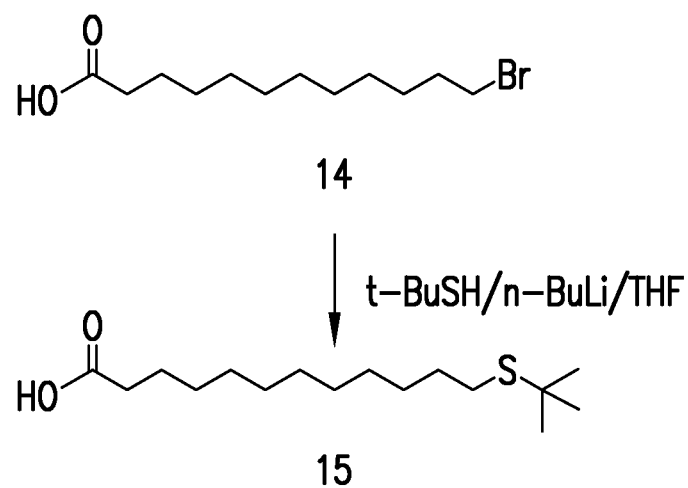
FIG. 2a is the initial portion of a synthesis scheme for a typical protected thiolated fatty acid and FIG. 2b is a continuation of the same showing the remainder of the scheme.
Figure 2B:
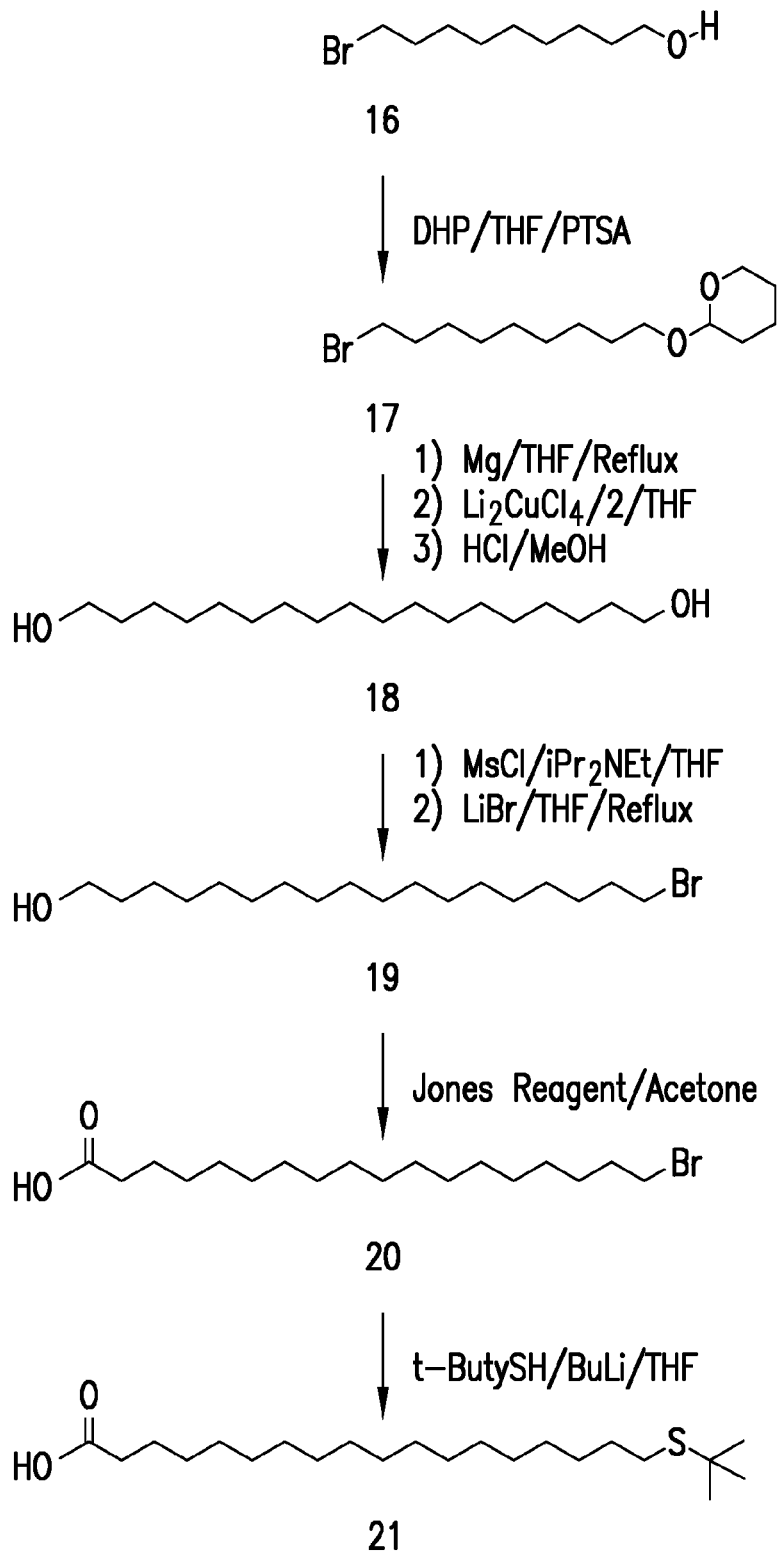

The synthetic approach described in this example details the preparation of a thiolated fatty acid to be incorporated into a more complex lipid structure that could be further complexed to a protein or other carrier and administered to an animal to elicit an immune response. The approach uses using conventional organic chemistry. A scheme showing the approach taken in this example is provided in FIG. 2, and the compound numbers in the synthetic description below refer to the numbered structures in FIG. 2.

Two syntheses are described. The first synthesis, for a C-12 thiolated fatty acid, starts with the commercially available 12-dodecanoic acid, compound 14. The bromine is then displaced with t-butyl thiol to yield the protected C-12 thiolated fatty acid, compound 15. The second synthesis, for a C-18 thiolated fatty acid, starts with the commercially available 9-bromo-nonanol (compound 16). The hydroxyl group in compound 16 is protected by addition of a dihydropyran group and the resulting compound, 17, is dimerized through activation of half of the brominated material via a Grignard reaction, followed by addition of the other half. The 18-hydroxy octadecanol (compound 18) produced following acid-catalyzed removal of the dihydropyran protecting group is selectively mono-brominated to form compound 19. During this reaction approximately half of the alcohol groups are activated for nucleophilic substitution by formation of a methane sulfonic acid ester. The alcohol is then oxidized to form the 18-bromocarboxylic acid, compound 20, which is then treated with t-butyl thiol to displace the bromine and form the protected, thiolated C-18 fatty acid, compound 21.

The protected thiolated fatty acids, each a t-butyl thioether, can be incorporated into a complex lipid and the protecting group removed using, e.g., one of the de-protecting approaches described in Examples 1 and 3. The resulting free thiol then can be used to complex with a protein or other carrier prior to inoculating animal with the hapten.

A. Synthesis of a C-12 Thiolated Fatty Acid

Compound 15.

t-Butyl thiol (12.93 g, 143 mmol) was added to a dry Schlenk flask, and Schlenk methods were used to put the system under nitrogen. Dry, degassed THF (250 mL) was added and the flask cooled in an ice bath. n-BuLi (55 mL of 2.5 M in hexanes, 137.5 mmol) was slowly added over 10 min by syringe. The mixture was allowed to stir at 0° C. for an hour. The bromoacid, compound 14 (10 g, 36 mmol), was added as a solid and the reaction heated and stirred at 60° C. for 24 hr. The reaction was quenched with 2 M HCl (250 mL), and extracted with ether (2×300 mL). The combined ethereal layers were dried with magnesium sulfate, filtered, and the filtrate concentrated by rotary evaporation to yield the thioether acid, compound 15 (10 g, 99% yield) as a beige powder. ¹H NMR (CDCl₃, 500 MHz) δ 1.25-1.35 (br s, 12H), 1.32 (s, 9H), 1.35-1.40 (m, 2H), 1.50-1.60 (m, 2H), 1.60-1.65 (m, 2H), 2.35 (t, 2H, J=7.5 Hz), 2.52 (t, 2H, J=7.5 Hz). Principal ion in HRMS (ES-TOF) was observed at m/z 311.2020, calculated for M+Na⁺ 311.2015.

B. Synthesis of a C-12 Thiolated Fatty Acid

Compound 17.

A dry Schlenk flask was charged with compound 16 (50 g, 224.2 mmol) and dissolved in dry degassed THF (250 mL) distilled from sodium/benzophenone. The flask was cooled in an ice bath and then PTSA (0.5 g, 2.6 mmol) was added. Dry, degassed DHP (36 g, 42.8 mmol) was then added slowly over 5 min. The mixture was allowed to warm up to RT and left to stir overnight and monitored by TLC (10:1 PE:EtOAc) until the reaction was deemed done by the complete disappearance of the spot for the bromoalcohol. TEA (1 g, 10 mmol) was then added to quench the PTSA. The mixture was then washed with cold sodium bicarbonate solution and extracted with EtOAc (3×250 mL). The organic layers were then dried with magnesium sulfate and concentrated to yield 68.2 g of crude product which was purified by column chromatography (10:1 PE:EtOAc) to yield 60 g (99% yield) of a colorless oil. ¹H NMR (CDCl₃, 500 MHz) δ 1.31 (br s, 6H), 1.41-1.44 (m, 2H), 1.51-1.62 (obscured multiplets, 6H), 1.69-1.74 (m, 1H), 1.855 (quintet, J=7.6 Hz, 2H), 3.41 (t, J=7 Hz, 2H), 3.48-3.52 (m, 2H), 3.73 (dt, 2H, J=6.5 Hz), 3.85-3.90 (m, 2H), 4.57 (t, 2H, J=3 Hz).

Compound 18.

Magnesium shavings (2.98 g, 125 mmol) were added to a flame-dried Schlenk flask along with a crystal of iodine. Dry THF (200 mL) distilled from sodium was then added and the system was degassed using Schlenk techniques. Compound 17 (30 g, 97 mmol) was then slowly added to the magnesium over 10 min. and the solution was placed in an oil bath at 65° C. and allowed to stir overnight. The reaction was deemed complete by TLC by quenching an aliquot with acetone and observing the change in RF in a 10:1 PE:EtOAc mixture. The Grignard solution was then transferred by cannula to a three-necked flask under nitrogen containing additional compound 17 (30 g, 97 mmol). The flask containing the resulting mixture was then cooled to 0° C. in an ice bath and a solution of $Li_2CuCl_4$ (3 mL of 1 M) was then added via syringe. The reaction mixture turned a very dark blue within a few minutes. This mixture was left to stir overnight. The next morning the reaction was deemed complete by TLC (10:1 PE:EtOAc), quenched with a saturated $NH_4Cl$ solution, and then extracted into ether (3×250 mL). The ether layers were dried with magnesium sulfate and concentrated to yield crude product (40 g), which was dissolved in MeOH. Concentrated HCl (0.5 mL) was then added, which resulted in the formation of a white emulsion, which was left to stir for 3 hr. The white emulsion was then filtered to yield 16 g (58% yield) of the pure diol, compound 18. $^1$H NMR ($CDCl_3$, 200 MHz) δ 1.26 (br s, 24H), 1.41-1.42 (m, 4H), 1.51-1.68 (m, 4H), 3.65 (t, 4H, J=6.5 Hz).

Compound 19.

The symmetrical diol, compound 18 (11 g, 38.5 mmol), was added to a dry Schlenk flask under nitrogen, then dry THF (700 mL) distilled from sodium was added. The system was degassed and the flask put in an ice bath. Diisopropylethylamine (6.82 mL, 42.3 mmol) was added via syringe, followed by MsCl (3.96 g, 34.4 mmol) added slowly, and the mixture was left to stir for 1 hr. The reaction was quenched with saturated $NaH_2PO_4$ solution (300 mL), and then extracted with EtOAc (3×300 mL). The organic layers were then combined, dried with $MgSO_4$, and concentrated to yield 14 g of a mixture of the diol, monomesylate, and dimesylate. NMR showed a 1:0.8 mixture of $CH_2OH:CH_2OMs$ protons. The mixture was then dissolved in dry THF (500 mL), deoxygenated, and to it was added LiBr (3.5 g, 40.23 mmol). This mixture was allowed reflux overnight, upon which the reaction was quenched with water (150 mL), and extracted with EtOAc (3×250 mL). The organic layer was then dried with $MgSO_4$, and concentrated to yield a mixture of brominated products that were then purified by flash chromatography (DCM) to yield compound 19 (3.1 g, 25% yield) as a white powder. $^1$H NMR ($CDCl_3$, 500 MHz) δ 1.26 (br s, 26H), 1.38-1.46 (m, 2H), 1.55 (quintet, 2H, J=7.5 Hz), 1.85 (quintet, 2H, J=7.5 Hz), 3.403 (t, 2H, J=6.8 Hz), 3.66 (t. 2H, J=6.8 Hz).

Compound 20.

A round bottom flask was charged with compound 19 (2.01 g, 5.73 mmol) and the solid dissolved in reagent grade acetone (150 mL). Simultaneously, Jones reagent was prepared by dissolving $CrO_3$ (2.25 g, 22 mmol) in $H_2SO_4$ (4 mL) and then slowly adding 10 mL of cold water and letting the solution stir for 10 min. The cold Jones reagent was then added to the round bottom flask slowly over 5 min., after which the solution stirred for 1 hr. The resulting orange solution turned green within several minutes. The mixture was then quenched with water (150 mL) extracted twice in ether (3×150 mL). The ether layers were then dried with magnesium sulfate, and concentrated to yield compound 20 (2.08 g, 98% yield) as a white powder. $^1$H NMR ($CDCl_3$, 200 MHz) δ 1.27 (br s, 26H), 1.58-1.71 (m, 2H), 1.77-1.97 (m, 2H), 2.36 (t, 2H, J=7.4 Hz), 3.42 (t, 2H, J=7 Hz).

Compound 21.

t-Butylthiol (11.32 g, 125 mmol) was added to a dry Schlenk flask and dissolved in dry THF (450 mL) distilled from sodium. The solution was deoxygenated by bubbling nitrogen through it before the flask was placed in an ice bath. n-BuLi solution in hexanes (70 mL of 1.6 M) was then added slowly via syringe over 10 min. This mixture was allowed to stir for 1 hr., then compound 20 (5.5 g, 16.2 mmol) was added and the solution was left to reflux at 60° C. overnight. The next morning an aliquot was worked up, analyzed by NMR, and the reaction deemed complete. The reaction was quenched with HCl (200 mL of 2 M) and extracted with ether (3×250 mL). The ethereal layers were then dried with magnesium sulfate, filtered, and the filtrate concentrated to yield the product, compound 21, as a white solid (5 g, 90% yield). $^1$H NMR ($CDCl_3$, 200 MHz) δ 1.26 (br s, 26H), 1.32 (br s, 9H), 1.48-1.70 (m, 4H), 2.35 (t, 2H, J=7.3 Hz), 2.52 (t, 2H, J=7.3 Hz). $^{13}$C NMR ($CDCl_3$, 200 MHz) δ 24.69, 28.35, 29.05, 29.21, 29.28, 29.39, 29.55, 29.89, 31.02 (3C), 33.98, 41.75, 179.60.

Example 3

Synthetic Scheme for Making a Thiolated Analog of LPA

Figure 3A:
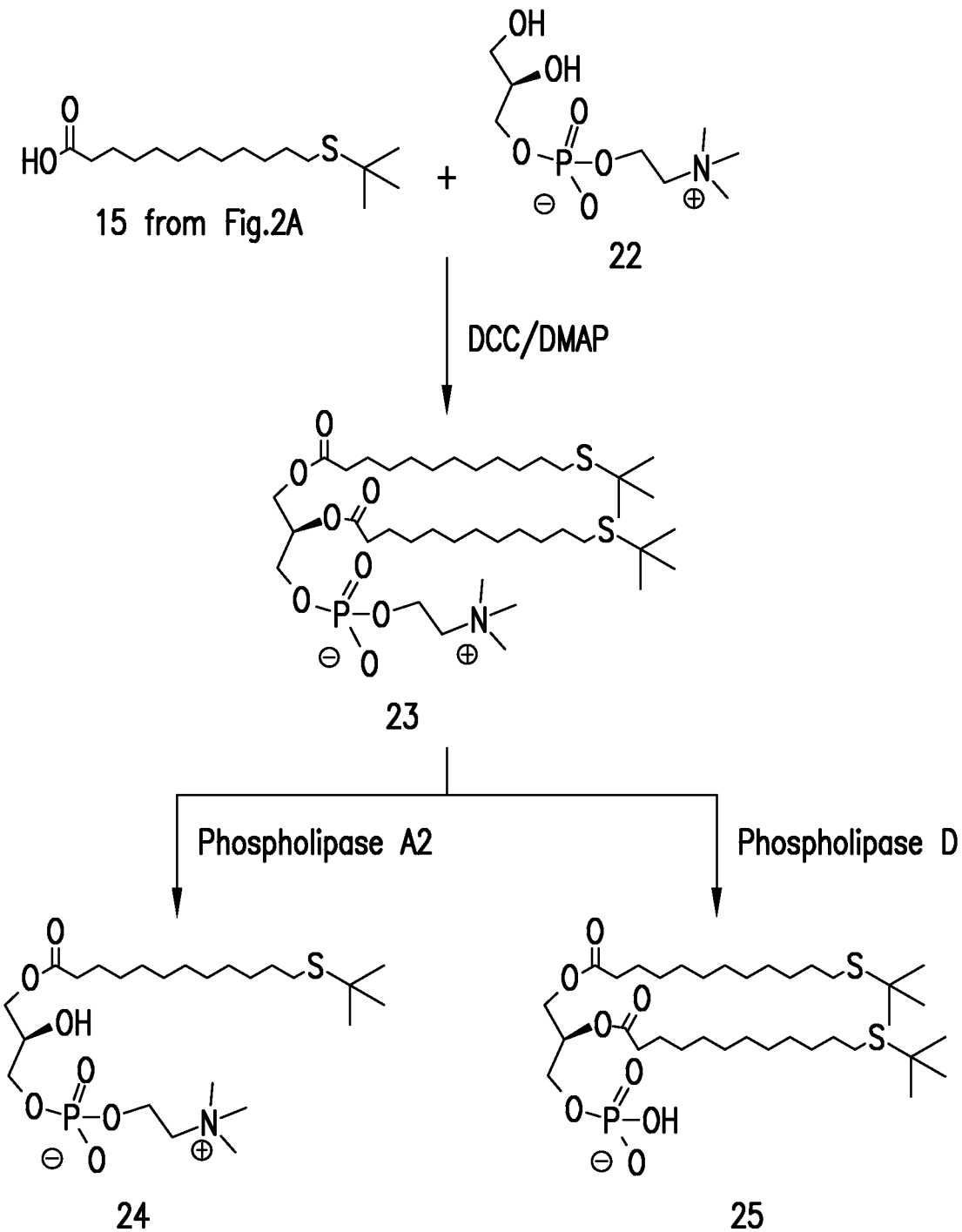
FIG. 3a is the initial portion of a synthesis scheme for a typical thiolated LPA hapten and FIG. 3b is a continuation of the same showing the remainder of the scheme.
Figure 3B:
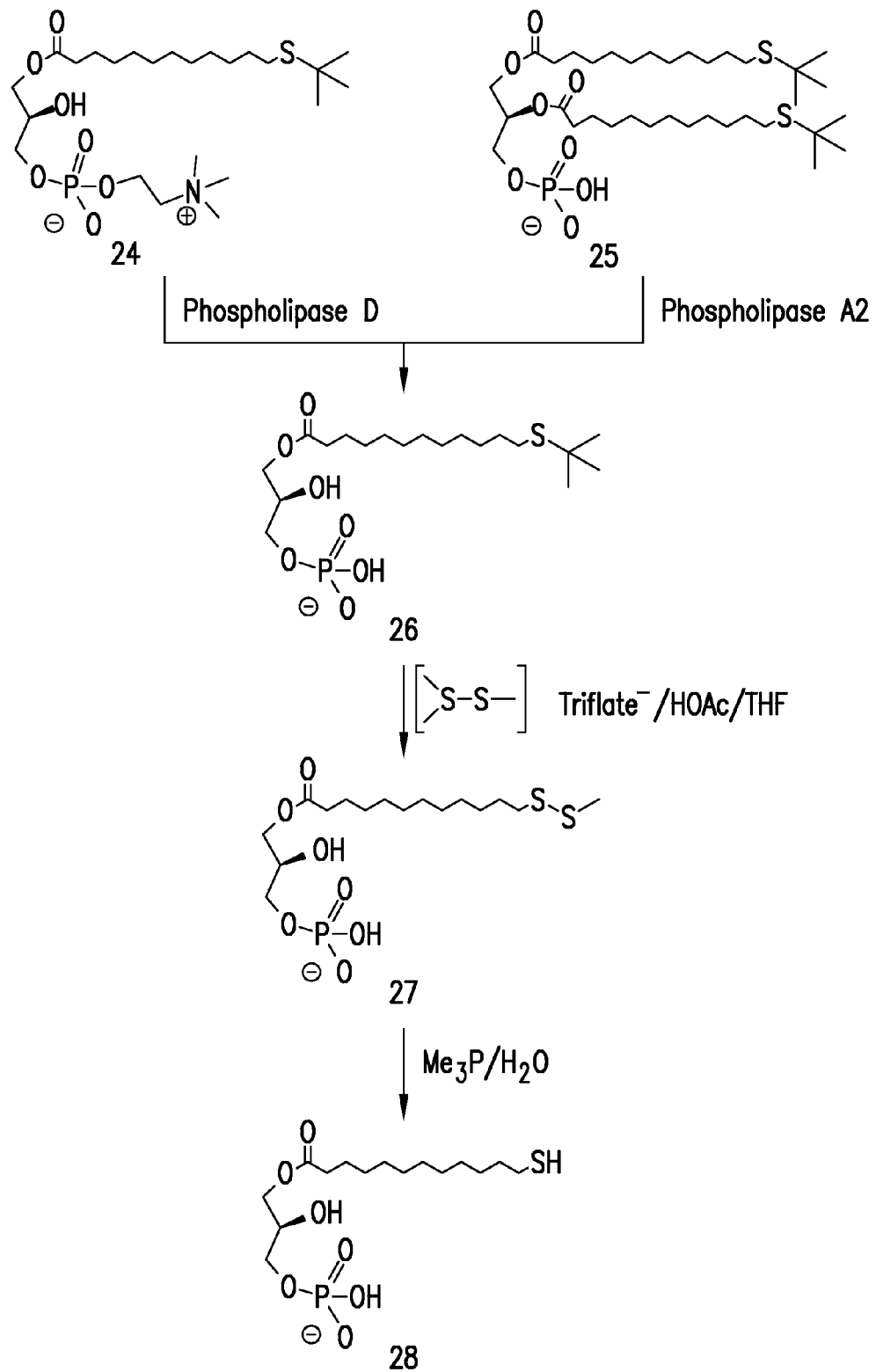

The synthetic approach described in this example results in the preparation of thiolated LPA. The LPA analog can then be further complexed to a carrier, for example, a protein carrier, which can then be administered to an animal to elicit an immugenic response to LPA. This approach uses both organic chemistry and enzymatic reactions, the synthetic scheme for which is provided in FIG. 3. The compound numbers in the synthetic description below refer to the numbered structures in FIG. 3.

The starting materials were compound 15 in Example 2 and enantiomerically pure glycerophoshocholine (compound 22). These two chemicals combined to yield the di-acetylated product, compound 23, using DCC to facilitate the esterification. In one synthetic process variant, the resulting di-acylated glycerophosphocholine was treated first with phospholipase-A2 to remove the fatty acid at the sn-2 position of the glycerol backbone to produce compound 24. This substance was further treated with another enzyme, phospholipase-D, to remove the choline and form compound 26. In another synthetic process variant, the phospholipase-D treatment preceded the phospholipase-A2 treatment to yield compound 25, and treatment of compound 25 with phospholipase-D then yields compound 26. Both variants lead to the same product, the phosphatidic acid derivative, compound 26. The t-butyl protecting group in compound 26 is then removed, first using trimethyl disulfide triflate to produce compound 27, followed by a disulfide reduction to produce the desired LPA derivative, compound 28. As those in the art will appreciate, the nitrobenzyl sulfenyl reaction sequence described in Example 1 can also be used to produce compound 28.

Compound 23.

To a flame-dried Schlenk flask were added the thioether acid, compound 15 (10 g, 35.8 mmol), compound 22 (glycerophosphocholine-$CdCl_2$ complex, 4.25 g, 8.9 mmol), DCC (7.32 g, 35.8 mmol), and DMAP (2.18 g, 17.8 mmol), after which the flask was evacuated and filled with nitrogen. A minimal amount of dry, degassed DCM was added (100 mL), resulting in a cloudy mixture. The flask was covered with foil and then left to stir until completed, as by TLC (silica, 10:5:1 DCM:MeOH:concentrated $NH_4OH$). The insolubility of compound 16 precluded monitoring its disappearance by TLC, but the reaction was stopped when the product spot of $R_f$ 0.1 was judged not to be increasing in intensity. This typically required 3 to 4 days, and in some cases, addition of more DCC and DMAP. Upon completion, the reaction mixture was filtered, and the filtrate concentrated to yield a yellow oil, which was purified using flash chromatography using the solvent system described above to yield 3.6 g (50% yield) of a clear wax containing a mixture of compound 23 and monoacylated products in a ratio of 5 to 1, as estimated from comparing the integrals for the peaks for the $(CH3)_3N-$, $-CH_2StBu$ and $-CH_2COO-$ moieties. Analysis of the oil by HRMS (ESI-TOF) produced a prominent ion at m/z 820.4972, calculated for $M+Na^+=C_{40}H_{80}NNaO_8PS_2^+$ 820.4960.

A. Synthesis Variant 1

Phospholipase-A2 Treatment

Compound 24.

A mixture of compound 23 and monoacetylated products as described above (3.1 g, 3.9 mmol) was dissolved in $Et_2O$ (400 mL) and methanol (30 mL). Borate buffer (100 mL, pH 7.4 0.1M, 0.072 mM in $CaCl_2$) was added, followed by phospholipase-A2 (from bee venom, 130 units, Sigma). The resulting mixture was left to stir for 10 hr., at which point TLC (silica, MeOH:water 4:1—the previous solvent system 10:5:1 DCM:MeOH:concentrated $NH_4OH$ proved ineffective) showed the absence of the starting material ($R_f$=0.7) and the appearance of a new spot ($R_f$=0.2). The organic and aqueous layers were separated and the aqueous layer was washed with ether (2×250 mL). The product was extracted from the aqueous layer with a mixture of DCM:MeOH (2:1, 2×50 mL). The organic layers were then concentrated by rotary evaporation to yield product as a white wax (1.9 g, 86% yield) that NMR showed to be a pure product (compound 24).

$^1$H NMR ($CDCl_3$, 500 MHz) δ 1.25-1.27 (br s, 12H), 1.31 (s, 9H), 1.35-1.45 (m, 2H), 1.52-1.60 (m, 4H), 2.31 (t, 2H, J=7.5 Hz), 2.51 (t, 2H, J=7.5 Hz), 3.28 (br s, 9H) 3.25-3.33 (br s, 2H), 3.78-3.86 (m, 1H), 3.88-3.96 (m, 2H), 4.04-4.10 (m, 2H), 4.26-4.34 (m, 2H). Analysis of the wax by HRMS (ESI-TOF) produced a prominent ion at m/z 550.2936, calculated for $M+Na^+$ 550.2943 ($C_{24}H_{50}NNaO_7PS_2^+$), and an m/z at 528.3115, calculated for $MH^+$ 528.3124 ($C_{24}H_{51}NO_7PS_2^+$).

Anal. Calculated. for $C_{24}H_{50}NO_7PS+2H_2O$ (563.73): C, 51.13; H, 9.66; N, 2.48. Found: C, 50.90; H, 9.37; N, 2.76.

Compound 26.

The lyso compound 24 (1.5 g, 2.7 mmol) was dissolved in a mixture of sec-butanol (5 mL) and $Et_2O$ (200 mL), and the resulting cloudy mixture was sonicated until the cloudiness dissipated. Buffer (200 mL, pH 5.8, 0.2 M NaOAc, 0.08 M $CaCl_2$) was added, followed by cabbage extract (80 mL of extract from savoy cabbage (which contains phospholipase-D), containing 9 mg of protein/mL). The reaction was stirred for 1 day and monitored by TLC ($C_{18}$RP $SiO_2$, 5:1 ACN: water), $R_f$ of starting material and product=0.3 and 0.05, respectively. In order to push the reaction to completion, as needed an additional portion of cabbage extract (50 mL) was added and the reaction stirred a further day. This process was repeated twice more, as needed to complete the conversion. When the reaction was complete, the mixture was concentrated on the rotary evaporator to remove the ether, and then EDTA solution (0.5 M, 25 mL) was added and the product extracted into a 5:4 mixture of MeOH:DCM (300 mL). Concentration of the organic layer followed by recrystallization of the residue from DCM and acetone afforded pure product (0.9 g, 75% yield). $^1$H NMR ($CDCl_3$, 200 MHz) δ 1.25-1.27 (br s, 12H), 1.33 (s, 9H), 1.52-1.60 (m, 4H), 2.34 (t, 2H, J=7.5 Hz), 2.52 (t, 2H, J=7.5 Hz), 3.6-3.8 (br s, 1H), 3.85-3.97 (br s, 2H), 4.02-4.18 (m, 2H).

Compound 27.

The protected sample LPA, compound 26 (, 0.150 g, 0.34 mmol), was methanol washed and added to a vial in the glove box. This was then suspended in a mixture of AcOH:THF (1:1, 10 mL), which never fully dissolved even after 1 hr. of sonication. Solid $[Me_2SSMe]OTf$ (0.114 g, 0.44 mmol) was then added. This was left to stir for 18 hr. The reaction was monitored by removing an aliquot, concentrating it to dryness under vacuum, and re-dissolving or suspending the residue in $CD_3OD$ for observing the $^1$H NMR shift of the $CH_2$ peak closest to the sulfur. The starting material had a peak at 2.52 ppm, whereas the unsymmetrical disulfide formed at this juncture had a peak at around 2.7 ppm. This material (compound 27) was not further isolated or characterized.

Compound 28.

The mixture containing compound 27 was treated with water (100 µL) immediately followed by $PMe_3$ (0.11 g, 1.4 mmol). After stirring for 3 hr. the solvent was removed by vacuum to yield an insoluble white solid. Methanol (5 mL) was added, the mixture centrifuged, and the mother liquor decanted. Vacuum concentration yielded 120 mg (91% yield) of compound 28, a beige solid. Compound 28 is a thiolated LPA hapten that can be conjugated to a carrier, for example, albumin or KLH, via disulfide bond formation. Characterization of compound 28: $^1$H NMR (1:1 $CD_3OD:CD_3CO_2D$, 500 MHz) δ 1.25-1.35 (br s, 12H), 1.32-1.4 (m, 2H), 1.55-1.6 (m, 4H), 2.34 (t, 2H, J=7), 2.47 (t, 2H, J=8.5), 3.89-3.97 (br s, 2H), 3.98-4.15 (m, 2H), 4.21 (m, 1H). Negative ion ES of the sample dissolved in methanol produced a predominant ion at m/z=385.1.

Example 4

Antibodies to S1P

One type of therapeutic antibody specifically binds undesirable sphingolipids to achieve beneficial effects such as, e.g., (1) lowering the effective concentration of undesirable, toxic sphingolipids (and/or the concentration of their metabolic precursors) that would promote an undesirable effect such as a cardiotoxic, tumorigenic, or angiogenic effect; (2) to inhibit the binding of an undesirable, toxic, tumorigenic, or angiogenic sphingolipids to a cellular receptor therefore, and/or to lower the concentration of a sphingolipid that is available for binding to such a receptor. Examples of such therapeutic effects include, but are not limited to, the use of anti-S1P antibodies to lower the in vivo serum concentration of available S1P, thereby blocking or at least limiting S1P's tumorigenic and angiogenic effects and its role in post-MI heart failure, cancer, or fibrongenic diseases.

Thiolated S1P (compound 10 of FIG. 1) was synthesized to contain a reactive group (i.e., a sulfhydryl group) capable of cross-linking the essential structural features of S1P to a carrier moiety such as KLH. Prior to immunization, the thio-S1P analog was conjugated via IOA or SMCC cross-linking to protein carriers (e.g., KLH) using standard protocols. SMCC is a heterobifunctional crosslinker that reacts with primary amines and sulfhydryl groups, and represents a preferred crosslinker.

Swiss Webster or BALB-C mice were immunized four times over a two month period with 50 µg of immunogen (SMCC facilitated conjugate of thiolated-S1P and KLH) per injection. Serum samples were collected two weeks after the second, third, and fourth immunizations and screened by direct ELISA for the presence of anti-S1P antibodies. Spleens from animals that displayed high titers of the antibody were subsequently used to generate hybridomas per standard fusion procedures. The resulting hybridomas were grown to confluency, after which the cell supernatant was collected for ELISA analysis. Of the 55 mice that were immunized, 8 were good responders, showing significant serum titers of antibodies reactive to S1P. Fusions were subsequently carried out using the spleens of these mice and myeloma cells according to established procedures. The resulting 1,500 hybridomas were then screened by direct ELISA, yielding 287 positive hybridomas. Of these 287 hybridomas screened by direct ELISA, 159 showed significant titers. Each of the 159 hybridomas was then expanded into 24-well plates. The cell-conditioned media of the expanded hybridomas were then re-screened to identify stable hybridomas capable of secreting antibodies of interest. Competitive ELISAs were performed on the 60 highest titer stable hybridomas.

Of the 55 mice and almost 1,500 hybridomas screened, one hybridoma was discovered that displayed performance characteristics that justified limited dilution cloning, as is required to ultimately generate a true monoclonal antibody. This process yielded 47 clones, the majority of which were deemed positive for producing S1P antibodies. Of these 47 clones, 6 were expanded into 24-well plates and subsequently screened by competitive ELISA. From the 4 clones that remained positive, one was chosen to initiate large-scale production of the S1P monoclonal antibody. SCID mice were injected with these cells and the resulting ascites was protein A-purified (50% yield) and analyzed for endotoxin levels (<3 EU/mg). For one round of ascites production, 50 mice were injected, producing a total of 125 mL of ascites. The antibodies were isotyped as IgG1 kappa, and were deemed >95% pure by HPLC. The antibody was prepared in 20 mM sodium phosphate with 150 mM sodium chloride (pH 7.2) and stored at −70° C.

The positive hybridoma clone (designated as clone 306D326.26) was deposited with the ATCC (safety deposit storage number SD-5362), and represents the first murine mAb directed against S1P. The clone also contains the variable regions of the antibody heavy and light chains that could be used for the generation of a "humanized" antibody variant, as well as the sequence information needed to construct a chimeric antibody.

Screening of serum and cell supernatant for S1P-specific antibodies was by direct ELISA using the thiolated S1P analog described in Example 1 (i.e., compound 10) as the antigen. A standard ELISA was performed, as described below, except that 50 ul of sample (serum or cell supernatant) was diluted with an equal volume of PBS/0.1% Tween-20 (PBST) during the primary incubation. ELISAs were performed in 96-well high binding ELISA plates (Costar) coated with 0.1 µg of chemically-synthesized compound 10 conjugated to BSA in binding buffer (33.6 mM $Na_2CO_3$, 100 mM $NaHCO_3$; pH 9.5). The thiolated-S1P-BSA was incubated at 37° C. for 1 hr. at 4° C. overnight in the ELISA plate wells. The plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 uL of 0.1 ug/mL anti-S1P mAb diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL-X-800 ELISA plate reader (Bio-Tech).

For cross reactivity, a competitive ELISA was performed as described above, except for the following alterations (FIG. 4). The primary incubation consisted of the competitor (S1P, SPH, LPA, etc.) and a biotin-conjugated anti-S1P mAb. Biotinylation of the purified monoclonal antibody was performed using the EZ-Link Sulfo-NHS-Biotinylation kit (Pierce). Biotin incorporation was determined as per kit protocol and ranged from 7 to 11 biotin molecules per antibody. The competitor was prepared as follows: lipid stocks were sonicated and dried under argon before reconstitution in DPBS/BSA [1 mg/ml fatty acid-free BSA (Calbiochem) in DPBS (Invitrogen 14040-133)]. Purified anti-S1P mAb was diluted as necessary in PBS/0.5% Triton X-100. Competitor and antibody solutions were mixed together so to generate 3 parts competitor to 1 part antibody. A HRP-conjugated streptavidin secondary antibody (Jackson Immunoresearch) was used to generate signal.

Figure 4A:
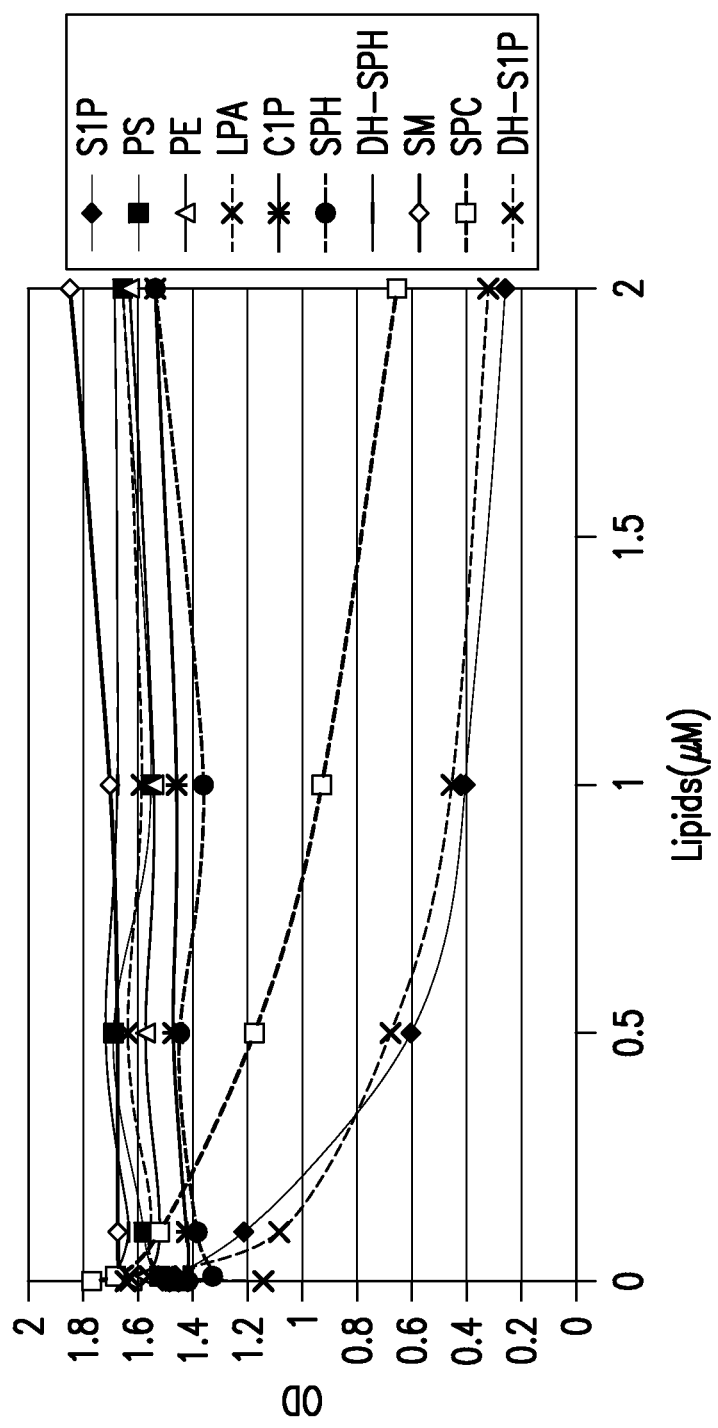
FIG. 4. The anti-S1P mAb is specific and sensitive for S1P and does not recognize structurally similar bioactive lipids. Panel A. Competitive ELISA with S1P, SPH, LPA, SPC and other structurally similar biolipids competing for the mAb binding to S1P on the plate. Only free S1P or DH-S1P can compete for binding, demonstrating the specificity of the anti-S1P mAb. SPC only slightly competes for binding. Panel B. Structures of bioactive lipids used in the evaluation of specificity.
Figure 4B:
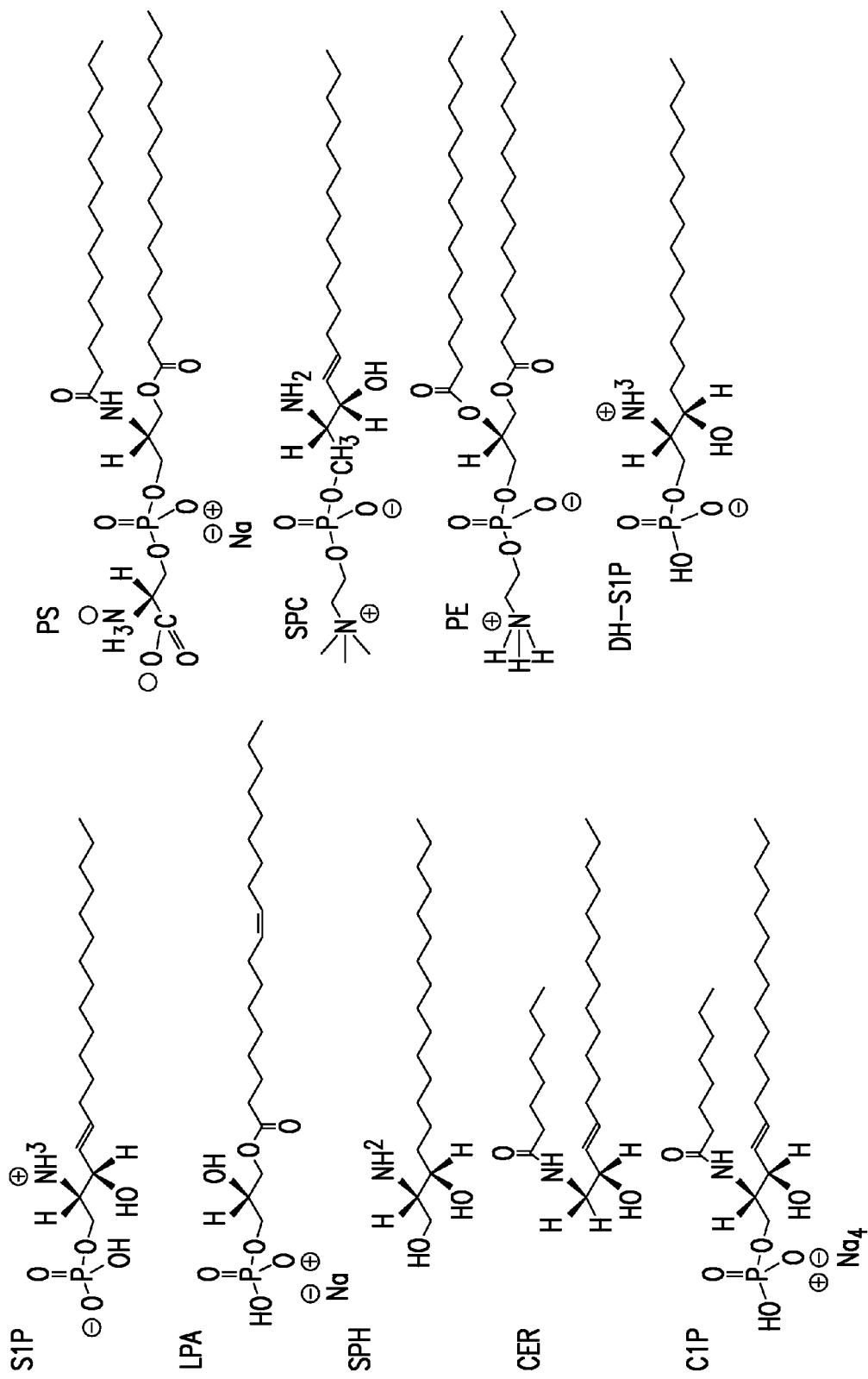

Another aspect of the competitive ELISA data shown in FIG. 4 is that it shows that the anti-S1P mAb was unable to distinguish the thiolated-S1P analog (compound 10) from the natural S1P that was added in the competition experiment. It also demonstrates that the antibody does not recognize any oxidation products because the analog was constructed without any double bonds (as is also true for the LPA analog described in Example 3). The anti-S1P mAb was also tested against natural product containing the double bond that was allowed to sit at room temperature for 48 hours. Reverse phase HPLC of the natural S1P was performed according to methods reported previously (Deutschman, et al. (July 2003), Am Heart J., vol. 146(1):62-8), and the results showed no difference in retention time. Further, a comparison of the binding characteristics of the monoclonal antibody to the various lipids shown in FIG. 4 indicates that the epitope recognized by the antibody do not involve the hydrocarbon chain in the region of the double bond of natural S1P. On the other hand, the epitope recognized by the monoclonal antibody is the region containing the amino alcohol on the sphingosine base backbone plus the free phosphate. If the free phosphate is linked with a choline (as is the case with SPC), then the binding was somewhat reduced. If the amino group is esterified to a fatty acid (as is the case with C1P), no antibody binding was observed. If the sphingosine amino alcohol backbone was replaced by a glycerol backbone (as is the case with LPA), there the S1P-specific monoclonal exhibited no binding. These epitope mapping data indicate that there is only one epitope on S1P recognized by the monoclonal antibody, and that this epitope is defined by the unique polar headgroup of S1P.

In a similar experiment using ELISA measurements, suitable control materials were evaluated to ensure that this anti-S1P monoclonal antibody did not recognize either the protein carrier or the crosslinking agent. For example, the normal crosslinker SMCC was exchanged for IOA in conjugating the thiolated-S1P to BSA as the laydown material in the ELISA. When IOA was used, the antibody's binding characteristics were nearly identical to when BSA-SMCC-thiolated-S1P was used. Similarly, KLH was exchanged for BSA as the protein that was complexed with thiolated-S1P as the laydown material. In this experiment, there was also no significant difference in the binding characteristics of the antibody.

Figure 5:
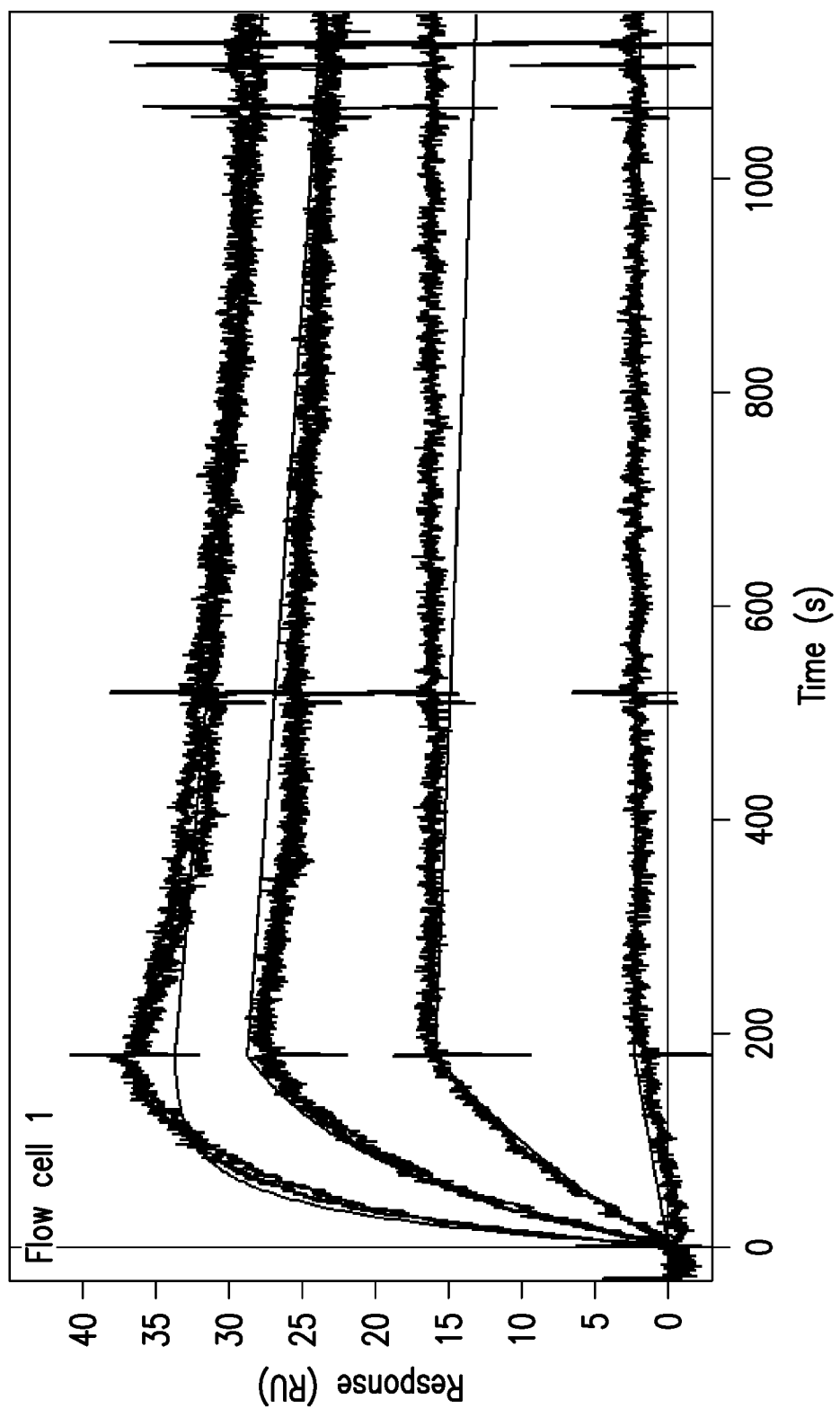
FIG. 5. BiaCore analysis of binding kinetics of anti-S1P mAb to thio-S1P tethered to a Biacore maleimide surface CM5 sensor chip. Various dilutions of anti-S1P mAb were applied to the flow cell for generating sensograms.

Binding Kinetics:

The binding kinetics of S1P to its receptor or other moieties has, traditionally, been problematic because of the nature of lipids. Many problems have been associated with the insolubility of lipids. For BIAcore measurements, these problems were overcome by directly immobilizing S1P to a BIAcore chip. Antibody was then flowed over the surface of the chip and alterations in optical density were measured to determine the binding characteristics of the antibody to S1P. To circumvent the bivalent binding nature of antibodies, S1P was coated on the chip at low densities. Additionally, the chip was coated with various densities of S1P (7, 20, and 1000 RU) and antibody binding data was globally fit to a 1:1 interaction model. FIG. 5 demonstrates the changes in optical density due to the binding of the monoclonal antibody to S1P at three different densities of S1P. Overall, the affinity of the monoclonal antibody to S1P was determined to be very high, in the range of approximately 88 picomolar (pM) to 99 nM, depending on whether a monovalent or bivalent binding model was used to analyze the binding data.

Example 5

Cloning and Characterization of the Variable Domains of an S1P Monoclonal Antibody A. Introduction.

The manufacture of biological products is complex, in part because of the complexity associated with the variability of the protein itself. For monoclonal antibodies (mAbs), variability can be localized to the protein backbone or to the carbohydrate moieties appended to these glycosylated proteins. For example, heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. On the other hand, carbohydrate heterogeneity introduced during cell culture includes differential addition of fucose, alternative mannose branching linkages, and differential presence of terminal sialylation. In addition, mutagenesis can be performed to alter glycosylation patterns. Oxidation is also a source of concern. For instance, the recombinant humanized monoclonal antibody HER2 undergoes oxidation in liquid formulations when exposed to intense light and elevated temperatures. Interestingly, such oxidation was reported to be formulation dependent (Lam, et al. (1997), Pharm. Sci., vol. 86: 1250-1255), and the presence of NaCl in the formulation reportedly caused an increase in oxidation at higher temperatures after contact with stainless steel containers or stainless steel components in the filling process. The methionine residue at position 255 in the heavy chain of the Fc region was determined to be the primary site of oxidation. The oxidation was eliminated by supplementing the media with methionine and thiosulfate caused by free radicals generated by the presence of metal ions and peroxide impurities in the formulation. For reasons such as these, process engineering is commonly applied to antibody molecules to improve their properties, such as enhanced expression in heterologous systems, resistance to proteases, reduced aggregation, and enhanced stability.

This example reports the cloning of the murine mAb against S1P. This antibody, termed Sphingomab™, is an IgG1 monoclonal antibody. The overall strategy consisted of cloning the murine variable domains of both the light chain (VL) and the heavy chain (VH). The consensus sequence of 306D VH shows that the constant region fragment is consistent with a gamma 2b isotype. The murine variable domains were cloned together with the constant domain of the light chain (CL) and with the constant domain of the heavy chain (CH1, CH2, and CH3), resulting in a chimeric antibody construct. Also, Sphingomab™ is unique because of the presence of a free cysteine residue in the Fab region at position 50 on the heavy chain in the CDR2 region. Replacing this residue could greatly facilitate formulation and manufacturing processes, as well as improving yields. Indeed, in an effort to improve the biophysical properties of the antibody molecule, substitution of the cysteine residue at position 50 with a panel of amino acid residues was performed by creating a series of constructs containing the desired substitution. These constructs were then expressed in mammalian cells, and the different antibody variants were compared in an ELISA assay for binding to S1P. Compared with the chimeric antibody, the resulting mutants carrying the substitution Cys50Ser and Cys50Arg exhibited a slight decrease in binding to S1P whereas the replacement of Cys with Phe or Ala did not alter the binding to S1P.

B. Materials and Methods.

1. Antibody Gene Cloning

A clone from the anti-S1P hybridoma cell line 306D326.1 (ATCC #SD-5362) was grown in DMEM (Dulbecco's Dulbecco's Modified Eagle Medium with GlutaMAX™ I, 4500 mg/L D-Glucose, Sodium Puruvate; Gibco/Invitrogen, Carlsbad, Calif., 111-035-003), 10% FBS (Sterile Fetal Clone I, Perbio Science), and 1× glutamine/Penicillin/Streptomycin (Gibco/Invitrogen). Total RNA was isolated from $10^7$ hybridoma cells using a procedure based on the RNeasy Mini kit (Qiagen, Hilden Germany). The RNA was used to generate first strand cDNA following the manufacturer's protocol ($1^{st}$ strand synthesis kit, Amersham Biosciences).

The immunoglobulin heavy chain variable region (VH) cDNA was amplified by PCR using an MHV7 primer (MHV7: 5'-ATGGRATGGAGCKGGRTCTTTMTCTT-3' [SEQ ID NO: 1]) in combination with a IgG2b constant region primer MHCG1/2a/2b/3 mixture (MHCG1: 5'-CAGTGGATAGACAGATGGGGG-3' [SEQ ID NO: 2]; MHCG2a: 5'-CAGTGGATAGACCGATGGGGC-3 [SEQ ID NO: 3]; MHCG2b: 5'-CAGTGGATAGACTGATGGGGG-3' [SEQ ID NO: 4]; MHCG3: 5'-CAAGGGATAGACA-GATGGGGC-3' [SEQ ID NO: 5]). The product of the reaction was ligated into the pCR2.1®-TOPO® vector (Invitrogen) using the TOPO-TA Cloning® kit and sequence. The variable domain of the heavy chain was then amplified by PCR from this vector and inserted as a Hind III and Apa I fragment and ligated into the expression vector pG1D200 (see U.S. Pat. No. 7,060,808) or pG4D200 (id.) containing the HCMVi promoter, a leader sequence, and the gamma-1 constant region to generate the plasmid pG1D200306DVH. The consensus sequence of 306D $V_H$ (FIG. 6; SEQ ID NO: 6) showed that the constant region fragment was consistent with a gamma 2b isotype.

Similarly, the immunoglobulin kappa chain variable region (VK) was amplified using the MKV 20 primer (5'-GTCTCT-GATTCTAGGGCA-3' [SEQ ID NO: 7]) in combination with the kappa constant region primer MKC (5'-ACTGGATG-GTGGGAAGATGG-3' [SEQ ID NO: 8]). The product of this reaction was ligated into the pCR2.1®-TOPO® vector using the TOPO-TA Cloning® kit and sequence. The variable domain of the light chain was then amplified by PCR and then inserted as a Bam HI and Hind III fragment into the expression vector pKN100 (see U.S. Pat. No. 7,060,808) containing the HCMV promoter, a leader sequence, and the human kappa constant domain, generating plasmid pKN100306DVK.

The heavy and light chain plasmids pG1D200306DVH plus pKN100306DVK were transformed into DH4a bacteria and stocked in glycerol. Large-scale plasmid DNA was prepared as described by the manufacturer (Qiagen, endotoxin-free MAXIPREP™ kit). DNA samples, purified using Qiagen's QIAprep Spin Miniprep Kit or EndoFree Plasmid Mega/Maxi Kit, were sequenced using an ABI 3730xl automated sequencer, which also translates the fluorescent signals into their corresponding nucleobase sequence. Primers were designed at the 5' and 3' ends so that the sequence obtained would overlap. The length of the primers was 18-24 bases, and preferably they contained 50% GC content and no predicted dimers or secondary structure. The amino acid sequences for the mouse $V_H$ and $V_L$ domains from Sphingomab™ are shown in FIG. 6 (SEQ ID NOS: 6 and 9, respectively). In FIG. 6, the CDR residues (see Kabat, E A (1982), Pharmavol Rev, vol. 34: 23-38) are boxed, and are shown below in Table 1.

TABLE 1

Mouse Sphingomab ™ CDR sequences of the mouse $V_H$ and $V_L$ domains

|  | CDR |
| --- | --- |
| VL CDR |  |
| ITTTDIDDDMN (SEQ ID NO: 10) | CDR1 |
| EGNILRP (SEQ ID NO: 11) | CDR2 |
| LQSDNLPFT (SEQ ID NO: 12) | CDR3 |
| VH CDR |  |
| DHTIH (SEQ ID NO: 13) | CDR1 |
| CISPRHDITKYNEMFRG (SEQ ID NO: 14) | CDR2 |
| GGFYGSTIWFDF (SEQ ID NO: 15) | CDR3 |

The complete nucleotide and amino acid sequences of several chimeric antibody $V_H$ and $V_L$ domains are shown in FIG. 7. In FIG. 7, the amino acid sequences are numbered, and the CDRs identified, according to the Kabat method (Kabat, et al. (1991), NIH National Technical Information Service, pp. 1-3242).

2. COS 7 Expression

For antibody expression in a non-human mammalian system, plasmids were transfected into the African green monkey kidney fibroblast cell line COS 7 by electroporation (0.7 ml at $10^7$ cells/ml) using 10 ug of each plasmid. Transfected cells were plated in 8 ml of growth medium for 4 days. The chimeric 306DH1×306DVK-2 antibody was expressed at 1.5 µg/ml in transiently co-transfected COS cell conditioned medium. The binding of this antibody to S1P was measured using the S1P ELISA.

Figure 8:
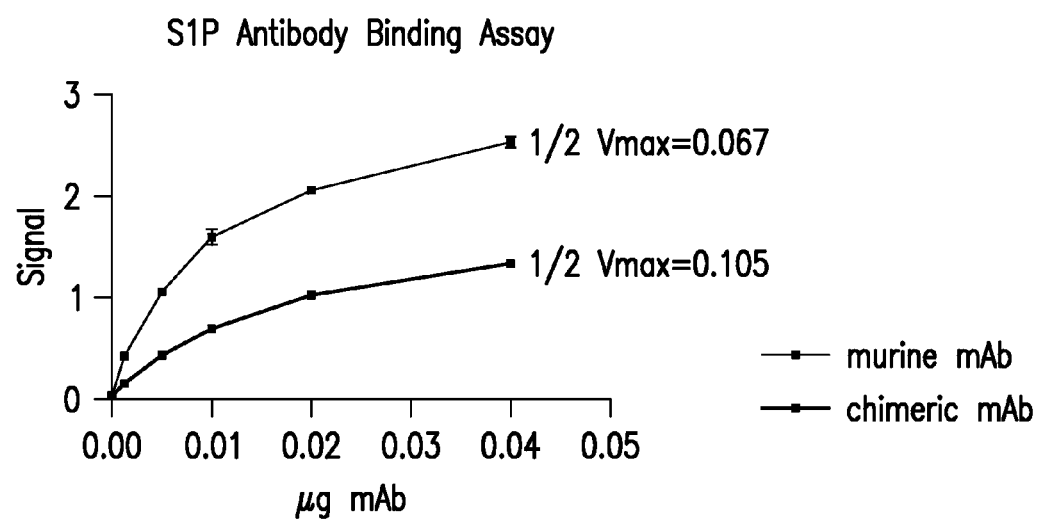
FIG. 8. Graph showing ELISA results for binding studies of murine Sphingomab™ and chimeric, SIP-binding antibodies derived from murine Sphingomab™.

The expression level of the chimeric antibody was determined in a quantitative ELISA as follows. Microtiter plates (Nunc MaxiSorp immunoplate, Invitrogen) were coated with 100 µl aliquots of 0.4 µg/ml goat anti-human IgG antibody (Sigma, St. Louis, Mo.) diluted in PBS and incubate overnight at 4° C. The plates were then washed three times with 200 µl/well of washing buffer (1×PBS, 0.1% TWEEN). Aliquots of 200 µL of each diluted serum sample or fusion supernatant were transferred to the toxin-coated plates and incubated for 37° C. for 1 hr. Following 6 washes with washing buffer, the goat anti-human kappa light chain peroxidase conjugate (Jackson Immuno Research) was added to each well at a 1:5000 dilution. The reaction was carried out for 1 hr at room temperature, plates were washed 6 times with the washing buffer, and 150 µL of the K-BLUE substrate (Sigma) was added to each well, incubated in the dark at room temperature for 10 min. The reaction was stopped by adding 50 µl of RED STOP solution (SkyBio Ltd.) and the absorption was determined at 655 nm using a Microplater Reader 3550 (Bio-Rad Laboratories Ltd.). Results from the antibody binding assays are shown in FIG. 8.

3. 293F Expression

For antibody expression in a human system, plasmids were transfected into the human embryonic kidney cell line 293F (Invitrogen) using 293fectin (Invitrogen) and using 293F-FreeStyle Media (Invitrogen) for culture. Light and heavy chain plasmids were both transfected at 0.5 g/mL. Transfections were performed at a cell density of $10^6$ cells/mL. Supernatants were collected by centrifugation at 1100 rpm for 5 minutes at 25° C. 3 days after transfection. Expression levels were quantified by quantitative ELISA (see below) and varied from 0.25-0.5 g/mL for the chimeric antibody.

4. Quantitative ELISA

Microtiter ELISA plates (Costar) were coated with rabbit anti-mouse IgG, F(ab')$_2$ fragment specific (Jackson Immuno Research) or rabbit anti-human, IgG F(ab')$_2$ fragment specific (Jackson Immuno Research) diluted in 1 M Carbonate Buffer (pH 9.5) at 37° C. for 1 hr. Plates were washed with PBS and blocked with PBS/BSA/Tween-20 for 1 hr at 37° C. For the primary incubation, dilutions of non-specific mouse IgG or human IgG, whole molecule (used for calibration curve) and samples to be measured were added to the wells. Plates were washed and incubated with 100 ul per well of HRP conjugated goat anti-mouse (H+L) diluted 1:40,000 (Jackson Immuno Research) or HRP conjugated goat anti-human (H+L) diluted 1:50,000 (Jackson Immuno Research) for 1 hr at 37° C. After washing, the enzymatic reaction was detected with Tetramethylbenzidine (Sigma) and stopped by adding 1 M $H_2SO_4$. The optical density (OD) was measured at 450 nm using a Thermo Multiskan EX. Raw data were transferred to GraphPad software for analysis.

5. Direct ELISA

Microtiter ELISA plates (Costar) were coated overnight with S1P diluted in 1 M Carbonate Buffer (pH 9.5) at 37° C. for 1 hr. Plates were washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 for 1 hr at room temp or overnight at 4° C. For the primary incubation (1 hr at room temp.), a standard curve using the anti-S1P mAb and the samples to be tested for binding was built using the following set of dilutions: 0.4 µg/mL, 0.2 µg/mL, 0.1 µg/mL, 0.05 µg/mL, 0.0125 µg/mL, and 0 µg/mL, and 100 µl added to each well. Plates were washed and incubated with 100 µl per well of HRP conjugated goat anti-mouse (1:20,000 dilution) (Jackson Immuno Research) or HRP conjugated goat anti-human (H+L) diluted 1:50,000 (Jackson Immuno Research) for 1 hr at room temperature. After washing, the enzymatic reaction was detected with tetramethylbenzidine (Sigma) and stopped by adding 1 M $H_2SO_4$. The optical density (OD) was measured at 450 nm using a Thermo Multiskan EX. Raw data were transferred to GraphPad software for analysis.

Table 2, below, shows a comparative analysis of mutants with the chimeric antibody. To generate these results, bound antibody was detected by a second antibody, specific for the mouse or human IgG, conjugated with HRP. The chromogenic reaction was measured and reported as Optical density (OD). The concentration of the panel of antibodies was 0.1 ug/ml. No interaction of the second antibody with S1P-coated matrix alone was detected.

TABLE 2

| Variable Domain | Mutation | Plasmids | Binding |
|---|---|---|---|
| | Chimeric | pATH50 + pATH 10 | 1.5 |
| HC | CysAla | pATH50 + pATH11C1 | 2 |
| | CysSer | pATH50 + pATH 12C2 | 0.6 |
| | CysArg | pATH50 + pATH14C1 | 0.4 |
| | CysPhe | pATH50 + pATH16C1 | 2 |
| LC | MetLeu | pATH53C1 + pATH10 | 1.6 |

Example 6

Chimeric mAb to S1P

As used herein, the term "chimeric" antibody (or "immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. U.S.A. 81:6851 (1984)).

Figure 9:
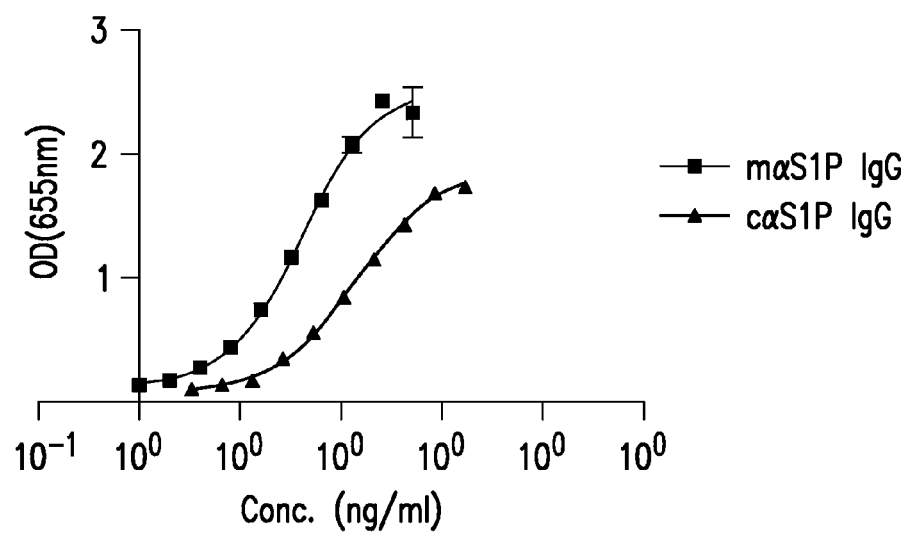
FIG. 9. Direct ELISA showing binding of murine and chimeric mAbs to ELISA plates coated with thiolated S1P analog as described in EXAMPLE 6. Data show that the chimeric mAb (cα-S1P IgG) has similar, if not greater binding performance compared to the fully murine mAb (mα-S1P IgG).

A chimeric antibody to S1P was generated using the variable regions (Fv) containing the active S1P binding regions of the murine antibody from a particular hybridoma (ATCC safety deposit storage number SD-5362) with the Fc region of a human IgG1 immunoglobulin. The Fc regions contained the CL, ChL, and Ch3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can been generated by grafting the complementarity determining regions (CDRs, e.g. CDR1-4) of the murine anti-S1P mAb with a human antibody framework regions (e.g., Fr1, Fr4, etc.) such as the framework regions of an IgG1. FIG. 9 shows the binding of the chimeric and full murine mAbs in a direct ELISA measurement using thiolated-S1P as lay down material.

For the direct ELISA experiments shown in FIG. 9, the chimeric antibody to S1P had similar binding characteristics to the fully murine monoclonal antibody. ELISAs were performed in 96-well high-binding ELISA plates (Costar) coated with 0.1 ug of chemically-synthesized, thiolated S1P conjugated to BSA in binding buffer (33.6 mM $Na_2CO_3$, 100 mM $NaHCO_3$; pH 9.5). The thiolated S1P-BSA was incubated at 37° C. for 1 hr. or at 4° C. overnight in the ELISA plate. Plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 μL of 0.1 μg/mL anti-S1P monoclonal antibody diluted in PBST and added to a well of the ELISA plate. Each sample was performed in triplicate wells. Following a 1 hr incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL-X-800 ELISA plate reader (Bio-Tech).

As was the case with regard to the experiments described in Example 4, the preferred method of measuring either antibody titer in the serum of an immunized animal or in cell-conditioned media (i.e., supernatant) of an antibody-producing cell such as a hybridoma, involves coating the ELISA plate with a target ligand (e.g., a thiolated analog of S1P, LPA, etc.) that has been covalently linked to a protein carrier such as BSA.

Without being limited to particular method or example, chimeric antibodies could be generated against other lipid targets such as LPA, ceramides, sulfatides, cerebrosides, cardiolipins, phosphotidylserines, phosphotidylinositols, phosphatidic acids, phosphotidylcholines, phosphatidylethanolamines, eicosinoids, and other leukotrienes, etc. Further, many of these lipids could also be glycosylated and/or acetylated, if desired.

Example 7

Antibody-Based Assay for Sphingosine Kinase (SPH Kinase)

Sphingosine Kinase (SPH kinase or SPHK) catalyzes the conversion of SPH to S1P. A genetic sequence encoding human SPH-kinase has been described (Melendez et al., Gene 251:19-26, 2000). Three human homologs of SPH kinase (SKA, SKB, and SKC) have been described (published PCT patent application WO 00/52173). Murine SPH kinase has also been described (Kohama et al., J. Biol. Chem. 273:23722-23728, 1998; and published (PCT patent application WO 99/61581). Published PCT patent application WO 99/61581 reports nucleic acids encoding a sphingosine kinase. Published PCT patent application WO 00/52173 reports nucleic acids encoding homologues of sphingosine kinase. Other SPH kinases have also been reported. See, e.g., Pitson et al., Biochem J. 350:429-441, 2000; published PCT application WO 00/70028; Liu et al., J. Biol. Chem., 275: 19513-19520, 2000; PCT/AU01/00539, published as WO 01/85953; PCT/US01/04789, published as WO 01/60990; and PCT/EP00/09498, published as WO 01/31029.

Inhibitors of SPH kinase include, but are not limited to, N,N-dimethylsphingosine (Edsall et al., Biochem. 37:12892-12898, 1998); D-threo-dihydrosphingosine (Olivera et al., Nature 365:557-560, 1993); and Sphingoid bases (Jonghe et al, "Structure-Activity Relationship of Short-Chain Sphingoid Bases As Inhibitors of Sphingosine Kinase", Bioorganic & Medicinal Chemistry Letters 9:3175-3180, 1999)

Assays of SPH kinase useful for evaluating these and other known or potential SPH kinase inhibitors include those disclosed by Olivera et al., Methods in Enzymology, 311:215-223, 1999; Caligan et al., Analytical Biochemistry, 281:36-44, 2000.

Inhibition of SPH kinase is believed to lead to an accumulation of its substrate, SPH, which, like S1P, can be an undesirable sphingolipid in certain conditions. In order to avoid or mitigate these undesirable effects, an agent could be administered that (i) stimulates an enzyme that utilizes SPH as a substrate, provided that the enzyme should not be one that yields S1P as a reaction product (such as, e.g., ceramide synthase; see below); or (ii) inhibits an enzyme that yields SPH as a product.

Without being limited to a particular method, anti-S1P antibodies (e.g., a monoclonal anti-S1P antibody) could be used as a reagent in an in vitro assay for SPH kinase activity. For example, purified SPHK could be added to the wells of a microtiter plate in the presence of PBS and the substrate for the kinase, SPH (complexed with, for example, fatty-acid free BSA). The resulting product of the reaction, S1P, could then be followed by ELISA using an anti-S1P antibody (e.g., the monoclonal anti-S1P antibody described above in Example 4). In such an assay, inhibition of SPHK by a test compound would result in lower levels of S1P than in a control reaction that did not include an SPHK inhibitory compound. Such an assay could be configured for high throughput, and could thus serve as the basis of a high throughput screening assay for modulators of SPHK activity.

Example 8

Antibody-Based Assay for S1P Lyase or SPP Activities

The stimulation of enzymes that catalyze reactions that degrade S1P (i.e., reactions that utilize S1P as a reactant) will result in the stimulation of degradation of S1P molecules. Such enzymes include, but are not limited to:

S-1-P Lyase:

S1P lyase catalyzes the conversion of S1P to ethanolamine-P (also known as t-2-hexadecanal) and palmitaldehyde (Veldhoven et al., *Adv. Lipid Res.* 26:67-97, 1993; Van Veldhoven, Methods in Enzymology, 311:244-254, 1999). Yeast (Lanterman et al, *Biochem. J.* 332:525-531, 1998), murine (Zhou et al., *Biochem. Biophys. Res. Comm.* 242:502-507, 1998), and human (published PCT patent application WO 99/38983) S1P lyase genes have been reported. Published PCT patent application WO 99/16888 reports S1P lyase DNA and protein sequences. U.S. Pat. No. 6,187,562 and published PCT patent application WO 99/38983 also report an S1P lyase.

Gain-of-function assays can be developed to discover small molecule compounds that would activate the lyase or increase the expression of the gene encoding it. Without being limited to a particular method, one could use anti-S1P antibodies in an ELISA format to measure the production of S1P from added SPH in in vitro or cell-based formats. Compounds identified as stimulating S1P lyase activity, either directly at the enzyme or indirectly by elevating the expression level of the gene encoding the enzyme (for example, by gene activation, enhancing S1P lyase mRNA stability, etc.), could be investigated further, as such compounds may prove useful in lowering the extracellular concentration of S1P in patients where S1P levels correlate with toxicity, such as in the treatment of cancer, cardio and cerebrovascular disease, autoimmune disorders, inflammatory disorders, angiogenesis, fibrotic diseases, and age-related macular degeneration.

S1P Phosphatase:

S1P phosphatase (also known as SPP phosphohydrolase) is a mammalian enzyme that catalyzes the conversion of S-1-P to sphingosine (Mandala et al., *Proc. Nat. Acad. Sci.* 95:150-155, 1998; Mandala et al, *Proc. Nat. Acad. Sci.* 97:7859-7864, 2000; Mandala, Prostaglandins & other Lipid Mediators, 64:143-156, 2001; Brindley et al., Methods in Enzymology, 311:233-244, 1999). Two S-1-P phosphatases, LBP1 and LBP2, have been isolated from yeast (Mandala et al., *J. Biol. Chem.* 272:32709-32714, 1997); PCT/UW01/03879, published as WO01/57057.

As with S1P lyase, gain-of-function assays can be developed to discover compounds that would activate S1P phosphatase or increase the expression of the gene encoding it. For example, one can use anti-S1P antibodies in an ELISA format to measure the production of S1P from added SPH in in vitro or cell-based formats. Compounds identified as stimulating S1P phosphatase activity, either directly at the enzyme or indirectly by elevating the expression level of the gene encoding the enzyme (for example, by gene activation, enhancing S1P phosphatase mRNA stability, etc.), could be investigated further, as such compounds may prove useful in lowering the extracellular concentration of S1P in patients where S1P levels correlate with toxicity, such as cancer, cardio and cerebrovascular disease, autoimmune disorders, inflammatory disorders, angiogenesis, fibrotic diseases, and age-related macular degeneration.

Example 9

Production and Characterization of Monoclonal Antibodies to LPA

Antibody Production

Although polyclonal antibodies against naturally-occurring LPA have been reported in the literature (Chen J H, et al., Bioorg Med Chem. Lett. 2000 Aug. 7; 10(15):1691-3), monoclonal antibodies have not been described. Using an approach similar to that described in Example 4, a C-12 thio-LPA analog (compound 28 in Example 3) as the key component of a hapten formed by the cross-linking of the analog via the reactive SH group to a protein carrier (KLH) via standard chemical cross-linking using either IOA or SMCC as the cross-linking agent, monoclonal antibodies against LPA were generated. To do this, mice were immunized with the thio-LPA-KLH hapten (in this case, thiolated-LPA:SMCC:KLH) using methods described in Example 4 for the generation of anti-S1P monoclonal antibodies. Of the 80 mice immunized against the LPA analog, the five animals that showed the highest titers against LPA (determined using an ELISA in which the same LPA analog (compound 28) as used in the hapten was conjugated to BSA using SMCC and laid down on the ELISA plates) were chosen for moving to the hybridoma phase of development.

The spleens from these five mice were harvested and hybridomas were generated by standard techniques. Briefly, one mouse yielded hybridoma cell lines (designated 504A). Of all the plated hybridomas of the 504A series, 66 showed positive antibody production as measured by the previously-described screening ELISA.

Table 3, below, shows the antibody titers in cell supernatants of hybridomas created from the spleens of two of mice that responded to an LPA analog hapten in which the thiolated LPA analog was cross-linked to KLH using heterobifunctional cross-linking agents. These data demonstrate that the anti-LPA antibodies do not react either to the crosslinker or to the protein carrier. Importantly, the data show that the hybridomas produce antibodies against LPA, and not against S1P.

TABLE 3

LPA hybridomas

| mouse # | 3rd bleed titer OD at 1:312,500 | Supernatants from 24 well | LPA binding OD at 1:20 | S1P binding OD at 1:20 | Cross reactivity w/ S1P* |
|---|---|---|---|---|---|
| 1 | 1.242 | 1.A.63 | 1.197 | 0.231 | low |
|   |       | 1.A.65 | 1.545 | 0.176 | none |
| 2 | 0.709 | 2.B.7  | 2.357 | 0.302 | low |
|   |       | 2.B.63 | 2.302 | 0.229 | low |
|   |       | 2.B.83 | 2.712 | 0.175 | none |
|   |       | 2.B.104 | 2.57 | 0.164 | none |
|   |       | 2.B.IB7 | 2.387 | 0.163 | none |
|   |       | 2.B.3A6 | 2.227 | 0.134 | none |

*Cross reactivity with S1P from 24 well supernatants
high = OD > 1.0-2.0 at [1:20]
mid = OD 0.4-1.0 at [1:20]
low = OD 0.4-0.2 at [1:20]
none = OD < 0.2 OD at [1:20]

The development of anti-LPA mAbs in mice was monitored by ELISA (direct binding to 12:0 and 18:1 LPA and competition ELISA). A significant immunological response was observed in at least half of the immunized mice and five mice with the highest antibody titer were selected to initiate hybridoma cell line development following spleen fusion.

After the initial screening of over 2000 hybridoma cell lines generated from these 5 fusions, a total of 29 anti-LPA secreting hybridoma cell lines exhibited high binding to 18:1 LPA. Of these hybridoma cell lines, 24 were further subcloned and characterized in a panel of ELISA assays. From the 24 clones that remained positive, six hybridoma clones were selected for further characterization. Their selection was based on their superior biochemical and biological properties.

Direct Binding Kinetics

The binding of 6 anti-LPA mAbs (B3, B7, B58, A63, B3A6, D22) to 12:0 and 18:1 LPA (0.1 uM) was measured by ELISA. $EC_{50}$ values were calculated from titration curves using 6 increasing concentrations of purified mAbs (0 to 0.4 ug/ml). $EC_{50}$ represents the effective antibody concentration with 50% of the maximum binding. Max denotes the maximal binding (expressed as OD450). Results are shown in Table 4.

TABLE 4

Direct Binding Kinetics of Anti-LPA mAbs

|  |  | B3 | B7 | B58 | D22 | A63 | B3A6 |
|---|---|---|---|---|---|---|---|
| 12:0 LPA | $EC_{50}$ (nM) | 1.420 | 0.413 | 0.554 | 1.307 | 0.280 | 0.344 |
|  | Max (OD450) | 1.809 | 1.395 | 1.352 | 0.449 | 1.269 | 1.316 |
| 18:1 LPA | $EC_{50}$ (nM) | 1.067 | 0.274 | 0.245 | 0.176 | 0.298 | 0.469 |
|  | Max (OD450) | 1.264 | 0.973 | 0.847 | 0.353 | 1.302 | 1.027 |

The kinetics parameters $k_a$ (association rate constant), $k_d$ (disassociation rate constant) and $K_D$ (association equilibrium constant) were determined for the 6 lead candidates using the BIAcore 3000 Biosensor machine. In this study, LPA was immobilized on the sensor surface and the anti-LPA mAbs were flowed in solution across the surface. As shown, all six mAbs bound LPA with similar $K_D$ values ranging from 0.34 to 3.8 µM and similar kinetic parameters.

The Anti-LPA Murine mAbs Exhibit High Affinity to LPA

LPA was immobilized to the sensor chip at densities ranging 150 resonance units. Dilutions of each mAb were passed over the immobilized LPA and kinetic constants were obtained by nonlinear regression of association/dissociation phases. Errors are given as the standard deviation using at least three determinations in duplicate runs. Apparent affinities were determined by $K_D=k_d/k_a$. $k_a$=Association rate constant in $M^{-1}s^{-1}$ $k_d$=Dissociation rate constant in $s^{-1}$

TABLE 5

Affinity of anti-LPA mAb for LPA

| mAbs | $k_a$ ($M^{-1}s^{-1}$) | $k_d$ ($s^{-1}$) | $K_D$ (pM) |
|---|---|---|---|
| A63 | $4.4 \pm 1.0 \times 10^5$ | $1 \times 10^{-6}$ | $2.3 \pm 0.5$ |
| B3 | $7.0 \pm 1.5 \times 10^5$ | $1 \times 10^{-6}$ | $1.4 \pm 0.3$ |
| B7 | $6.2 \pm 0.1 \times 10^5$ | $1 \times 10^{-6}$ | $1.6 \pm 0.1$ |
| D22 | $3.0 \pm 0.9 \times 10^4$ | $1 \times 10^{-6}$ | $33 \pm 10$ |
| B3A6 | $1.2 \pm 0.9 \times 10^6$ | $1.9 \pm 0.4 \times 10^{-5}$ | $16 \pm 1.2$ |

Specificity Profile of Six Anti-LPA mAbs.

Many isoforms of LPA have been identified to be biologically active and it is preferable that the mAb recognize all of them to some extent to be of therapeutic relevance. The specificity of the anti-LPA mAbs was evaluated utilizing a competition assay in which the competitor lipid was added to the antibody-immobilized lipid mixture. Competition ELISA assays were performed with 6 mAbs to assess their specificity. 18:1 LPA was captured on ELISA plates. Each competitor lipid (up to 10 uM) was serially diluted in BSA (1 mg/ml)-PBS and then incubated with the mAbs (3 nM). Mixtures were then transferred to LPA coated wells and the amount of bound antibody was measured with a secondary antibody. Data are normalized to maximum signal ($A_{450}$) and are expressed as percent inhibition. Assays were performed in triplicate. $IC_{50}$: Half maximum inhibition concentration; MI: Maximum inhibition (% of binding in the absence of inhibitor); ---: not estimated because of weak inhibition. A high inhibition result indicates recognition of the competitor lipid by the antibody. As shown in Table 6, all the anti-LPA mAbs recognized the different LPA isoforms.

TABLE 6

| | Specificity profile of six anti-LPA mAbs. | | | | | | | | | |
|---|---|---|---|---|---|---|---|---|---|---|
| | 14:0 LPA | | 16:0 LPA | | 18:1 LPA | | 18:2 LPA | | 20:4 LPA | |
| | $IC_{50}$ uM | MI % | $IC_{50}$ uM | MI % | $IC_{50}$ uM | MI % | $IC_{50}$ uM | MI % | $IC_{50}$ uM | MI % |
| 504B3 | 0.02 | 72.3 | 0.05 | 70.3 | 0.287 | 83 | 0.064 | 72.5 | 0.02 | 67.1 |
| 504B7 | 0.105 | 61.3 | 0.483 | 62.9 | >2.0 | 100 | 1.487 | 100 | 0.161 | 67 |
| 504B58-3F8 | 0.26 | 63.9 | 5.698 | >100 | 1.5 | 79.3 | 1.240 | 92.6 | 0.304 | 79.8 |
| 504B104 | 0.32 | 23.1 | 1.557 | 26.5 | 28.648 | >100 | 1.591 | 36 | 0.32 | 20.1 |
| 504D22-1 | 0.164 | 34.9 | 0.543 | 31 | 1.489 | 47.7 | 0.331 | 31.4 | 0.164 | 29.5 |
| 504A63-1 | 1.147 | 31.9 | 5.994 | 45.7 | — | — | — | — | 0.119 | 14.5 |
| 504B3A6-1 | 0.108 | 59.9 | 1.151 | 81.1 | 1.897 | 87.6 | — | — | 0.131 | 44.9 |

Interestingly, the anti-LPA mAbs were able to discriminate between 12:0 (lauroyl), 14:0 (myristoyl), 16:0 (palmitoyl), 18:1 (oleoyl), 18:2 (linoleoyl) and 20:4 (arachidonoyl) LPAs. The rank order for $EC_{50}$ was for the unsaturated 18:2>18: 1>20:4 and for the saturated lipids 14:0>16:0>18:0. mAbs with high specificity are desirable for ultimate drug development. The specificity of the anti-LPA mAbs was assessed for their binding to LPA related biolipids such as distearoyl-phosphatidic acid, lysophosphatidylcholine, S1P, ceramide and ceramide-1-phosphate. None of the six antibodies demonstrated crossreactivity to distearoyl PA and LPC, the immediate metabolic precursor of LPA.

Example 10

Anti-Cancer Activities of anti-LPA Monoclonal Antibodies

Cancer Cell Proliferation

LPA is a potent growth factor supporting cell survival and proliferation by stimulation of $G_i$, $G_q$ and $G_{12/13}$ via GPCR-receptors and activation of downstream signaling events. Cell lines were tested for their proliferative response to LPA (0.01 mM to 10 mM). Cell proliferation was assayed by using the cell proliferation assay kit from Chemicon (Temecula Calif.) (Panc-1) and the Cell-Blue titer from Pierce (Caki-1). Each data point is the mean of three independent experiments. LPA increased proliferation of 7 human-derived tumor cell lines in a dose dependent manner including SKOV3 and OVCAR3 (ovarian cancer), Panc-1 (pancreatic cancer), Caki-1 (renal carcinoma cell), DU-145 (prostate cancer), A549 (lung carcinoma), and HCT-116 (colorectal adenocarcinoma) cells and one rat-derived tumor cell line, RBL-2H3 (rat leukemia cells). Even though tumor-derived cells normally have high basal levels of proliferation, LPA appears to further augment proliferation in most tumor cell lines. Anti-LPA mAbs (B7 and B58) were assessed for the ability to inhibit LPA-induced proliferation in selected human cancer cell lines. The increase in proliferation induced by LPA was shown to be mitigated by the addition of anti-LPA mAb.

Anti-LPA mAb Sensitizes Tumor Cells to Chemotherapeutic Agents

The ability of LPA to protect ovarian tumor cells against apoptosis when exposed to clinically-relevant levels of the chemotherapeutic agent, paclitaxel (Taxol) was investigated. SKVO3 cells were treated with 1% FBS (S), Taxol (0.5 mM), +/−anti-LPA mAbs for 24 h. LPA protected SKVO3 cells from Taxol-induced apoptosis. Apoptosis was assayed by measurement of the caspase activity as recommended by the manufacturer (Promega). As anticipated, LPA protected most of the cancer cell lines tested from taxol-induced cell death.

When anti-LPA antibody was added to a selection of the LPA responsive cells, the anti-LPA antibody blocked the ability of LPA to protect cells from death induced by the cytotoxic chemotherapeutic agent. Moreover, the anti-LPA antibody was able to remove the protection provided by serum. Serum is estimated to contain about 5-20 mM LPA. Taxol induced caspase-3,7 activation in SKOV3 cells and the addition of serum to cells protected cells from apoptosis. Taxol-induced caspase activation was enhanced by the addition of all 3 of the anti-LPA mAbs to the culture medium. This suggests that the protective and anti-apoptotic effects of LPA were removed by the selective antibody mediated neutralization of the LPA present in serum.

Anti-LPA mAb Inhibits LPA-Mediated Migration of Tumor Cells

An important characteristic of metastatic cancers is that the tumor cells escape contact inhibition and migrate away from their tissue of origin. LPA has been shown to promote metastatic potential in several cancer cell types. Accordingly, we tested the ability of anti-LPA mAb to block LPA-dependent cell migration in several human cancer cell lines by using the cell monolayer scratch assay. Cells were seeded in 96 well plates and grown to confluence. After 24 h of starvation, the center of the wells was scratched with a pipette tip. In this art-accepted "scratch assay," the cells respond to the scratch wound in the cell monolayer in a stereotyped fashion by migrating toward the scratch and close the wound. Progression of migration and wound closure are monitored by digital photography at 10× magnification at desired timepoints. Cells were not treated (NT), treated with LPA (2.5 mM) with or w/o mAb B7 (10 µg/ml) or an isotype matching non-specific antibody (NS) (10 µg/ml). In untreated cells, a large gap remains between the monolayer margins following the scratch. LPA-treated cells in contrast, have only a small gap remaining at the same timepoint, and a few cells are making contact across the gap. In cells treated with both LPA and the anti-LPA antibody B7, the gap at this timepoint was several fold larger than the LPA-only treatment although not as large as the untreated control cells. This shows that the anti-LPA antibody had an inhibitory effect on the LPA-stimulated migration of renal cell carcinoma (Caki-1) cells. Similar data were obtained with mAbs B3 and B58. This indicates that the anti-LPA mAb can reduce LPA-mediated migration of cell lines originally derived from metastatic carcinoma.

Anti-LPA mAbs Inhibit Release of Pro-Tumorigenic Cytokines from Tumor Cells

LPA is involved in the establishment and progression of cancer by providing a pro-growth tumor microenvironment and promoting angiogenesis. In particular, increases of the pro-growth factors such as IL-8 and VEGF have been observed in cancer cells. IL-8 is strongly implicated in cancer progression and prognosis. IL-8 may exert its effect in cancer through promoting neovascularization and inducing chemotaxis of neutrophils and endothelial cells. In addition, overexpression of IL-8 has been correlated to the development of a drug resistant phenotype in many human cancer types.

Three anti-LPA mAbs (B3, B7 and B58) were tested for their abilities to reduce in vitro IL-8 production compared to a non-specific antibody (NS). Caki-1 cells were seeded in 96 well plates and grown to confluency. After overnight serum starvation, cells were treated with 18:1 LPA (0.2 mM) with or without anti-LPA mAb B3, B7, B58 or NS (Non-Specific). After 24 h, cultured supernatants of renal cancer cells (Caki-1), treated with or without LPA and in presence of increasing concentrations of the anti-LPA mAbs B3, B7 and B58, were collected and analyzed for IL-8 levels using a commercially available ELISA kit (Human Quantikine Kit, R&D Systems, Minneapolis, Minn.). In cells pre-treated with the anti-LPA mAbs, IL-8 expression was significantly reduced in a dose-dependent manner (from 0.1-30 μg/mL mAb) whereas LPA increased the expression of IL-8 by an average of 100% in non-treated cells. Similar results were obtained with the other well-known pro-angiogenic factor, VEGF. The inhibition of IL-8 release by the anti-LPA mAbs was also observed in other cancerous cell lines such as the pancreatic cell line Panc-1. These data suggest that the blockade of the pro-angiogenic factor release is an additional and potentially important effect of these anti-LPA mAbs.

Anti-LPA mAbs Inhibit Angiogenesis In Vivo

One of the anti-LPA mAbs (B7) was tested for its ability to mitigate angiogenesis in vivo using the Matrigel Plug assay. This assay utilizes Matrigel, a proprietary mixture of tumor remnants including basement membranes derived from murine tumors. When Matrigel, or its derivate growth factor-reduced (GFR) Matrigel, is injected sc into an animal, it solidifies and forms a 'plug.' If pro-angiogenic factors are mixed with the matrix prior to placement, the plug will be invaded by vascular endothelial cells which eventually form blood vessels. Matrigel can be prepared either alone or mixed with recombinant growth factors (bFGF, VEGF), or tumor cells and then injected sc in the flanks of 6-week old nude (NCr Nu/Nu) female mice. In this example, Caki-1 (renal carcinoma) cells were introduced inside the Matrigel and are producing sufficient levels of VEGF and/or IL8 and LPA. Matrigel plugs were prepared containing $5\times10^5$ Caki-1 cells from mice treated with saline or with 10 mg/kg of anti-LPA mAb-B7, every 3 days starting 1 day prior to Matrigel implantation. Plugs were stained for endothelial CD31, followed by quantitation of the micro-vasculature formed in the plugs. Quantitation data were means+/−SEM of at least 16 fields/section from 3 plugs. The plugs from mice treated with the anti-LPA mAb B7 demonstrated a prominent reduction in blood vessel formation, as assayed by endothelial staining for CD31, compared to the plugs from saline-treated mice. Quantification of stained vessels demonstrates a greater than 50% reduction in angiogenesis in Caki-1-containing plugs from animals treated with mAb B7 compared to saline-treated animals. This was a statistically significant reduction ($p<0.05$ for mAb B7 vs. Saline as determined by Student's T-test) in tumor cell angiogenesis as a result of anti-LPA mAb treatment.

Anti-LPA mAbs Reduces Tumor Progression in Renal and Pancreatic Xenografts

The anti-LPA antibodies have been shown (above) to be effective in reducing LPA-induced tumor cell proliferation, migration, protection from cell death and cytokine release in multiple human tumor cell lines. mAbs B58 and B7 were next tested in a xenograft model of renal and pancreatic cancer. Below are preliminary results that demonstrate the potential anti-tumorigenic effects of the anti-LPA antibody approach.

Tumors were developed by subcutaneous injection of Caki-1 and Panc-1 human tumor cells into the left flank of 4 week old female nude (NCr Nu/Nu) mice using standard protocols. After 10 days for Caki-1 and 30 days for Panc-1, when solid tumors had formed (~200 mm3), mice were randomized into treatment groups. Treatment was initiated by i.p. administration of 25 mg/kg of the anti-LPA mAbs or vehicle (saline solution). Antibodies were administered every three days for the duration of the study. Treatments consisted of 25 mg/kg of the anti-LPA mAb B58 for caki-1 tumors, mAb B7 for Panc-1 or Saline. Data are the mean+/−SEM of 7 saline and 6 B58-treated mice for the caki-1 study and 4 saline and 5 B7-treated mice for the panc-1 study. Tumor volumes were measured every other day using electronic calipers and the tumor volume determined by the formula, $W^2 \times L/2$. Animals were subsequently sacrificed after tumors reached 1500 mm$^3$ in the saline group. Final tumor volumes and weights were recorded.

In this preliminary experiment, the ability of the anti-LPA mAbs to reduce tumor volume was apparent after the tumors reached approximately 400-500 mm$^3$. At this point, the tumors from the control animals continued to grow, while the tumors from the anti-LPA mAb-treated animals exhibited a slower rate growth in both xenograft models. Data demonstrates that the anti-LPA mAb also reduced the final tumor weights of caki-1 and panc-1 tumors when compared to tumor weights from saline-treated animals.

Anti-LPA mAbs Modulate Levels of Circulating Pro-Angiogenic Cytokines in Animals with Tumors The anti-LPA mAbs (B58 and B7) also influenced the levels of circulating pro-angiogenic cytokine. In animals treated with the anti-LPA mAb7 (Panc-1), the serum level of interleukin-8 (IL-8) was not detectable in any antibody-treated animals, whereas IL-8 serum levels were detectable in Panc-1 and Caki-1 xenografts after 85 and 63 days, respectively. More importantly there was a strong correlation ($r=0.98$) between tumor size and IL-8 levels. In the animals bearing Caki-1 tumors the serum levels of human IL-8 were also reduced by the treatment with anti-LPA mAb58 ($r=0.34$) when compared to saline treatment ($r=0.55$). As mentioned above, the reduction of circulating cytokine levels is believed to be due to a direct inhibition of cytokine release from the tumor cells themselves. These data demonstrates the ability of the anti-LPA mAb to reduce tumor progression while also reducing the levels of circulating pro-angiogenic compounds.

Anti-LPA mAbs Reduces Tumor Progression in a Murine Model of Metastasis

One important characteristic of tumor progression is the ability of a tumor to metastasize and form secondary tumor nodules at remote sites. In vitro studies described hereinabove have demonstrated the ability of LPA to induce tumor cells to escape contact inhibition and promote migration in a scratch assay for cell motility. In these studies, the anti-LPA mAbs also inhibited LPA's tumor growth promoting effectors. The efficacy of the anti-LPA mAb to inhibit tumor metastasis in vivo. The phenomenon of tumor metastasis has been difficult to mimic in animal models. Many investigators utilize an "experimental" metastasis model in which tumor cells are directly injected into the blood stream.

Blood vessel formation is an integral process of metastasis because an increase in the number of blood vessels means cells have to travel a shorter distance to reach circulation. It is believed that anti-LPA mAb will inhibit in vivo tumor cell metastasis, based on the finding that the anti-LPA mAb can block several integral steps in the metastatic process.

Study: The highly metastatic murine melanoma (B16-F10) was used to examine the therapeutic effect of three anti-LPA mAbs on metastasis in vivo. This model has demonstrated to be highly sensitive to cPA inhibitors of autotaxin. 4 week old female (C57BL/6) mice received an injection of B16-F10 murine melanoma tumor cells (100 uL of $5\times10^4$ cells/animal) via the tail vein. Mice (10 per group) were administered 25 mg/kg of the anti-LPA mAb (either B3 or B7) or saline every three days by i.p. injection. After 18 days, lungs were harvested and analyzed. The pulmonary organs are the preferred metastatic site of the melanoma cells, and were therefore closely evaluated for metastatic nodules. The lungs were inflated with 10% buffered formalin via the trachea, in order to inflate and fix simultaneously, so that even small foci could be detectable on histological examination. Lungs were separated into five lobes and tumors were categorized by dimension (large≥5 mm; medium 1-4 mm; small<1 mm) and counted under a dissecting microscope. Upon examination of the lungs, the number of tumors was clearly reduced in antibody-treated animals. For animals treated with mAb B3, large tumors were reduced by 21%, medium tumors by 17% and small tumors by 22%. Statistical analysis by student's T-test gave a $p<0.05$ for number of small tumors in animals treated with mAb B3 vs saline.

As shown in the above examples, it has now been shown that the tumorigenic effects of LPA are extended to renal carcinoma (e.g., Caki-1) and pancreatic carcinoma (Panc-1) cell lines. LPA induces tumor cell proliferation, migration and release of pro-angiogenic and/or pro-metastatic agents, such as VEGF and IL-8, in both cell lines. It has now been shown that three high-affinity and specific monoclonal anti-LPA antibodies demonstrate efficacy in a panel of in vitro cell assays and in vivo tumor models of angiogenesis and metastasis.

Example 11

Immunohistochemistry of Tumor Biopsy Material

The purpose of this example is to demonstrate that mAbs developed against S1P could be used to detect S1P in biopsy material. This immunohistochemical (IHC) method assesses the level of S1P in the tumor (which is believed to be produced by the tumor itself) and may be more sensitive and specific than measuring protein or RNA expression of sphingosine kinase. In addition, the IHC method would not suffer diminution of the S1P signal as S1P secreted from the tumor is diluted into the extracellular space (e.g., plasma compartment). We analyzed S1P content in U937 human tumor sections (frozen; 10 μm thick) from a mouse Matrigel/xenograft model. U937 cells (human lymphoma cell line; ATCC cat no #CRL-1593.2) were mixed with Matrigel matrix, at a concentration of 10.5 mg/ml. 600 μL of Matrigel mix containing U937 ($30\times10^6$ cells/plug in a 600 μl volume) were implanted into the right flank of 4-6 weeks nu/nu female mice and allowed to grow for 30 days. The animals were sacrificed and the Matrigel plugs were excised and embedded in OTC and flash frozen in dry ice and isopentane. Then were sectioned using a cryostat to 5 um sections. Sections were then fixed in 10% neutral buffered formalin, (Sigma, St. Louis Mo.; catalog number: HT 50-1-1; lot #025K4353) for 20 min at room temp and then sections. The sections were washed with 100 mM glycine (pH 7.4) in PBS for 5 min at room temp, washed 2× with PBS/0.1% Tween. Sections were blocked in 1% BSA/PBS/0.05% Tween for 20 min at room temp. Primary antibodies (e.g. murine anti-S1P mAb) were diluted (1:25 or at 1:50, as indicated) in 1%/BSA/PBS/0.05% Tween and incubated with tumor sections for 3 hr at room temp. Sections were then washed 3× with PBS/0.1% Tween with gentle agitation. Diluted secondary antibodies (FITC-conjugated anti mouse Ab (1:250) and RRX-conjugated anti-rat Ab (1:2500 or 1:500) in 1% BSA/PBS/0.05% Tween were incubated with tumor sections for 1 hr at room temp. Sections were then washed 6× at 5 min intervals with PBS/0.05% Tween. Sections were counterstained with DAPI (4',6-diamidino-2-phenylindole dilactate (DAPI, 10 mg; Sigma, St. Louis Mo.; catalog number D3571, lot 22775) by incubation with DAPI (1:5000) diluted in PBS for 20 min at room temp. Sections were then washed 2× at 5 min intervals with PBS and 1× with DI $H_2O$ and mounted in Gelvitol mounting media and let dry. Primary antibodies used were LT1002 (LH-2; 15 mg/ml) anti-S1P mAb diluted to 1.0 mg/ml and added at a working concentration of 1:25 in 1%/BSA/PBS/0.05% Tween. Secondary antibodies used were: Fluorescein (FITC)-conjugated rabbit anti-mouse IgG (H+L) (Jackson ImmunoResearch, West Grove Pa.; catalog #315-095-003; lot number: 67031) Ab diluted 1:250 in 1%/BSA/PBS/0.05% Tween. Images were captured with a DeltaVision deconvolution microscope system (Applied Precision, Inc., Issaquah, Wash.) The system includes a Photometrics CCD mounted on a Nikon TE-200 inverted epi-fluorescence microscope. In general, 8-10 optical sections spaced by ~0.2 um were taken. Exposure times were set such that the camera response was in the linear range for each fluorophore. Lenses included 20× and 10×. The data sets were deconvolved and analyzed using SoftWorx software (Applied Precision, Inc) on a Silicon Graphics Octane workstation.

S1P could easily be seen in tumor biopsy images using this IHC method, using the anti-S1P mAb as the primary antibody. In contrast, S1P staining was absent in control samples from which the primary antibody was omitted.

Without being bound by theory or limited to these examples, it is believed that the measurement of the biomarker S1P could be used in conjunction with measurements of gene expression for S1P receptors and of sphingosine kinase, both of which could serve as surrogate cancer markers. Examples of methods of gene expression analysis known in the art include DNA arrays or microarrays (Brazma and Vilo, FEBS Lett., 2000, 480, 17 24; Celis, et al., FEBS Lett., 2000, 480, 2 16), SAGE (serial analysis of gene expression) (Madden, et al., Drug Discov. Today, 2000, 5, 415 425), READS (restriction enzyme amplification of digested cDNAs) (Prashar and Weissman, Methods Enzymol., 1999, 303, 258 72), TOGA (total gene expression analysis) (Sutcliffe, et al., Proc. Natl. Acad. Sci. U.S.A., 2000, 97, 1976 81), protein arrays and proteomics (Celis, et al., FEBS Lett., 2000, 480, 2 16; Jungblut, et al., Electrophoresis, 1999, 20, 2100 10), expressed sequence tag (EST) sequencing (Celis, et al., FEBS Lett., 2000, 480, 2 16; Larsson, et al., J. Biotechnol., 2000, 80, 143 57), subtractive RNA fingerprinting (SuRF) (Fuchs, et al., Anal. Biochem., 2000, 286, 91 98; Larson, et al., Cytometry, 2000, 41, 203 208), subtractive cloning, differential display (DD) (Jurecic and Belmont, Curr. Opin. Microbiol., 2000, 3, 316 21), comparative genomic hybridization (Carulli, et al., J. Cell Biochem. Suppl., 1998, 31, 286 96), FISH (fluorescent in situ hybridization) techniques (Going and Gusterson, Eur. J. Cancer, 1999, 35, 1895 904) and mass spectrometry methods (To, Comb. Chem. High Throughput Screen, 2000, 3, 235 41).

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

```

We claim:

1. An isolated, biologically active, murine monoclonal, chimeric, or humanized antibody or antigen-binding fragment thereof that specifically binds a bioactive lysophosphatidic acid to decrease the effective concentration of such bioactive lysophosphatidic acid in vivo, wherein said antibody or antibody fragment does not bind keyhole limpet hemocyanin.

2. A pharmaceutical composition comprising a pharmaceutically acceptable carrier and a therapeutically effective amount of an isolated biologically active, murine monoclonal, chimeric, or humanized antibody or antigen-binding fragment thereof according to claim 1.

3. An isolated, biologically active, murine monoclonal, chimeric, or humanized antibody or antigen-binding fragment thereof that specifically binds a bioactive lysophosphatidic acid and exerts a biologic effect, wherein said antibody or antibody fragment does not bind keyhole limpet hemocyanin.

4. A pharmaceutical composition comprising a pharmaceutically acceptable carrier and a therapeutically effective amount of an isolated, biological active, murine monoclonal, chimeric, or humanized antibody or antigen-binding fragment thereof according to claim 3.

5. An isolated, biologically active, murine monoclonal, chimeric, or humanized antibody or antigen-binding fragment thereof according to claim 3 wherein the biologic effect is selected from among: decreasing the effective in vivo concentration of the bioactive lysophosphatidic acid; inhibition of angiogenesis; and inhibition of inflammation.

* * * * *

SEQUENCE LISTING

<160> NUMBER OF SEQ ID NOS: 46

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggratgga gckggrtctt tmtctt                                            26

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtggatag acagatgggg g                                                 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtggatag accgatgggg c                                                 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtggatag actgatgggg g                                                 21

<210> SEQ ID NO 5
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 5
caagggatag acagatgggg c                                                   21

<210> SEQ ID NO 6
<211> LENGTH: 120
<212> TYPE: PRT
<213> ORGANISM: Mus musculus

<400> SEQUENCE: 6

Gln Ala His Leu Gln Gln Ser Asp Ala Glu Leu Val Lys Pro Gly Ala
 1               5                  10                  15

Ser Val Lys Ile Ser Cys Lys Val Ser Gly Phe Ile Phe Ile Asp His
             20                  25                  30

Thr Ile His Trp Met Lys Gln Arg Pro Glu Gln Gly Leu Glu Trp Ile
         35                  40                  45

Gly Cys Ile Ser Pro Arg His Asp Ile Thr Lys Tyr Asn Glu Met Phe
     50                  55                  60

Arg Gly Lys Ala Thr Leu Thr Ala Asp Lys Ser Ser Thr Thr Ala Tyr
 65                  70                  75                  80

Ile Gln Val Asn Ser Leu Thr Phe Glu Asp Ser Ala Val Tyr Phe Cys
                 85                  90                  95

Ala Arg Gly Gly Phe Tyr Gly Ser Thr Ile Trp Phe Asp Phe Trp Gly
            100                 105                 110

Gln Gly Thr Thr Leu Thr Val Ser
        115                 120

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtctctgatt ctagggca                                                       18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actggatggt gggaagatgg                                                     20

<210> SEQ ID NO 9
<211> LENGTH: 107
<212> TYPE: PRT
<213> ORGANISM: Mus musculus

<400> SEQUENCE: 9

Glu Thr Thr Val Thr Gln Ser Pro Ala Ser Leu Ser Met Ala Ile Gly
 1               5                  10                  15

Glu Lys Val Thr Ile Arg Cys Ile Thr Thr Thr Asp Ile Asp Asp Asp

```
                    20                  25                  30
Met Asn Trp Phe Gln Gln Lys Pro Gly Glu Pro Pro Asn Leu Leu Ile
                35                  40                  45

Ser Glu Gly Asn Ile Leu Arg Pro Gly Val Pro Ser Arg Phe Ser Ser
            50                  55                  60

Ser Gly Tyr Gly Thr Asp Phe Leu Phe Thr Ile Glu Asn Met Leu Ser
65                  70                  75                  80

Glu Asp Val Ala Asp Tyr Tyr Cys Leu Gln Ser Asp Asn Leu Pro Phe
                85                  90                  95

Thr Phe Gly Ser Gly Thr Lys Leu Glu Ile Lys
            100                 105

<210> SEQ ID NO 10
<211> LENGTH: 11
<212> TYPE: PRT
<213> ORGANISM: Mus musculus

<400> SEQUENCE: 10

Ile Thr Thr Thr Asp Ile Asp Asp Met Asn
1               5                   10

<210> SEQ ID NO 11
<211> LENGTH: 7
<212> TYPE: PRT
<213> ORGANISM: Mus musculus

<400> SEQUENCE: 11

Glu Gly Asn Ile Leu Arg Pro
1               5

<210> SEQ ID NO 12
<211> LENGTH: 9
<212> TYPE: PRT
<213> ORGANISM: Mus musculus

<400> SEQUENCE: 12

Leu Gln Ser Asp Asn Leu Pro Phe Thr
1               5

<210> SEQ ID NO 13
<211> LENGTH: 5
<212> TYPE: PRT
<213> ORGANISM: Mus musculus

<400> SEQUENCE: 13

Asp His Thr Ile His
1               5

<210> SEQ ID NO 14
<211> LENGTH: 17
<212> TYPE: PRT
<213> ORGANISM: Mus musculus

<400> SEQUENCE: 14

Cys Ile Ser Pro Arg His Asp Ile Thr Lys Tyr Asn Glu Met Phe Arg
1               5                   10                  15

Gly

<210> SEQ ID NO 15
<211> LENGTH: 12
<212> TYPE: PRT
```

<400> SEQUENCE: 15

Gly Gly Phe Tyr Gly Ser Thr Ile Trp Phe Asp Phe
 1               5                  10

<210> SEQ ID NO 16
<211> LENGTH: 403
<212> TYPE: DNA
<213> ORGANISM: Mus musculus

<400> SEQUENCE: 16
agcttgccgc caccatgatt gcctctgctc agttccttgg tctcctgttg ctctgttttc      60
aaggtaccag atgtgaaaca actgtgaccc agtctccagc atccctgtcc atggctatag     120
gagaaaaagt caccatcaga tgcataacca ccactgatat tgatgatgat atgaactggt     180
tccagcagaa gccagggaa cctcctaacc tccttatttc cgaaggcaat attcttcgtc      240
ctggagtccc atcccgattc tccagcagtg gctatggtac agactttctt tttacaattg     300
aaaacatgct ctcagaagat gttgcagatt actactgttt gcagagtgat aacttaccat     360
tcacgttcgg ctcggggaca aagttggaaa taaaacgtga gtg                       403

<210> SEQ ID NO 17
<211> LENGTH: 129
<212> TYPE: PRT
<213> ORGANISM: Mus musculus

<400> SEQUENCE: 17

Met Ile Ala Ser Ala Gln Phe Leu Gly Leu Leu Leu Cys Phe Gln
 1               5                  10                  15

Gly Thr Arg Cys Glu Thr Thr Val Thr Gln Ser Pro Ala Ser Leu Ser
             20                  25                  30

Met Ala Ile Gly Glu Lys Val Thr Ile Arg Cys Ile Thr Thr Thr Asp
         35                  40                  45

Ile Asp Asp Asp Met Asn Trp Phe Gln Gln Lys Pro Gly Glu Pro Pro
     50                  55                  60

Asn Leu Leu Ile Ser Glu Gly Asn Ile Leu Arg Pro Gly Val Pro Ser
 65                  70                  75                  80

Arg Phe Ser Ser Ser Gly Tyr Gly Thr Asp Phe Leu Phe Thr Ile Glu
                 85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
        115                 120                 125

Glu

<210> SEQ ID NO 18
<211> LENGTH: 403
<212> TYPE: DNA
<213> ORGANISM: Mus musculus
<220> FEATURE:
<221> NAME/KEY: CDS
<222> LOCATION: (15)..(401)

<400> SEQUENCE: 18
agcttgccgc cacc atg att gcc tct gct cag ttc ctt ggt ctc ctg ttg        50
              Met Ile Ala Ser Ala Gln Phe Leu Gly Leu Leu Leu
                1               5                  10 ctc tgt ttt caa ggt acc aga tgt gaa aca act gtg acc cag tct cca        98
Leu Cys Phe Gln Gly Thr Arg Cys Glu Thr Thr Val Thr Gln Ser Pro

```
                    15                  20                  25
gca tcc ctg tcc atg gct ata gga gaa aaa gtc acc atc aga tgc ata           146
Ala Ser Leu Ser Met Ala Ile Gly Glu Lys Val Thr Ile Arg Cys Ile
         30                  35                  40 acc acc act gat att gat gat gat gtg aac tgg ttc cag cag aag cca           194
Thr Thr Thr Asp Ile Asp Asp Asp Val Asn Trp Phe Gln Gln Lys Pro
 45                  50                  55                  60 ggg gaa cct cct aac ctc ctt att tcc gaa ggc aat att ctt cgt cct           242
Gly Glu Pro Pro Asn Leu Leu Ile Ser Glu Gly Asn Ile Leu Arg Pro
                 65                  70                  75 gga gtc cca tcc cga ttc tcc agc agt ggc tat ggt aca gac ttt ctt           290
Gly Val Pro Ser Arg Phe Ser Ser Ser Gly Tyr Gly Thr Asp Phe Leu
             80                  85                  90 ttt aca att gaa aac atg ctc tca gaa gat gtt gca gat tac tac tgt           338
Phe Thr Ile Glu Asn Met Leu Ser Glu Asp Val Ala Asp Tyr Tyr Cys
         95                 100                 105 ttg cag agt gat aac tta cca ttc acg ttc ggc tcg ggg aca aag ttg           386
Leu Gln Ser Asp Asn Leu Pro Phe Thr Phe Gly Ser Gly Thr Lys Leu
     110                 115                 120 gaa ata aaa cgt gag tg                                                    403
Glu Ile Lys Arg Glu
125

<210> SEQ ID NO 19
<211> LENGTH: 403
<212> TYPE: DNA
<213> ORGANISM: Mus musculus
<220> FEATURE:
<221> NAME/KEY: CDS
<222> LOCATION: (15)..(401)

<400> SEQUENCE: 19
agcttgccgc cacc atg att gcc tct gct cag ttc ctt ggt ctc ctg ttg           50
                Met Ile Ala Ser Ala Gln Phe Leu Gly Leu Leu Leu
                 1               5                  10 ctc tgt ttt caa ggt acc aga tgt gaa aca act gtg acc cag tct cca           98
Leu Cys Phe Gln Gly Thr Arg Cys Glu Thr Thr Val Thr Gln Ser Pro
         15                  20                  25 gca tcc ctg tcc atg gct ata gga gaa aaa gtc acc atc aga tgc ata           146
Ala Ser Leu Ser Met Ala Ile Gly Glu Lys Val Thr Ile Arg Cys Ile
         30                  35                  40 acc acc act gat att gat gat gat ctt aac tgg ttc cag cag aag cca           194
Thr Thr Thr Asp Ile Asp Asp Asp Leu Asn Trp Phe Gln Gln Lys Pro
 45                  50                  55                  60 ggg gaa cct cct aac ctc ctt att tcc gaa ggc aat att ctt cgt cct           242
Gly Glu Pro Pro Asn Leu Leu Ile Ser Glu Gly Asn Ile Leu Arg Pro
                 65                  70                  75 gga gtc cca tcc cga ttc tcc agc agt ggc tat ggt aca gac ttt ctt           290
Gly Val Pro Ser Arg Phe Ser Ser Ser Gly Tyr Gly Thr Asp Phe Leu
             80                  85                  90 ttt aca att gaa aac atg ctc tca gaa gat gtt gca gat tac tac tgt           338
Phe Thr Ile Glu Asn Met Leu Ser Glu Asp Val Ala Asp Tyr Tyr Cys
         95                 100                 105 ttg cag agt gat aac tta cca ttc acg ttc ggc tcg ggg aca aag ttg           386
Leu Gln Ser Asp Asn Leu Pro Phe Thr Phe Gly Ser Gly Thr Lys Leu
     110                 115                 120 gaa ata aaa cgt gag tg                                                    403
Glu Ile Lys Arg Glu
125

<210> SEQ ID NO 20
```

<211> LENGTH: 403
<212> TYPE: DNA
<213> ORGANISM: Mus musculus
<220> FEATURE:
<221> NAME/KEY: CDS
<222> LOCATION: (15)..(401)

<400> SEQUENCE: 20

```
agcttgccgc cacc atg att gcc tct gct cag ttc ctt ggt ctc ctg ttg        50
                Met Ile Ala Ser Ala Gln Phe Leu Gly Leu Leu Leu
                 1               5                  10 ctc tgt ttt caa ggt acc aga tgt gaa aca act gtg acc cag tct cca        98
Leu Cys Phe Gln Gly Thr Arg Cys Glu Thr Thr Val Thr Gln Ser Pro
         15                  20                  25 gca tcc ctg tcc atg gct ata gga gaa aaa gtc acc atc aga tgc ata       146
Ala Ser Leu Ser Met Ala Ile Gly Glu Lys Val Thr Ile Arg Cys Ile
     30                  35                  40 acc acc act gat att gat gat gat ggt aac tgg ttc cag cag aag cca       194
Thr Thr Thr Asp Ile Asp Asp Asp Gly Asn Trp Phe Gln Gln Lys Pro
 45                  50                  55                  60 ggg gaa cct cct aac ctc ctt att tcc gaa ggc aat att ctt cgt cct       242
Gly Glu Pro Pro Asn Leu Leu Ile Ser Glu Gly Asn Ile Leu Arg Pro
                 65                  70                  75 gga gtc cca tcc cga ttc tcc agc agt ggc tat ggt aca gac ttt ctt       290
Gly Val Pro Ser Arg Phe Ser Ser Ser Gly Tyr Gly Thr Asp Phe Leu
             80                  85                  90 ttt aca att gaa aac atg ctc tca gaa gat gtt gca gat tac tac tgt       338
Phe Thr Ile Glu Asn Met Leu Ser Glu Asp Val Ala Asp Tyr Tyr Cys
         95                 100                 105 ttg cag agt gat aac tta cca ttc acg ttc ggc tcg ggg aca aag ttg       386
Leu Gln Ser Asp Asn Leu Pro Phe Thr Phe Gly Ser Gly Thr Lys Leu
     110                 115                 120 gaa ata aaa cgt gag tg                                                403
Glu Ile Lys Arg Glu
125
```

<210> SEQ ID NO 21
<211> LENGTH: 403
<212> TYPE: DNA
<213> ORGANISM: Mus musculus
<220> FEATURE:
<221> NAME/KEY: CDS
<222> LOCATION: (15)..(401)

<400> SEQUENCE: 21

```
agcttgccgc cacc atg att gcc tct gct cag ttc ctt ggt ctc ctg ttg        50
                Met Ile Ala Ser Ala Gln Phe Leu Gly Leu Leu Leu
                 1               5                  10 ctc tgt ttt caa ggt acc aga tgt gaa aca act gtg acc cag tct cca        98
Leu Cys Phe Gln Gly Thr Arg Cys Glu Thr Thr Val Thr Gln Ser Pro
         15                  20                  25 gca tcc ctg tcc atg gct ata gga gaa aaa gtc acc atc aga tgc ata       146
Ala Ser Leu Ser Met Ala Ile Gly Glu Lys Val Thr Ile Arg Cys Ile
     30                  35                  40 acc acc act gat att gat gat gat ccg aac tgg ttc cag cag aag cca       194
Thr Thr Thr Asp Ile Asp Asp Asp Pro Asn Trp Phe Gln Gln Lys Pro
 45                  50                  55                  60 ggg gaa cct cct aac ctc ctt att tcc gaa ggc aat att ctt cgt cct       242
Gly Glu Pro Pro Asn Leu Leu Ile Ser Glu Gly Asn Ile Leu Arg Pro
                 65                  70                  75 gga gtc cca tcc cga ttc tcc agc agt ggc tat ggt aca gac ttt ctt       290
Gly Val Pro Ser Arg Phe Ser Ser Ser Gly Tyr Gly Thr Asp Phe Leu
             80                  85                  90
```

```
ttt aca att gaa aac atg ctc tca gaa gat gtt gca gat tac tac tgt    338
Phe Thr Ile Glu Asn Met Leu Ser Glu Asp Val Ala Asp Tyr Tyr Cys
        95                 100                 105 ttg cag agt gat aac tta cca ttc acg ttc ggc tcg ggg aca aag ttg    386
Leu Gln Ser Asp Asn Leu Pro Phe Thr Phe Gly Ser Gly Thr Lys Leu
110                 115                 120 gaa ata aaa cgt gag tg                                              403
Glu Ile Lys Arg Glu
125

<210> SEQ ID NO 22
<211> LENGTH: 129
<212> TYPE: PRT
<213> ORGANISM: Mus musculus

<400> SEQUENCE: 22

Met Ile Ala Ser Ala Gln Phe Leu Gly Leu Leu Leu Leu Cys Phe Gln
1               5                   10                  15

Gly Thr Arg Cys Glu Thr Thr Val Thr Gln Ser Pro Ala Ser Leu Ser
            20                  25                  30

Met Ala Ile Gly Glu Lys Val Thr Ile Arg Cys Ile Thr Thr Thr Asp
        35                  40                  45

Ile Asp Asp Asp Val Asn Trp Phe Gln Gln Lys Pro Gly Glu Pro Pro
    50                  55                  60

Asn Leu Leu Ile Ser Glu Gly Asn Ile Leu Arg Pro Gly Val Pro Ser
65                  70                  75                  80

Arg Phe Ser Ser Ser Gly Tyr Gly Thr Asp Phe Leu Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
        115                 120                 125

Glu

<210> SEQ ID NO 23
<211> LENGTH: 129
<212> TYPE: PRT
<213> ORGANISM: Mus musculus

<400> SEQUENCE: 23

Met Ile Ala Ser Ala Gln Phe Leu Gly Leu Leu Leu Leu Cys Phe Gln
1               5                   10                  15

Gly Thr Arg Cys Glu Thr Thr Val Thr Gln Ser Pro Ala Ser Leu Ser
            20                  25                  30

Met Ala Ile Gly Glu Lys Val Thr Ile Arg Cys Ile Thr Thr Thr Asp
        35                  40                  45

Ile Asp Asp Asp Leu Asn Trp Phe Gln Gln Lys Pro Gly Glu Pro Pro
    50                  55                  60

Asn Leu Leu Ile Ser Glu Gly Asn Ile Leu Arg Pro Gly Val Pro Ser
65                  70                  75                  80

Arg Phe Ser Ser Ser Gly Tyr Gly Thr Asp Phe Leu Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
        115                 120                 125
```

Glu

<210> SEQ ID NO 24
<211> LENGTH: 129
<212> TYPE: PRT
<213> ORGANISM: Mus musculus

<400> SEQUENCE: 24

```
Met Ile Ala Ser Ala Gln Phe Leu Gly Leu Leu Leu Cys Phe Gln
  1               5                  10                  15

Gly Thr Arg Cys Glu Thr Thr Val Thr Gln Ser Pro Ala Ser Leu Ser
                 20                  25                  30

Met Ala Ile Gly Glu Lys Val Thr Ile Arg Cys Ile Thr Thr Thr Asp
             35                  40                  45

Ile Asp Asp Asp Gly Asn Trp Phe Gln Gln Lys Pro Gly Glu Pro Pro
         50                  55                  60

Asn Leu Leu Ile Ser Glu Gly Asn Ile Leu Arg Pro Gly Val Pro Ser
 65                  70                  75                  80

Arg Phe Ser Ser Ser Gly Tyr Gly Thr Asp Phe Leu Phe Thr Ile Glu
                 85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
            115                 120                 125

Glu
```

<210> SEQ ID NO 25
<211> LENGTH: 129
<212> TYPE: PRT
<213> ORGANISM: Mus musculus

<400> SEQUENCE: 25

```
Met Ile Ala Ser Ala Gln Phe Leu Gly Leu Leu Leu Cys Phe Gln
  1               5                  10                  15

Gly Thr Arg Cys Glu Thr Thr Val Thr Gln Ser Pro Ala Ser Leu Ser
                 20                  25                  30

Met Ala Ile Gly Glu Lys Val Thr Ile Arg Cys Ile Thr Thr Thr Asp
             35                  40                  45

Ile Asp Asp Asp Pro Asn Trp Phe Gln Gln Lys Pro Gly Glu Pro Pro
         50                  55                  60

Asn Leu Leu Ile Ser Glu Gly Asn Ile Leu Arg Pro Gly Val Pro Ser
 65                  70                  75                  80

Arg Phe Ser Ser Ser Gly Tyr Gly Thr Asp Phe Leu Phe Thr Ile Glu
                 85                  90                  95

Asn Met Leu Ser Glu Asp Val Ala Asp Tyr Tyr Cys Leu Gln Ser Asp
            100                 105                 110

Asn Leu Pro Phe Thr Phe Gly Ser Gly Thr Lys Leu Glu Ile Lys Arg
            115                 120                 125

Glu
```

<210> SEQ ID NO 26
<211> LENGTH: 436
<212> TYPE: DNA
<213> ORGANISM: Mus musculus

<400> SEQUENCE: 26

```
atggcatgga gctgggtctt tctcttcttc ctgtcagtaa ctaccggcgt ccactcccag    60
```

```
gctcacctgc aacagtctga cgctgaattg gtgaaacctg gagcttcagt gaagatatcc      120
tgcaaggttt ctggcttcat tttcattgac catactattc actggatgaa gcagaggcct      180
gaacagggcc tcgaatggat cggatgtatt tctcccagac atgatattac taaatacaat      240
gagatgttca gggcaaggc caccctgact gcagacaagt cctccactac agcctacata       300
caagtcaaca gtctgacatt tgaagactct gcagtctatt tctgtgcaag aggggggttc      360
tacggtagta ctatctggtt tgactttggg ggccaaggca ccactctcac agtctcctca      420
gcctccacca agggcc                                                      436
```

```
<210> SEQ ID NO 27
<211> LENGTH: 145
<212> TYPE: PRT
<213> ORGANISM: Mus musculus

<400> SEQUENCE: 27
```

```
Met Ala Trp Ser Trp Val Phe Leu Phe Phe Leu Ser Val Thr Thr Gly
 1               5                  10                  15

Val His Ser Gln Ala His Leu Gln Gln Ser Asp Ala Glu Leu Val Lys
             20                  25                  30

Pro Gly Ala Ser Val Lys Ile Ser Cys Lys Val Ser Gly Phe Ile Phe
         35                  40                  45

Ile Asp His Thr Ile His Trp Met Lys Gln Arg Pro Glu Gln Gly Leu
     50                  55                  60

Glu Trp Ile Gly Cys Ile Ser Pro Arg His Asp Ile Thr Lys Tyr Asn
 65                  70                  75                  80

Glu Met Phe Arg Gly Lys Ala Thr Leu Thr Ala Asp Lys Ser Ser Thr
                 85                  90                  95

Thr Ala Tyr Ile Gln Val Asn Ser Leu Thr Phe Glu Asp Ser Ala Val
            100                 105                 110

Tyr Phe Cys Ala Arg Gly Gly Phe Tyr Gly Ser Thr Ile Trp Phe Asp
        115                 120                 125

Phe Trp Gly Gln Gly Thr Thr Leu Thr Val Ser Ser Ala Ser Thr Lys
    130                 135                 140

Gly
145
```

```
<210> SEQ ID NO 28
<211> LENGTH: 436
<212> TYPE: DNA
<213> ORGANISM: Mus musculus
<220> FEATURE:
<221> NAME/KEY: CDS
<222> LOCATION: (1)..(435)

<400> SEQUENCE: 28
```

```
atg gca tgg agc tgg gtc ttt ctc ttc ttc ctg tca gta act acc ggc      48
Met Ala Trp Ser Trp Val Phe Leu Phe Phe Leu Ser Val Thr Thr Gly
 1               5                  10                  15 gtc cac tcc cag gct cac ctg caa cag tct gac gct gaa ttg gtg aaa      96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc     144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc     192
Ile Asp His Thr Ile His Trp Met Lys Gln Arg Pro Glu Gln Gly Leu
     50                  55                  60
```

```
gaa tgg atc gga gct att tct ccc aga cat gat att act aaa tac aat       240
Glu Trp Ile Gly Ala Ile Ser Pro Arg His Asp Ile Thr Lys Tyr Asn
 65                  70                  75                  80 gag atg ttc agg ggc aag gcc acc ctg act gca gac aag tcc tcc act       288
Glu Met Phe Arg Gly Lys Ala Thr Leu Thr Ala Asp Lys Ser Ser Thr
                 85                  90                  95 aca gcc tac ata caa gtc aac agt ctg aca ttt gaa gac tct gca gtc       336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac       384
Tyr Phe Cys Ala Arg Gly Gly Phe Tyr Gly Ser Thr Ile Trp Phe Asp
        115                 120                 125 ttt tgg ggc caa ggc acc act ctc aca gtc tcc tca gcc tcc acc aag       432
Phe Trp Gly Gln Gly Thr Thr Leu Thr Val Ser Ser Ala Ser Thr Lys
    130                 135                 140 ggc c                                                                  436
Gly
145

<210> SEQ ID NO 29
<211> LENGTH: 436
<212> TYPE: DNA
<213> ORGANISM: Mus musculus
<220> FEATURE:
<221> NAME/KEY: CDS
<222> LOCATION: (1)..(435)

<400> SEQUENCE: 29 atg gca tgg agc tgg gtc ttt ctc ttc ttc ctg tca gta act acc ggc        48
Met Ala Trp Ser Trp Val Phe Leu Phe Phe Leu Ser Val Thr Thr Gly
  1               5                  10                  15 gtc cac tcc cag gct cac ctg caa cag tct gac gct gaa ttg gtg aaa        96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc       144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc       192
Ile Asp His Thr Ile His Trp Met Lys Gln Arg Pro Glu Gln Gly Leu
     50                  55                  60 gaa tgg atc gga tct att tct ccc aga cat gat att act aaa tac aat       240
Glu Trp Ile Gly Ser Ile Ser Pro Arg His Asp Ile Thr Lys Tyr Asn
 65                  70                  75                  80 gag atg ttc agg ggc aag gcc acc ctg act gca gac aag tcc tcc act       288
Glu Met Phe Arg Gly Lys Ala Thr Leu Thr Ala Asp Lys Ser Ser Thr
                 85                  90                  95 aca gcc tac ata caa gtc aac agt ctg aca ttt gaa gac tct gca gtc       336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac       384
Tyr Phe Cys Ala Arg Gly Gly Phe Tyr Gly Ser Thr Ile Trp Phe Asp
        115                 120                 125 ttt tgg ggc caa ggc acc act ctc aca gtc tcc tca gcc tcc acc aag       432
Phe Trp Gly Gln Gly Thr Thr Leu Thr Val Ser Ser Ala Ser Thr Lys
    130                 135                 140 ggc c                                                                  436
Gly
145

<210> SEQ ID NO 30
<211> LENGTH: 436
```

```
<212> TYPE: DNA
<213> ORGANISM: Mus musculus
<220> FEATURE:
<221> NAME/KEY: CDS
<222> LOCATION: (1)..(435)

<400> SEQUENCE: 30 atg gca tgg agc tgg gtc ttt ctc ttc ttc ctg tca gta act acc ggc      48
Met Ala Trp Ser Trp Val Phe Leu Phe Phe Leu Ser Val Thr Thr Gly
 1               5                  10                  15 gtc cac tcc cag gct cac ctg caa cag tct gac gct gaa ttg gtg aaa      96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc     144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc     192
Ile Asp His Thr Ile His Trp Met Lys Gln Arg Pro Glu Gln Gly Leu
     50                  55                  60 gaa tgg atc gga tgg att tct ccc aga cat gat att act aaa tac aat     240
Glu Trp Ile Gly Trp Ile Ser Pro Arg His Asp Ile Thr Lys Tyr Asn
 65                  70                  75                  80 gag atg ttc agg ggc aag gcc acc ctg act gca gac aag tcc tcc act     288
Glu Met Phe Arg Gly Lys Ala Thr Leu Thr Ala Asp Lys Ser Ser Thr
                 85                  90                  95 aca gcc tac ata caa gtc aac agt ctg aca ttt gaa gac tct gca gtc     336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac     384
Tyr Phe Cys Ala Arg Gly Gly Phe Tyr Gly Ser Thr Ile Trp Phe Asp
        115                 120                 125 ttt tgg ggc caa ggc acc act ctc aca gtc tcc tca gcc tcc acc aag     432
Phe Trp Gly Gln Gly Thr Thr Leu Thr Val Ser Ser Ala Ser Thr Lys
    130                 135                 140 ggc c                                                               436
Gly
145

<210> SEQ ID NO 31
<211> LENGTH: 436
<212> TYPE: DNA
<213> ORGANISM: Mus musculus
<220> FEATURE:
<221> NAME/KEY: CDS
<222> LOCATION: (1)..(435)

<400> SEQUENCE: 31 atg gca tgg agc tgg gtc ttt ctc ttc ttc ctg tca gta act acc ggc      48
Met Ala Trp Ser Trp Val Phe Leu Phe Phe Leu Ser Val Thr Thr Gly
 1               5                  10                  15 gtc cac tcc cag gct cac ctg caa cag tct gac gct gaa ttg gtg aaa      96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc     144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc     192
Ile Asp His Thr Ile His Trp Met Lys Gln Arg Pro Glu Gln Gly Leu
     50                  55                  60 gaa tgg atc gga tat att tct ccc aga cat gat att act aaa tac aat     240
Glu Trp Ile Gly Tyr Ile Ser Pro Arg His Asp Ile Thr Lys Tyr Asn
 65                  70                  75                  80
```

```
gag atg ttc agg ggc aag gcc acc ctg act gca gac aag tcc tcc act       288
Glu Met Phe Arg Gly Lys Ala Thr Leu Thr Ala Asp Lys Ser Ser Thr
             85                  90                  95 aca gcc tac ata caa gtc aac agt ctg aca ttt gaa gac tct gca gtc       336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac       384
Tyr Phe Cys Ala Arg Gly Gly Phe Tyr Gly Ser Thr Ile Trp Phe Asp
            115                 120                 125 ttt tgg ggc caa ggc acc act ctc aca gtc tcc tca gcc tcc acc aag       432
Phe Trp Gly Gln Gly Thr Thr Leu Thr Val Ser Ser Ala Ser Thr Lys
        130                 135                 140 ggc c                                                                 436
Gly
145

<210> SEQ ID NO 32
<211> LENGTH: 436
<212> TYPE: DNA
<213> ORGANISM: Mus musculus
<220> FEATURE:
<221> NAME/KEY: CDS
<222> LOCATION: (1)..(435)

<400> SEQUENCE: 32 atg gca tgg agc tgg gtc ttt ctc ttc ttc ctg tca gta act acc ggc        48
Met Ala Trp Ser Trp Val Phe Leu Phe Phe Leu Ser Val Thr Thr Gly
  1               5                  10                  15 gtc cac tcc cag gct cac ctg caa cag tct gac gct gaa ttg gtg aaa        96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc       144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc       192
Ile Asp His Thr Ile His Trp Met Lys Gln Arg Pro Glu Gln Gly Leu
     50                  55                  60 gaa tgg atc gga cgt att tct ccc aga cat gat att act aaa tac aat       240
Glu Trp Ile Gly Arg Ile Ser Pro Arg His Asp Ile Thr Lys Tyr Asn
 65                  70                  75                  80 gag atg ttc agg ggc aag gcc acc ctg act gca gac aag tcc tcc act       288
Glu Met Phe Arg Gly Lys Ala Thr Leu Thr Ala Asp Lys Ser Ser Thr
             85                  90                  95 aca gcc tac ata caa gtc aac agt ctg aca ttt gaa gac tct gca gtc       336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac       384
Tyr Phe Cys Ala Arg Gly Gly Phe Tyr Gly Ser Thr Ile Trp Phe Asp
            115                 120                 125 ttt tgg ggc caa ggc acc act ctc aca gtc tcc tca gcc tcc acc aag       432
Phe Trp Gly Gln Gly Thr Thr Leu Thr Val Ser Ser Ala Ser Thr Lys
        130                 135                 140 ggc c                                                                 436
Gly
145

<210> SEQ ID NO 33
<211> LENGTH: 436
<212> TYPE: DNA
<213> ORGANISM: Mus musculus
<220> FEATURE:
<221> NAME/KEY: CDS
<222> LOCATION: (1)..(435)
```

<400> SEQUENCE: 33

```
atg gca tgg agc tgg gtc ttt ctc ttc ttc ctg tca gta act acc ggc    48
Met Ala Trp Ser Trp Val Phe Leu Phe Phe Leu Ser Val Thr Thr Gly
 1               5                  10                  15 gtc cac tcc cag gct cac ctg caa cag tct gac gct gaa ttg gtg aaa    96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc   144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc   192
Ile Asp His Thr Ile His Trp Met Lys Gln Arg Pro Glu Gln Gly Leu
     50                  55                  60 gaa tgg atc gga ttt att tct ccc aga cat gat att act aaa tac aat   240
Glu Trp Ile Gly Phe Ile Ser Pro Arg His Asp Ile Thr Lys Tyr Asn
 65                  70                  75                  80 gag atg ttc agg ggc aag gcc acc ctg act gca gac aag tcc tcc act   288
Glu Met Phe Arg Gly Lys Ala Thr Leu Thr Ala Asp Lys Ser Ser Thr
                 85                  90                  95 aca gcc tac ata caa gtc aac agt ctg aca ttt gaa gac tct gca gtc   336
Thr Ala Tyr Ile Gln Val Asn Ser Leu Thr Phe Glu Asp Ser Ala Val
            100                 105                 110 tat ttc tgt gca aga ggg ggg ttc tac ggt agt act atc tgg ttt gac   384
Tyr Phe Cys Ala Arg Gly Gly Phe Tyr Gly Ser Thr Ile Trp Phe Asp
        115                 120                 125 ttt tgg ggc caa ggc acc act ctc aca gtc tcc tca gcc tcc acc aag   432
Phe Trp Gly Gln Gly Thr Thr Leu Thr Val Ser Ser Ala Ser Thr Lys
    130                 135                 140 ggc c                                                             436
Gly
145
```

<210> SEQ ID NO 34
<211> LENGTH: 436
<212> TYPE: DNA
<213> ORGANISM: Mus musculus
<220> FEATURE:
<221> NAME/KEY: CDS
<222> LOCATION: (1)..(435)

<400> SEQUENCE: 34

```
atg gca tgg agc tgg gtc ttt ctc ttc ttc ctg tca gta act acc ggc    48
Met Ala Trp Ser Trp Val Phe Leu Phe Phe Leu Ser Val Thr Thr Gly
 1               5                  10                  15 gtc cac tcc cag gct cac ctg caa cag tct gac gct gaa ttg gtg aaa    96
Val His Ser Gln Ala His Leu Gln Gln Ser Asp Ala Glu Leu Val Lys
             20                  25                  30 cct gga gct tca gtg aag ata tcc tgc aag gtt tct ggc ttc att ttc   144
Pro Gly Ala Ser Val Lys Ile Ser Cys Lys Val Ser Gly Phe Ile Phe
         35                  40                  45 att gac cat act att cac tgg atg aag cag agg cct gaa cag ggc ctc   192
Ile Asp His Thr Ile His Trp Met Lys Gln Arg Pro Glu Gln Gly Leu
     50                  55                  60 gaa tgg atc gga atg att tct ccc aga cat gat att act aaa tac aat   240
Glu Trp Ile Gly Met Ile Ser Pro Arg His Asp Ile Thr Lys Tyr Asn
 65                  70                  75                  80 gag atg ttc agg ggc aag gcc acc ctg act gca gac aag tcc tcc act   288
Glu Met Phe Arg Gly Lys Ala Thr Leu Thr Ala Asp Lys Ser Ser Thr
                 85                  90                  95 aca gcc tac ata caa gtc aac agt ctg aca ttt gaa gac tct gca gtc   336
```

```
                Thr Ala Tyr Ile Gln Val Asn Ser Leu Thr Phe Glu Asp Ser Ala Val
                            100                 105                 110 tat ttc tgt gca aga ggg ggg ttc tac ggt agt act atc tgg ttt gac            384
Tyr Phe Cys Ala Arg Gly Gly Phe Tyr Gly Ser Thr Ile Trp Phe Asp
            115                 120                 125 ttt tgg ggc caa ggc acc act ctc aca gtc tcc tca gcc tcc acc aag            432
Phe Trp Gly Gln Gly Thr Thr Leu Thr Val Ser Ser Ala Ser Thr Lys
        130                 135                 140 ggc c                                                                      436
Gly
145
```

<210> SEQ ID NO 35
<211> LENGTH: 145
<212> TYPE: PRT
<213> ORGANISM: Mus musculus

<400> SEQUENCE: 35

```
Met Ala Trp Ser Trp Val Phe Leu Phe Phe Leu Ser Val Thr Thr Gly
 1               5                   10                  15

Val His Ser Gln Ala His Leu Gln Gln Ser Asp Ala Glu Leu Val Lys
             20                  25                  30

Pro Gly Ala Ser Val Lys Ile Ser Cys Lys Val Ser Gly Phe Ile Phe
         35                  40                  45

Ile Asp His Thr Ile His Trp Met Lys Gln Arg Pro Glu Gln Gly Leu
     50                  55                  60

Glu Trp Ile Gly Ala Ile Ser Pro Arg His Asp Ile Thr Lys Tyr Asn
 65                  70                  75                  80

Glu Met Phe Arg Gly Lys Ala Thr Leu Thr Ala Asp Lys Ser Ser Thr
                 85                  90                  95

Thr Ala Tyr Ile Gln Val Asn Ser Leu Thr Phe Glu Asp Ser Ala Val
            100                 105                 110

Tyr Phe Cys Ala Arg Gly Gly Phe Tyr Gly Ser Thr Ile Trp Phe Asp
        115                 120                 125

Phe Trp Gly Gln Gly Thr Thr Leu Thr Val Ser Ser Ala Ser Thr Lys
    130                 135                 140

Gly
145
```

<210> SEQ ID NO 36
<211> LENGTH: 145
<212> TYPE: PRT
<213> ORGANISM: Mus musculus

<400> SEQUENCE: 36

```
Met Ala Trp Ser Trp Val Phe Leu Phe Phe Leu Ser Val Thr Thr Gly
 1               5                   10                  15

Val His Ser Gln Ala His Leu Gln Gln Ser Asp Ala Glu Leu Val Lys
             20                  25                  30

Pro Gly Ala Ser Val Lys Ile Ser Cys Lys Val Ser Gly Phe Ile Phe
         35                  40                  45

Ile Asp His Thr Ile His Trp Met Lys Gln Arg Pro Glu Gln Gly Leu
     50                  55                  60

Glu Trp Ile Gly Ser Ile Ser Pro Arg His Asp Ile Thr Lys Tyr Asn
 65                  70                  75                  80

Glu Met Phe Arg Gly Lys Ala Thr Leu Thr Ala Asp Lys Ser Ser Thr
                 85                  90                  95
```

```
Thr Ala Tyr Ile Gln Val Asn Ser Leu Thr Phe Glu Asp Ser Ala Val
                100                 105                 110

Tyr Phe Cys Ala Arg Gly Gly Phe Tyr Gly Ser Thr Ile Trp Phe Asp
            115                 120                 125

Phe Trp Gly Gln Gly Thr Thr Leu Thr Val Ser Ser Ala Ser Thr Lys
        130                 135                 140

Gly
145

<210> SEQ ID NO 37
<211> LENGTH: 145
<212> TYPE: PRT
<213> ORGANISM: Mus musculus

<400> SEQUENCE: 37

Met Ala Trp Ser Trp Val Phe Leu Phe Phe Leu Ser Val Thr Thr Gly
 1               5                  10                  15

Val His Ser Gln Ala His Leu Gln Gln Ser Asp Ala Glu Leu Val Lys
            20                  25                  30

Pro Gly Ala Ser Val Lys Ile Ser Cys Lys Val Ser Gly Phe Ile Phe
        35                  40                  45

Ile Asp His Thr Ile His Trp Met Lys Gln Arg Pro Glu Gln Gly Leu
    50                  55                  60

Glu Trp Ile Gly Trp Ile Ser Pro Arg His Asp Ile Thr Lys Tyr Asn
65                  70                  75                  80

Glu Met Phe Arg Gly Lys Ala Thr Leu Thr Ala Asp Lys Ser Ser Thr
                85                  90                  95

Thr Ala Tyr Ile Gln Val Asn Ser Leu Thr Phe Glu Asp Ser Ala Val
                100                 105                 110

Tyr Phe Cys Ala Arg Gly Gly Phe Tyr Gly Ser Thr Ile Trp Phe Asp
            115                 120                 125

Phe Trp Gly Gln Gly Thr Thr Leu Thr Val Ser Ser Ala Ser Thr Lys
        130                 135                 140

Gly
145

<210> SEQ ID NO 38
<211> LENGTH: 145
<212> TYPE: PRT
<213> ORGANISM: Mus musculus

<400> SEQUENCE: 38

Met Ala Trp Ser Trp Val Phe Leu Phe Phe Leu Ser Val Thr Thr Gly
 1               5                  10                  15

Val His Ser Gln Ala His Leu Gln Gln Ser Asp Ala Glu Leu Val Lys
            20                  25                  30

Pro Gly Ala Ser Val Lys Ile Ser Cys Lys Val Ser Gly Phe Ile Phe
        35                  40                  45

Ile Asp His Thr Ile His Trp Met Lys Gln Arg Pro Glu Gln Gly Leu
    50                  55                  60

Glu Trp Ile Gly Tyr Ile Ser Pro Arg His Asp Ile Thr Lys Tyr Asn
65                  70                  75                  80

Glu Met Phe Arg Gly Lys Ala Thr Leu Thr Ala Asp Lys Ser Ser Thr
                85                  90                  95

Thr Ala Tyr Ile Gln Val Asn Ser Leu Thr Phe Glu Asp Ser Ala Val
                100                 105                 110
```

Tyr Phe Cys Ala Arg Gly Gly Phe Tyr Gly Ser Thr Ile Trp Phe Asp
            115                 120                 125

Phe Trp Gly Gln Gly Thr Thr Leu Thr Val Ser Ala Ser Thr Lys
130                 135                 140

Gly
145

<210> SEQ ID NO 39
<211> LENGTH: 145
<212> TYPE: PRT
<213> ORGANISM: Mus musculus

<400> SEQUENCE: 39

Met Ala Trp Ser Trp Val Phe Leu Phe Phe Leu Ser Val Thr Thr Gly
1               5                   10                  15

Val His Ser Gln Ala His Leu Gln Gln Ser Asp Ala Glu Leu Val Lys
            20                  25                  30

Pro Gly Ala Ser Val Lys Ile Ser Cys Lys Val Ser Gly Phe Ile Phe
        35                  40                  45

Ile Asp His Thr Ile His Trp Met Lys Gln Arg Pro Glu Gln Gly Leu
    50                  55                  60

Glu Trp Ile Gly Arg Ile Ser Pro Arg His Asp Ile Thr Lys Tyr Asn
65                  70                  75                  80

Glu Met Phe Arg Gly Lys Ala Thr Leu Thr Ala Asp Lys Ser Ser Thr
                85                  90                  95

Thr Ala Tyr Ile Gln Val Asn Ser Leu Thr Phe Glu Asp Ser Ala Val
            100                 105                 110

Tyr Phe Cys Ala Arg Gly Gly Phe Tyr Gly Ser Thr Ile Trp Phe Asp
        115                 120                 125

Phe Trp Gly Gln Gly Thr Thr Leu Thr Val Ser Ala Ser Thr Lys
    130                 135                 140

Gly
145

<210> SEQ ID NO 40
<211> LENGTH: 145
<212> TYPE: PRT
<213> ORGANISM: Mus musculus

<400> SEQUENCE: 40

Met Ala Trp Ser Trp Val Phe Leu Phe Phe Leu Ser Val Thr Thr Gly
1               5                   10                  15

Val His Ser Gln Ala His Leu Gln Gln Ser Asp Ala Glu Leu Val Lys
            20                  25                  30

Pro Gly Ala Ser Val Lys Ile Ser Cys Lys Val Ser Gly Phe Ile Phe
        35                  40                  45

Ile Asp His Thr Ile His Trp Met Lys Gln Arg Pro Glu Gln Gly Leu
    50                  55                  60

Glu Trp Ile Gly Phe Ile Ser Pro Arg His Asp Ile Thr Lys Tyr Asn
65                  70                  75                  80

Glu Met Phe Arg Gly Lys Ala Thr Leu Thr Ala Asp Lys Ser Ser Thr
                85                  90                  95

Thr Ala Tyr Ile Gln Val Asn Ser Leu Thr Phe Glu Asp Ser Ala Val
            100                 105                 110

Tyr Phe Cys Ala Arg Gly Gly Phe Tyr Gly Ser Thr Ile Trp Phe Asp
        115                 120                 125

```
Phe Trp Gly Gln Gly Thr Thr Leu Thr Val Ser Ser Ala Ser Thr Lys
        130                 135                 140

Gly
145

<210> SEQ ID NO 41
<211> LENGTH: 145
<212> TYPE: PRT
<213> ORGANISM: Mus musculus

<400> SEQUENCE: 41

Met Ala Trp Ser Trp Val Phe Leu Phe Phe Leu Ser Val Thr Thr Gly
  1               5                  10                  15

Val His Ser Gln Ala His Leu Gln Gln Ser Asp Ala Glu Leu Val Lys
             20                  25                  30

Pro Gly Ala Ser Val Lys Ile Ser Cys Lys Val Ser Gly Phe Ile Phe
         35                  40                  45

Ile Asp His Thr Ile His Trp Met Lys Gln Arg Pro Glu Gln Gly Leu
     50                  55                  60

Glu Trp Ile Gly Met Ile Ser Pro Arg His Asp Ile Thr Lys Tyr Asn
 65                  70                  75                  80

Glu Met Phe Arg Gly Lys Ala Thr Leu Thr Ala Asp Lys Ser Ser Thr
                 85                  90                  95

Thr Ala Tyr Ile Gln Val Asn Ser Leu Thr Phe Glu Asp Ser Ala Val
            100                 105                 110

Tyr Phe Cys Ala Arg Gly Gly Phe Tyr Gly Ser Thr Ile Trp Phe Asp
        115                 120                 125

Phe Trp Gly Gln Gly Thr Thr Leu Thr Val Ser Ser Ala Ser Thr Lys
    130                 135                 140

Gly
145

<210> SEQ ID NO 42
<211> LENGTH: 389
<212> TYPE: DNA
<213> ORGANISM: Mus musculus

<400> SEQUENCE: 42
atgattgcct ctgctcagtt ccttggtctc ctgttgctct gttttcaagg taccagatgt      60
gaaacaactg tgacccagtc tccagcatcc ctgtccatgg ctataggaga aaaagtcacc     120
atcagatgca taaccaccac tgatattgat gatgatatga actggttcca gcagaagcca     180
ggggaacctc ctaacctcct tatttccgaa ggcaatattc ttcgtcctgg agtcccatcc     240
cgattctcca gcagtggcta tggtacagac tttcttttta caattgaaaa catgctctca     300
gaagatgttg cagattacta ctgtttgcag agtgataact accattcac gttcggctcg      360 gggacaaagt tggaaataaa acgtgagtg                                        389

<210> SEQ ID NO 43
<211> LENGTH: 389
<212> TYPE: DNA
<213> ORGANISM: Mus musculus
<220> FEATURE:
<221> NAME/KEY: CDS
<222> LOCATION: (1)..(387)

<400> SEQUENCE: 43 atg att gcc tct gct cag ttc ctt ggt ctc ctg ttg          36
            Met Ile Ala Ser Ala Gln Phe Leu Gly Leu Leu Leu
```

```
ctc tgt ttt caa ggt acc aga tgt gaa aca act gtg acc cag tct cca      84
Leu Cys Phe Gln Gly Thr Arg Cys Glu Thr Thr Val Thr Gln Ser Pro
        15                  20                  25 gca tcc ctg tcc atg gct ata gga gaa aaa gtc acc atc aga tgc ata     132
Ala Ser Leu Ser Met Ala Ile Gly Glu Lys Val Thr Ile Arg Cys Ile
    30                  35                  40 acc acc act gat att gat gat gat gtg aac tgg ttc cag cag aag cca     180
Thr Thr Thr Asp Ile Asp Asp Asp Val Asn Trp Phe Gln Gln Lys Pro
45                  50                  55                  60 ggg gaa cct cct aac ctc ctt att tcc gaa ggc aat att ctt cgt cct     228
Gly Glu Pro Pro Asn Leu Leu Ile Ser Glu Gly Asn Ile Leu Arg Pro
                65                  70                  75 gga gtc cca tcc cga ttc tcc agc agt ggc tat ggt aca gac ttt ctt     276
Gly Val Pro Ser Arg Phe Ser Ser Ser Gly Tyr Gly Thr Asp Phe Leu
            80                  85                  90 ttt aca att gaa aac atg ctc tca gaa gat gtt gca gat tac tac tgt     324
Phe Thr Ile Glu Asn Met Leu Ser Glu Asp Val Ala Asp Tyr Tyr Cys
        95                  100                 105 ttg cag agt gat aac tta cca ttc acg ttc ggc tcg ggg aca aag ttg     372
Leu Gln Ser Asp Asn Leu Pro Phe Thr Phe Gly Ser Gly Thr Lys Leu
    110                 115                 120 gaa ata aaa cgt gag tg                                              389
Glu Ile Lys Arg Glu
125

<210> SEQ ID NO 44
<211> LENGTH: 389
<212> TYPE: DNA
<213> ORGANISM: Mus musculus
<220> FEATURE:
<221> NAME/KEY: CDS
<222> LOCATION: (1)..(387)

<400> SEQUENCE: 44 atg att gcc tct gct cag ttc ctt ggt ctc ctg ttg     36
                    Met Ile Ala Ser Ala Gln Phe Leu Gly Leu Leu Leu
                    1               5                   10 ctc tgt ttt caa ggt acc aga tgt gaa aca act gtg acc cag tct cca      84
Leu Cys Phe Gln Gly Thr Arg Cys Glu Thr Thr Val Thr Gln Ser Pro
        15                  20                  25 gca tcc ctg tcc atg gct ata gga gaa aaa gtc acc atc aga tgc ata     132
Ala Ser Leu Ser Met Ala Ile Gly Glu Lys Val Thr Ile Arg Cys Ile
    30                  35                  40 acc acc act gat att gat gat gat ctt aac tgg ttc cag cag aag cca     180
Thr Thr Thr Asp Ile Asp Asp Asp Leu Asn Trp Phe Gln Gln Lys Pro
45                  50                  55                  60 ggg gaa cct cct aac ctc ctt att tcc gaa ggc aat att ctt cgt cct     228
Gly Glu Pro Pro Asn Leu Leu Ile Ser Glu Gly Asn Ile Leu Arg Pro
                65                  70                  75 gga gtc cca tcc cga ttc tcc agc agt ggc tat ggt aca gac ttt ctt     276
Gly Val Pro Ser Arg Phe Ser Ser Ser Gly Tyr Gly Thr Asp Phe Leu
            80                  85                  90 ttt aca att gaa aac atg ctc tca gaa gat gtt gca gat tac tac tgt     324
Phe Thr Ile Glu Asn Met Leu Ser Glu Asp Val Ala Asp Tyr Tyr Cys
        95                  100                 105 ttg cag agt gat aac tta cca ttc acg ttc ggc tcg ggg aca aag ttg     372
Leu Gln Ser Asp Asn Leu Pro Phe Thr Phe Gly Ser Gly Thr Lys Leu
    110                 115                 120 gaa ata aaa cgt gag tg                                              389
Glu Ile Lys Arg Glu
```

<210> SEQ ID NO 45
<211> LENGTH: 389
<212> TYPE: DNA
<213> ORGANISM: Mus musculus
<220> FEATURE:
<221> NAME/KEY: CDS
<222> LOCATION: (1)..(387)

<400> SEQUENCE: 45

```
      atg att gcc tct gct cag ttc ctt ggt ctc ctg ttg        36
      Met Ile Ala Ser Ala Gln Phe Leu Gly Leu Leu Leu
       1               5                  10 ctc tgt ttt caa ggt acc aga tgt gaa aca act gtg acc cag tct cca    84
Leu Cys Phe Gln Gly Thr Arg Cys Glu Thr Thr Val Thr Gln Ser Pro
         15                  20                  25 gca tcc ctg tcc atg gct ata gga gaa aaa gtc acc atc aga tgc ata   132
Ala Ser Leu Ser Met Ala Ile Gly Glu Lys Val Thr Ile Arg Cys Ile
     30                  35                  40 acc acc act gat att gat gat gat ggt aac tgg ttc cag cag aag cca   180
Thr Thr Thr Asp Ile Asp Asp Asp Gly Asn Trp Phe Gln Gln Lys Pro
 45                  50                  55                  60 ggg gaa cct cct aac ctc ctt att tcc gaa ggc aat att ctt cgt cct   228
Gly Glu Pro Pro Asn Leu Leu Ile Ser Glu Gly Asn Ile Leu Arg Pro
                 65                  70                  75 gga gtc cca tcc cga ttc tcc agc agt ggc tat ggt aca gac ttt ctt   276
Gly Val Pro Ser Arg Phe Ser Ser Ser Gly Tyr Gly Thr Asp Phe Leu
             80                  85                  90 ttt aca att gaa aac atg ctc tca gaa gat gtt gca gat tac tac tgt   324
Phe Thr Ile Glu Asn Met Leu Ser Glu Asp Val Ala Asp Tyr Tyr Cys
         95                 100                 105 ttg cag agt gat aac tta cca ttc acg ttc ggc tcg ggg aca aag ttg   372
Leu Gln Ser Asp Asn Leu Pro Phe Thr Phe Gly Ser Gly Thr Lys Leu
    110                 115                 120 gaa ata aaa cgt gag tg                                            389
Glu Ile Lys Arg Glu
125
```

<210> SEQ ID NO 46
<211> LENGTH: 389
<212> TYPE: DNA
<213> ORGANISM: Mus musculus
<220> FEATURE:
<221> NAME/KEY: CDS
<222> LOCATION: (1)..(387)

<400> SEQUENCE: 46

```
      atg att gcc tct gct cag ttc ctt ggt ctc ctg ttg        36
      Met Ile Ala Ser Ala Gln Phe Leu Gly Leu Leu Leu
       1               5                  10 ctc tgt ttt caa ggt acc aga tgt gaa aca act gtg acc cag tct cca    84
Leu Cys Phe Gln Gly Thr Arg Cys Glu Thr Thr Val Thr Gln Ser Pro
         15                  20                  25 gca tcc ctg tcc atg gct ata gga gaa aaa gtc acc atc aga tgc ata   132
Ala Ser Leu Ser Met Ala Ile Gly Glu Lys Val Thr Ile Arg Cys Ile
     30                  35                  40 acc acc act gat att gat gat gat ccg aac tgg ttc cag cag aag cca   180
Thr Thr Thr Asp Ile Asp Asp Asp Pro Asn Trp Phe Gln Gln Lys Pro
 45                  50                  55                  60 ggg gaa cct cct aac ctc ctt att tcc gaa ggc aat att ctt cgt cct   228
Gly Glu Pro Pro Asn Leu Leu Ile Ser Glu Gly Asn Ile Leu Arg Pro
                 65                  70                  75
```

-continued

```
gga gtc cca tcc cga ttc tcc agc agt ggc tat ggt aca gac ttt ctt    276
Gly Val Pro Ser Arg Phe Ser Ser Ser Gly Tyr Gly Thr Asp Phe Leu
             80                  85                  90 ttt aca att gaa aac atg ctc tca gaa gat gtt gca gat tac tac tgt    324
Phe Thr Ile Glu Asn Met Leu Ser Glu Asp Val Ala Asp Tyr Tyr Cys
         95                 100                 105 ttg cag agt gat aac tta cca ttc acg ttc ggc tcg ggg aca aag ttg    372
Leu Gln Ser Asp Asn Leu Pro Phe Thr Phe Gly Ser Gly Thr Lys Leu
        110                 115                 120 gaa ata aaa cgt gag tg                                             389
Glu Ile Lys Arg Glu
125
```